(12) United States Patent
Altenburger et al.

(10) Patent No.: US 8,110,579 B2
(45) Date of Patent: Feb. 7, 2012

(54) 5,6-BISARYL-2-PYRIDINE-CARBOXAMIDE DERIVATIVES, PREPARATION AND APPLICATION THEREOF IN THERAPEUTICS AS UROTENSIN II RECEPTOR ANTAGONISTS

(75) Inventors: Jean-Michel Altenburger, Saint Remy les Chevieuse (FR); Valerie Fossey, Paris (FR); Philip Janiak, Gif sur Yvette (FR); Gilbert Lassalle, Les Molieres (FR); Frederic Petit, Orleans (FR); Jean Claude Vernieres, Penestin (FR)

(73) Assignee: Sanofi-Aventis, Paris (FR)

( * ) Notice: Subject to any disclaimer, the term of this patent is extended or adjusted under 35 U.S.C. 154(b) by 368 days.

(21) Appl. No.: 12/369,200

(22) Filed: Feb. 11, 2009

(65) Prior Publication Data

US 2009/0318473 A1   Dec. 24, 2009

Related U.S. Application Data

(63) Continuation of application No. PCT/FR2007/001357, filed on Aug. 9, 2007.

(30) Foreign Application Priority Data

Nov. 8, 2006   (FR) ..................... 06 07283

(51) Int. Cl.
  *A61K 31/4965* (2006.01)
  *A61K 31/444* (2006.01)
  *A61K 31/4418* (2006.01)
  *C07D 241/02* (2006.01)
  *C07D 401/04* (2006.01)
  *C07D 213/04* (2006.01)

(52) U.S. Cl. .................. 514/255.06; 514/334; 514/354; 546/328; 546/255; 544/406

(58) Field of Classification Search ............. 514/255.06, 514/334, 354; 546/328, 255; 544/406
See application file for complete search history.

(56) References Cited

FOREIGN PATENT DOCUMENTS

| FR | 2856684 | 12/2004 |
|---|---|---|
| WO | WO 03/051850 | 6/2003 |
| WO | WO 2004/073634 | 9/2004 |
| WO | WO 2004/078114 | 9/2004 |

OTHER PUBLICATIONS

Watanabe, T., et. al., Synergistic Effect of Urotensin II With Midly Oxidized LDL on DNA Synthesis in Vascular Smooth Muscle Cells, Circulation, vol. 104, pp. 16-18, (2001).
Ames, R. S., et. al., Human Urotensin-II is a Potent Vasocontrictor and Agonist for the Orphan Receptor GPR14, Nature, (1999), vol. 401, pp. 282-286.
Arunlakshana, O., et. al., Some Quantitative Uses of Drug Antagonists: Brit. J. Pharmacol., (1959), vol. 14, pp. 48-58.
Avenoza, A., et. al., Synthesis of 1-Amino-4-Hydroxycyclohexane-1-Carboxylic Acids, J. Chem. Soc., Perkin Trans. 1, (1999), pp. 3375-3379.
Cottet, F., et. al., Recommendable Routes to Trifluoromethyl-Substituted Pyridine- and Quinolinecarboxylic Acids, European Journal of Organic Chemistry, vol. 8, pp. 1559-1568, (2003).
De Lean, A., et. al., Simultaneous Analysis of Families of Sigmoidal Curves: Application to Bioassay, Radioligand Assay, and Physiological Dose-Response Curves, American J. Physiol.. (1978), vol. 235, No. 2, pp. E97-E102.
Doggrell., S. A., et. al., Urotensin-II and The Cardiovascular System—The Importance of Developing Modulators, Expert Opin. Investig. Drugs. vol. 13, pp. 479-487, (2004).
Douglas, S. A., et, al., Differential Vasoconstrictor Activity of Human Urotensin-II in Vascular Tissue Isolated From the Rat, Mouse, Dog, Pig, Marmoset and Cynomolgus Monkey, British Journal of Pharmacology, (2000), vol. 131, pp. 1262-1274.
Evans, D. A., et. al., A General Method For The Synthesis of Enantiomerically Pure B-Substituted, B-Amino Acids Through A-Substituted Succinic Acid Derivatives, J. Org. Chem., vol. 64, pp. 6411-6417, (1999).
Kelly, T. R., et al., Total Synthesis of Dimethyl Sulfomycinamate, J. Org. Chem., (1996), vol. 61, pp. 4623-4633.
Matsumoto, Y., et al., Intracerebroventricular Administration of Urotensin II Promotes Anxiogenio-Like Behaviors in Rodents, Neuroscience Letters, vol. 358, pp. 99-102, (2004).
Richards, A. M., et. al., Urotensin II in the Cardiovascular System, Peptides, vol. 25, (2004), pp. 1795-1802.
Takashi, K., et. al,, Expression of Urotensin II and Its Receptor in Adrenal Tumors and Stimulation of Proliferation of Cultured Tumor Cells by Urotensin II, Peptides, vol. 24, pp. 301-306, (2003).
Tzanidis, A. et. al.,, Direct Actions of Urotensin II on the Heart: Implication for Cardiac Fibrosis and Hypertrophy, Circulation Research, vol. 93, pp. 246-253, (2003).
Vu, O, B., et. al., Discovery of Potent and Selective SH2 Inhibitors of the Tyrosine Kinase ZAP-70, J. Med, Chem., vol. 42, pp. 4088-4098, (1999).

*Primary Examiner* — Sreeni Padmanabhan
*Assistant Examiner* — Sahar Javanmard
(74) *Attorney, Agent, or Firm* — Scully, Scott, Murphy & Presser, P.C.

(57) ABSTRACT

The present invention relates to derivatives of 5,6-bisaryl-2-pyridine-carboxamide, their preparation and their application in therapeutics as antagonists of urotensin II receptors.

19 Claims, No Drawings

5,6-BISARYL-2-PYRIDINE-CARBOXAMIDE DERIVATIVES, PREPARATION AND APPLICATION THEREOF IN THERAPEUTICS AS UROTENSIN II RECEPTOR ANTAGONISTS

The present invention relates to derivatives of 5,6-bisaryl-2-pyridine-carboxamide, their preparation and their application in therapeutics as antagonists of urotensin II receptors.

Urotensin II is a cyclic peptide comprising 11 amino acids and is considered to be one of the most powerful vasoconstrictors known to date (Ames et al., 1999, Nature 401, 282-286). Its biological activity is mediated by the activation of a receptor with 7 transmembrane domains coupled to proteins G, called GPR14, renamed UT (Urotensin II Receptor) by the International Union of Basic and Clinical Pharmacology (IUPHAR). Activation of urotensin II receptor leads to mobilization of intracellular calcium. Urotensin II and its receptor are strongly expressed in the cardiovascular system, as well as at the renal and cerebral level and in the endocrine system (Richards and Charles, 2004, Peptides 25, 1795-1802). On isolated vessels, human urotensin II causes vasoconstriction, the intensity of which varies in relation to the particular region and species (Douglas et al., 2000, Br. J. Phamacol. 131, 1262-1274). The administration of urotensin II in an anaesthetized primate induces an increase in peripheral vascular resistances and a deterioration of contractility and of cardiac output, which at high doses may lead to cardiovascular collapse and ultimately to the death of the animal (Ames et al., 1999, Nature 401, 282-286). Moreover, urotensin II stimulates the proliferation of the vascular smooth muscle cells and acts in synergy with the mitogenic activity of serotonin and of oxidized LDLs (Low Density Lipoproteins) (Watanabe et al., 2001, Circulation 104; 16-18). On cardiomyocytes in culture, urotensin II induces cellular hypertrophy and an increase in the synthesis of extracellular matrix (Tzanidis A. et al., 2003, Circ. Res. 93, 246-253).

The plasma and urinary levels of urotensin II have been reported to be increased in a certain number of cardiovascular, renal and metabolic pathologies in humans. These pathologies include arterial hypertension, heart failure, renal failure, diabetes and hepatic cirrhosis (Richards and Charles, 2004, Peptides 25, 1795-1802; Doggrell, 2004, Expert Opin Investig Drugs 13, 479-487).

Central effects of urotensin II have also been described (Matsumoto Y. et al., Neurosci. Lett., 2004, 358, 99).

Finally, it has been shown that some tumour cell lines overexpress the urotensin II receptor (Takahashi K. et al., Peptides, 2003, 24, 301).

Antagonists of the urotensin II receptors may be useful for the treatment of congestive heart failure, ischaemic heart disease, myocardial infarction, cardiac hypertrophy and fibrosis, coronary diseases and atherosclerosis, systemic and pulmonary arterial hypertension, post-angioplasty restenosis, acute and chronic renal failure of diabetic and/or hypertensive origin, diabetes, vascular inflammation, and aneurysms. Furthermore, antagonists of the urotensin II receptors may be useful for the treatment of disorders of the central nervous system, including neurodegenerative diseases, cerebrovascular accidents, stress, anxiety, aggressiveness, depression and schizophrenia, as well as vomiting and sleep disorders.

Finally, antagonists of the urotensin II receptors may also be useful for the treatment of some cancers.

The compounds according to the present invention correspond to formula (I):

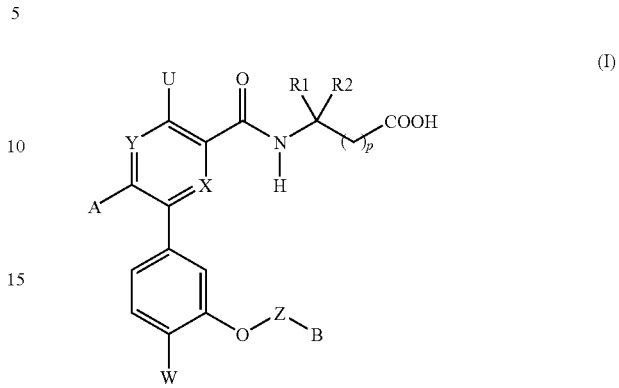

in which:

X and Y represent, independently of one another, a nitrogen atom or a —CR3-group, where R3 represents a hydrogen or halogen atom or an alkyl or alkoxy group;

U represents a hydrogen atom or a group NHR7, where R7 is a hydrogen atom or an alkyl group;

A represents an aryl, heteroaryl or heterocycloalkyl group;

W represents a halogen atom, an alkyl group or a haloalkyl group;

Z represents a bond, a cycloalkylene group or an alkylene group optionally substituted with one or more groups selected from a halogen atom and the alkyl, hydroxy and alkoxy groups;

B represents:
either a group —NR4R5, where R4 and R5 represent, independently of one another, an alkyl, cycloalkyl, hydroxyalkyl or fluoroalkyl group, or alternatively R4 and R5 form, with the nitrogen atom to which they are attached, a 5- or 6-membered ring, such as a pyrrolidinyl or piperidinyl ring, optionally substituted with an alkyl group,
or a heterocycle of the following formula:

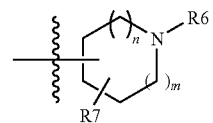

where m and n represent, independently of one another, 0, 1 or 2, and where R6 and R7 represent, independently of one another, a hydrogen atom or an alkyl or cycloalkyl group;

R1 and R2 represent:
either, independently of one another, a hydrogen atom or an alkyl, cycloalkyl, phenyl, benzyl or —CH2-indolyl group, these groups being optionally substituted with one or more groups selected from halogen atoms and the alkyl, fluoroalkyl, alkoxy, hydroxy and —O—CO-alkyl groups, at least one of R1 or R2 being different from a hydrogen atom,
or R1 and R2 together form, with the carbon atom to which they are attached, a mono- or polycyclic system selected from: cycloalkyl, indanyl, tetrahydropyranyl, piperidine, tetrahydronaphthyl, bicyclo[2.2.1]heptyl, bicyclo[3.3.1]nonyl and adamantyl, said mono- or polycyclic system being optionally substituted, in any position (including on a nitrogen atom, if applicable) with one or more groups selected from a halogen atom and the alkyl, fluoroalkyl, hydroxy, alkoxy, —O—CO-alkyl and acyl groups;

p represents an integer equal to 0 or 1.

The compounds of formula (I) can have one or more asymmetric carbon atoms. They can therefore be in the form of enantiomers or of diastereoisomers. These enantiomers, diastereoisomers, and mixtures thereof, including racemic mixtures, form part of the invention.

The compounds of formula (I) can be in the state of bases or can be salified by acids or bases, notably pharmaceutically acceptable acids or bases. Said salts of addition form part of the invention.

These salts are advantageously prepared with pharmaceutically acceptable acids, but the salts of other acids that can be used, for example, for the purification or isolation of the compounds of formula (I), also form part of the invention.

The compounds of formula (I) can also be in the form of hydrates or of solvates, namely in the form of associations or combinations with one or more molecules of water or with a solvent. Said hydrates and solvates also form part of the invention.

Among the compounds of formula (I), we may mention the compounds of formula (I'):

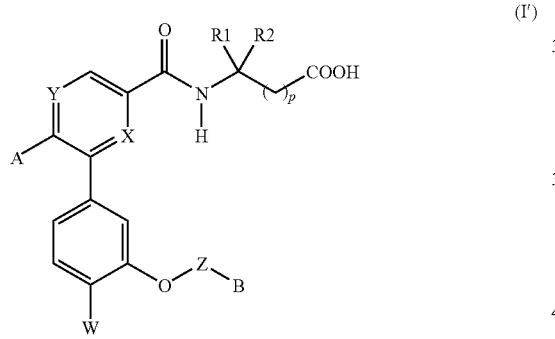

in which:

X and Y represent, independently of one another, a nitrogen atom or a —CR3-group, where R3 represents a hydrogen or halogen atom or an alkyl or alkoxy group;

A represents an aryl, heteroaryl or heterocycloalkyl group selected from the phenyl, thienyl, thiazolyl, pyridinyl, pyrimidinyl, pyridazinyl, pyrazinyl, pyrazolyl and pyrrolidinone groups, said aryl, heteroaryl or heterocycloalkyl group being optionally substituted in any positions with 1 to 3 groups selected from a halogen atom and the alkyl, fluoroalkyl, hydroxy, alkoxy, —NRR', —NR—CO-alkyl, —SO— and —SO$_2$-alkyl groups, where R and R' represent, independently of one another, a hydrogen atom or an alkyl group;

W represents a halogen atom, an alkyl group or a fluoroalkyl group;

Z represents a bond, a cycloalkylene group or an alkylene group optionally substituted with 1 or 2 groups selected from a halogen atom and the alkyl, hydroxy and alkoxy groups;

B represents:
either a group —NR4R5, where R4 and R5 represent, independently of one another, an alkyl, cycloalkyl or fluoroalkyl group, or alternatively R4 and R5 form, with the nitrogen atom to which they are attached, a 5- or 6-membered ring, such as a pyrrolidinyl or piperidinyl ring, optionally substituted with an alkyl group, or a heterocycle of the following formula:

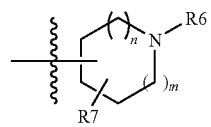

where m and n represent, independently of one another, 0, 1 or 2, and where R6 and R7 represent, independently of one another, a hydrogen atom or an alkyl group;

R1 and R2 represent:
either, independently of one another, a hydrogen atom or an alkyl, cycloalkyl, phenyl, benzyl or —CH$_2$-indolyl group, these groups being optionally substituted with one or more groups selected from halogen atoms and the alkyl, fluoroalkyl, alkoxy, hydroxy and —O—CO-alkyl groups, at least one of R1 or R2 being different from a hydrogen atom, or R1 and R2 together form, with the carbon atom to which they are attached, a mono- or polycyclic system selected from: cycloalkyl, indanyl, tetrahydropyranyl, piperidine, tetrahydronaphthyl, bicyclo[2.2.1]heptyl, bicyclo[3.3.1]nonyl and adamantyl, said mono- or polycyclic system being optionally substituted, in any position with one or more groups selected from a halogen atom and the alkyl, fluoroalkyl, hydroxy, alkoxy, formyl and acetyl groups;

p represents 0 or 1.

Among the compounds of formula (I) according to the invention, we may mention a subgroup of compounds which is defined as follows:

X and Y represent, independently of one another, a nitrogen atom or a —CR3-group, where R3 represents a hydrogen atom or an alkoxy group; and/or U represents a hydrogen atom or a group NHR7, where R7 is a hydrogen atom or an alkyl group; and/or A represents an aryl, heteroaryl or heterocycloalkyl group selected from the phenyl, benzodioxolyl, thienyl, thiazolyl, pyridinyl, pyrazolyl and pyrrolidinone groups, said aryl or heteroaryl group being optionally substituted in any positions with one or more groups selected from a halogen atom and the cyano, alkyl, haloalkyl, hydroxy, alkoxy, —O—(CH$_2$)$_p$—O-alkyl, haloalkoxy, —NRR', —NR—CO-alkyl and —SO$_2$-alkyl groups, where R and R' represent, independently of one another, a hydrogen atom or an alkyl group and p is an integer between 1 and 5 and more particularly between 1 and 3; and/or W represents a halogen atom, an alkyl group or a haloalkyl group; and/or Z represents a bond or an alkylene group optionally substituted with at least one group selected from a halogen atom and the alkyl and hydroxy groups; and/or B represents:
either a group —NR4R5, where R4 and R5 represent, independently of one another, an alkyl, hydroxyalkyl group, or alternatively R4 and R5 form, with the nitrogen atom to which they are attached, a 5- or 6-membered ring, such as a pyrrolidinyl or piperidinyl ring,
or a heterocycle of the following formula:

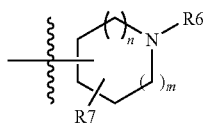

where m and n represent, independently of one another, 0, 1 or 2, and where R6 and R7 represent, independently of one another, a hydrogen atom or an alkyl or cycloalkyl group; and/or R1 and R2 represent:
either, independently of one another, a hydrogen atom or an alkyl, cycloalkyl, phenyl, benzyl or —CH$_2$-indolyl group, these groups being optionally substituted with one or more hydroxy groups, at least one of R1 or R2 being different from a hydrogen atom,
or R1 and R2 together form, with the carbon atom to which they are attached, a mono- or polycyclic system selected from: cycloalkyl, indanyl, tetrahydropyranyl, piperidine, bicyclo[2.2.1]heptyl, bicyclo[3.3.1]nonyl and adamantyl, said mono- or polycyclic system being optionally substituted, in any position (including on a nitrogen atom, if applicable) with one or more groups selected from the alkyl, hydroxy, acetyl and alkoxy groups; and/or p represents an integer equal to 0 or 1.

Among the compounds of formula (I) according to the invention, we may mention a second subgroup of compounds for which X and Y represent, independently of one another, a nitrogen atom or a —CR3-group, where R3 represents a hydrogen or halogen atom or an alkyl or alkoxy group.

More particularly, among the compounds of formula (I) of the second subgroup according to the invention, we may mention a subgroup of compounds for which X and Y represent, independently of one another, a nitrogen atom or a —CR3-group, where R3 represents a hydrogen atom or an alkoxy group.

Among the compounds of formula (I) according to the invention, we may mention a third subgroup of compounds for which U represents a hydrogen atom or a group NHR7, where R7 is a hydrogen atom or an alkyl group.

Among the compounds of formula (I) according to the invention, we may mention a fourth subgroup of compounds for which A represents an aryl, heteroaryl or heterocycloalkyl group optionally substituted.

More particularly, among the compounds of formula (I) of the fourth subgroup according to the invention, we may mention a subgroup of compounds for which A represents an aryl, heteroaryl or heterocycloalkyl group selected from the phenyl, benzodioxolyl, thienyl, thiazolyl, pyridinyl, pyrimidinyl, pyridazinyl, pyrazinyl, pyrazolyl and pyrrolidinone groups, said aryl, heteroaryl or heterocycloalkyl group being optionally substituted in any positions with one or more groups selected from a halogen atom and the cyano, alkyl, haloalkyl, hydroxy, alkoxy, —O—(CH$_2$)$_p$—O-alkyl, haloalkoxy, —NRR', —NR—CO-alkyl, —SO— and —SO$_2$-alkyl groups, where R and R' represent, independently of one another, a hydrogen atom or an alkyl group and p is an integer between 1 and 5.

Even more particularly, among the compounds of formula (I) of the fourth subgroup according to the invention, we may mention a subgroup of compounds for which A represents a group selected from the phenyl, benzodioxolyl, thienyl, thiazolyl, pyridinyl, pyrazolyl and pyrrolidinone groups, said aryl or heteroaryl group being optionally substituted in any positions with one to three groups selected from a halogen atom and the cyano, alkyl, haloalkyl, hydroxy, alkoxy, —O—(CH$_2$)$_p$—O-alkyl, haloalkoxy, —NRR', —NR—CO-alkyl and —SO$_2$-alkyl groups, where R and R' represent, independently of one another, a hydrogen atom or an alkyl group and p is an integer between 1 and 3.

Among the compounds of formula (I) according to the invention, we may mention a fifth subgroup of compounds for which W represents a halogen atom, an alkyl group or a haloalkyl group.

Among the compounds of formula (I) according to the invention, we may mention a sixth subgroup of compounds for which Z represents a bond, a cycloalkylene group or an alkylene group optionally substituted with 1 or 2 groups selected from a halogen atom and the alkyl, hydroxy and alkoxy groups.

More particularly, among the compounds of formula (I) of the sixth subgroup according to the invention, we may mention a subgroup of compounds for which Z represents a bond or an alkylene group optionally substituted with at least one group selected from a halogen atom and the alkyl and hydroxy groups.

Among the compounds of formula (I) according to the invention, we may mention a seventh subgroup of compounds for which B represents:
either a group —NR4R5, where R4 and R5 represent, independently of one another, an alkyl, cycloalkyl, hydroxyalkyl or fluoroalkyl group, or alternatively R4 and R5 form, with the nitrogen atom to which they are attached, a 5- or 6-membered ring, such as a pyrrolidinyl or piperidinyl ring, optionally substituted with an alkyl group,
or a heterocycle of the following formula:

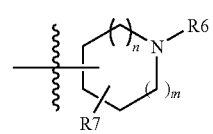

where m and n represent, independently of one another, 0, 1 or 2, and where R6 and R7 represent, independently of one another, a hydrogen atom or an alkyl or cycloalkyl group.

More particularly, among the compounds of formula (I) of the seventh subgroup according to the invention, we may mention a subgroup of compounds for which B represents a group —NR4R5, where R4 and R5 represent, independently of one another, an alkyl, cycloalkyl, hydroxyalkyl or fluoroalkyl group, or alternatively R4 and R5 form, with the nitrogen atom to which they are attached, a 5- or 6-membered ring, such as a pyrrolidinyl or piperidinyl ring, optionally substituted with an alkyl group.

Even more particularly, among the compounds of formula (I) of the seventh subgroup according to the invention, we may mention a subgroup of compounds for which B represents a group —NR4R5, where R4 and R5 represent, independently of one another, an alkyl, hydroxyalkyl or fluoroalkyl group, or alternatively R4 and R5 form, with the nitrogen atom to which they are attached, a 5- or 6-membered ring, such as a pyrrolidinyl or piperidinyl ring.

More particularly, among the compounds of formula (I) of the seventh subgroup according to the invention, we may mention a subgroup of compounds for which B represents a heterocycle of the following formula:

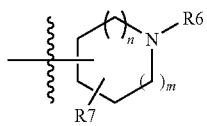

where m and n represent, independently of one another, 0, 1 or 2, and where R6 and R7 represent, independently of one another, a hydrogen atom or an alkyl or cycloalkyl group.

Among the compounds of formula (I) according to the invention, we may mention an eighth subgroup of compounds for which R1 and R2 represent:
  either, independently of one another, a hydrogen atom or an alkyl, cycloalkyl, phenyl, benzyl or —CH$_2$-indolyl group, these groups being optionally substituted with one or more groups selected from halogen atoms and the alkyl, fluoroalkyl, alkoxy, hydroxy and —O—CO-alkyl groups, at least one of R1 or R2 being different from a hydrogen atom,
  or R1 and R2 together form, with the carbon atom to which they are attached, a mono- or polycyclic system selected from: cycloalkyl, indanyl, tetrahydropyranyl, piperidine, tetrahydronaphthyl, bicyclo[2.2.1]heptyl, bicyclo[3.3.1]nonyl and adamantyl, said mono- or polycyclic system being optionally substituted, in any position (including on a nitrogen atom, if applicable) with one or more groups selected from a halogen atom and the alkyl, fluoroalkyl, hydroxy, alkoxy, —O—CO-alkyl and acyl groups.

More particularly, among the compounds of formula (I) of the eighth subgroup according to the invention, we may mention a subgroup of compounds for which R1 and R2 represent, independently of one another, a hydrogen atom or an alkyl, cycloalkyl, phenyl, benzyl or —CH$_2$-indolyl group, these groups being optionally substituted with one or more groups selected from halogen atoms and the alkyl, fluoroalkyl, alkoxy, hydroxy and —O—CO-alkyl groups, at least one of R1 or R2 being different from a hydrogen atom.

Even more particularly, among the compounds of formula (I) of the eighth subgroup according to the invention, we may mention a subgroup of compounds for which R1 and R2 represent, independently of one another, a hydrogen atom or an alkyl, cycloalkyl, phenyl, benzyl or —CH$_2$-indolyl group, these groups being optionally substituted with one or more hydroxy groups, at least one of R1 or R2 being different from a hydrogen atom.

More particularly, among the compounds of formula (I) of the eighth subgroup according to the invention, we may mention a subgroup of compounds for which R1 and R2 together form, with the carbon atom to which they are attached, a mono- or polycyclic system selected from: cycloalkyl, indanyl, tetrahydropyranyl, piperidine, tetrahydronaphthyl, bicyclo[2.2.1]heptyl, bicyclo[3.3.1]nonyl and adamantyl, said mono- or polycyclic system being optionally substituted, in any position (including on a nitrogen atom, if applicable) with one or more groups selected from a halogen atom and the alkyl, hydroxy and alkoxy groups.

Even more particularly, among the compounds of formula (I) of the eighth subgroup according to the invention, we may mention a subgroup of compounds for which R1 and R2 together form, with the carbon atom to which they are attached, a mono- or polycyclic system selected from: cycloalkyl, indanyl, tetrahydropyranyl, piperidine, bicyclo[2.2.1]heptyl, bicyclo[3.3.1]nonyl and adamantyl, said mono- or polycyclic system being optionally substituted, in any position (including on a nitrogen atom, if applicable) with one or more groups selected from the alkyl, hydroxy and alkoxy groups.

Even more particularly, among the compounds of formula (I) of the eighth subgroup according to the invention, we may mention a subgroup of compounds for which R1 and R2 together form, with the carbon atom to which they are attached, a mono- or polycyclic system selected from: cycloalkyl, indanyl, tetrahydropyranyl, piperidine, bicyclo[2.2.1]heptyl, bicyclo[3.3.1]nonyl and adamantyl, said mono- or polycyclic system being optionally substituted, on a carbon atom, with one or more groups selected from the alkyl, hydroxy and alkoxy groups.

Even more particularly, among the compounds of formula (I) of the eighth subgroup according to the invention, we may mention a subgroup of compounds for which R1 and R2 together form, with the carbon atom to which they are attached, a mono- or polycyclic system selected from: cycloalkyl, indanyl, tetrahydropyranyl, piperidine, bicyclo[2.2.1]heptyl, bicyclo[3.3.1]nonyl and adamantyl, said mono- or polycyclic system being optionally substituted, on a nitrogen atom, with a group selected from the alkyl and acyl groups.

Among the compounds of formula (I) according to the invention, we may mention a ninth subgroup of compounds for which p represents an integer equal to 0 or 1.

Within the scope of the present invention, and unless stated otherwise in the text, the following definitions are used:
  halogen atom: a fluorine, chlorine, bromine or iodine atom;
  alkyl group: a saturated linear aliphatic group, comprising 1 to 5 carbon atoms or when the alkyl chain has at least three carbon atoms it can be linear, branched or partially cyclized. As examples, we may mention the methyl, ethyl, propyl, isopropyl, butyl, isobutyl, tertbutyl, pentyl, methylene-cyclopropyl groups;
  alkylene group: an alkyl group as defined above, which is divalent. As examples, we may mention a dimethylene (—CH$_2$—CH$_2$—), propylene, butylene, ethylene, or 2-methylpropylene group;
  cycloalkyl group: a saturated cyclic group, which has from 3 to 8 carbon atoms and which is cyclic. As examples, we may mention the cyclopropyl, cyclopentyl, cyclohexyl and cycloheptyl groups;
  heterocycloalkyl group: a cycloalkyl group as defined above, in which one or two carbons have been substituted with a nitrogen atom. As examples, we may mention the pyrrolidinone group and the piperidine group;
  aryl group: a monocyclic aromatic group comprising 5 or 6 carbon atoms, for example a phenyl group;
  heteroaryl group: a cyclic aromatic group comprising 5 or 6 atoms, one or more of which are heteroatoms such as H and/or S. As examples of heteroaryl groups, we may mention a thienyl, thiazolyl, pyridinyl, pyrimidinyl, pyridazinyl, pyrazinyl, pyrazolyl group;
  cycloalkylene group: a cycloalkyl group as defined above which is divalent;
  fluoroalkyl group: an alkyl group as defined above, in which one or more hydrogen atoms have been substituted with a fluorine atom. As an example, we may mention the trifluoromethyl group;
  alkoxy group: a group of formula —O-alkyl where the alkyl group is as defined previously.

Among the compounds described in the present invention, we may mention a subgroup of compounds corresponding to formula (I) in which:

X and Y represent, independently of one another, a nitrogen atom or a CH group;

A represents a phenyl, pyridinyl, or pyrrolidinone group, substituted in any positions with 1 to 2 groups selected from a halogen atom, such as chlorine or fluorine, and the alkyl, trifluoromethyl, methoxy and N,N-dimethylamine groups;

U represents a hydrogen atom or a group NHR7, where R7 is a hydrogen atom;

W represents a chlorine atom or a trifluoromethyl group;

Z represents a bond or an alkylene group optionally substituted with a methyl group;

B represents:
either a group —NR4R5, where R4 and R5 represent, independently of one another, an alkyl group or alternatively R4 and R5 form, with the nitrogen atom to which they are attached, a 5- or 6-membered ring,
or heterocycles of the following formula:

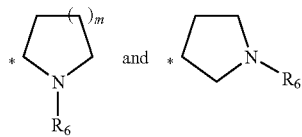

where m=1 or 2 and R6 represents an ethyl or methyl group;

R1 and R2 represent:
either, independently of one another, a hydrogen atom or an isopropyl, tertbutyl group;
or R1 and R2 together form, with the carbon atom to which they are attached, a mono- or polycyclic system selected from: cycloalkyl (such as cyclopentyl, cyclohexyl, or cycloheptyl), tetrahydropyranyl, bicyclo[2.2.1]heptyl, bicyclo[3.3.1]nonyl and adamantyl, said cycloalkyl group being optionally substituted in positions 3 and 4 with a methyl, hydroxy or methoxy group or one or two halogen atoms such as fluorine;
p represents 0 or 1.

We may also mention a second subgroup of compounds among the preferred compounds corresponding to formula (I) in which:

X represents a nitrogen atom and Y represents a CH group;

A represents a phenyl or pyridinyl group, substituted in positions 2, 4, 5 and 6 by one or two groups selected from a halogen atom, such as chlorine or fluorine, and the alkyl groups, such as methyl, ethyl or isopropyl, trifluoromethyl, methoxy and N,N-dimethylamine;

U represents a hydrogen atom or a group NHR7, where R7 is a hydrogen atom;

W represents a chlorine atom or a trifluoromethyl group;

Z represents a bond or an ethylene, propylene or methylpropylene group;

B represents:
either a group —NR4R5, where R4 and R5 represent, independently of one another, a methyl, ethyl or propyl group or form together with the nitrogen atom to which they are attached a 5- or 6-membered ring,
or a heterocycle of the following formula:

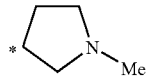

R1 and R2 represent:
either R1 is a hydrogen atom and R2 an isopropyl, tertbutyl group, the carbon atom bearing groups R1 and R2 adopting the absolute configuration S,
or R1 and R2 together form, with the carbon atom to which they are attached, a cycloalkyl group (such as cyclohexyl or cycloheptyl), and adamantyl, said cycloalkyl group being optionally substituted in positions 3 and 4 with a methyl, hydroxy or methoxy group,
p represents 0 or 1.

Among the compounds according to the invention, we may notably mention the following compounds:

2-({[6-{4-chloro-3-[3-(dimethylamino)propoxy]phenyl}-5-(2,6-dimethoxyphenyl)pyridin-2-yl]carbonyl}amino)adamantane-2-carboxylic acid hydrochloride 1-({[6-{4-chloro-3-[3-(dimethylamino)propoxy]phenyl}-4-methoxy-5-(2-methylphenyl)pyridin-2-yl]carbonyl}amino)cyclohexanecarboxylic acid hydrochloride (3S)-3-({[6-{4-chloro-3-[3-(dimethylamino)propoxy]phenyl}-5-(2,4-dimethylphenyl)pyridin-2-yl]carbonyl}amino)-4,4-dimethylpentanoic acid hydrochloride 1-({[6-{4-chloro-3-[3-(dimethylamino)propoxy]phenyl}-5-(2,6-difluorophenyl)pyridin-2-yl]carbonyl}amino)cyclohexanecarboxylic acid hydrochloride 1-({[6-{4-chloro-3-[3-(dimethylamino)propoxy]phenyl}-5-(5-ethoxy-2-methylphenyl)pyridin-2-yl]carbonyl}amino)cyclohexanecarboxylic acid hydrochloride 1-({[6-{4-chloro-3-[3-(dimethylamino)propoxy]phenyl}-5-(2,6-dichlorophenyl)pyridin-2-yl]carbonyl}amino)cyclohexanecarboxylic acid hydrochloride 1-({[6-{4-chloro-3-[3-(dimethylamino)propoxy]phenyl}-5-(2-fluoro-6-methylphenyl)pyridin-2-yl]carbonyl}amino)cyclohexanecarboxylic acid hydrochloride 1-{[(6-{4-chloro-3-[3-(dimethylamino)propoxy]phenyl}-5-[2-methyl-5-(1-methylethyl)phenyl]pyridin-2-yl)carbonyl]amino}cyclohexanecarboxylic acid hydrochloride 1-{[(6-{4-chloro-3-[3-(dimethylamino)propoxy]phenyl}-5-[2-chloro-5-(2-methoxyethoxy)phenyl]pyridin-2-yl)carbonyl]amino}cyclohexanecarboxylic acid hydrochloride 1-({[6-{4-chloro-3-[3-(dimethylamino)propoxy]phenyl}-5-(2,4-dimethylphenyl)pyrazin-2-yl]carbonyl}amino)cyclohexanecarboxylic acid hydrochloride (3S)-3-({[6-{4-chloro-3-[3-(dimethylamino)propoxy]phenyl}-5-(2-chloro-5-ethoxyphenyl)pyrazin-2-yl]carbonyl}amino)-4,4-dimethylpentanoic acid hydrochloride 1-{[(6-{4-chloro-3-[3-(dimethylamino)propoxy]phenyl}-5-[2-(methoxymethyl)phenyl]pyridin-2-yl)carbonyl]amino}cyclohexanecarboxylic acid hydrochloride 1-{[(6-{4-chloro-3-[3-(dimethylamino)propoxy]phenyl}-5-[2-chloro-5-(1-methylethoxy)phenyl]pyridin-2-yl)carbonyl]amino}cyclohexanecarboxylic acid hydrochloride 1-({[6-{4-chloro-3-[3-(dimethylamino)propoxy]phenyl}-5-(2-chloro-5-ethoxyphenyl)pyrazin-2-yl]carbonyl}amino)cyclohexanecarboxylic acid hydrochloride 1-{[(5-[2-chloro-5-(dimethylamino)phenyl]-6-{4-chloro-3-[3-(dimethylamino)propoxy]phenyl}pyridin-2-yl)carbonyl]amino}cyclohexanecarboxylic acid hydrochloride 1-({[6-{4-chloro-3-[3-(dimethylamino)propoxy]phenyl}-5-(2-ethyl-6-fluorophenyl)pyridin-2-yl]carbonyl}amino)cyclohexanecarboxylic acid hydrochloride 1-({[6-{4-chloro-3-[3-(dimethylamino)propoxy]phenyl}-5-(2-methyl-5-propylphenyl)pyridin-2-yl]carbonyl}amino)cyclohexanecarboxylic acid hydrochloride 1-{[(6-{4-chloro-3-[3-(dimethylamino)propoxy]phenyl}-5-[2-(difluoromethyl)-4-methylphenyl]pyridin-2-yl)carbonyl]amino}cyclohexanecarboxylic acid hydrochloride 1-{[(3-chloro-2'-{4-chloro-3-[3-(dimethylamino)propoxy]phenyl}-6-ethoxy-2,3'-bipyridin-6'-yl)carbonyl]amino}cyclohexanecarboxylic acid hydrochloride 1-({[3-amino-6-{4-chloro-3-[3-(dimethylamino)propoxy]phenyl}-5-(2-chloro-5-ethoxyphenyl)pyrazin-2-yl]carbonyl}amino)cyclohexanecarboxylic acid hydrochloride 1-({[6-{4-chloro-3-[3-(dimethylamino)-2-fluoropropoxy]phenyl}-5-(2-methylphenyl)pyridin-2-yl]carbonyl}amino)cyclohexanecarboxylic acid hydrochloride 2-({[6-{4-chloro-3-[3-(dimethylamino)propoxy]phenyl}-5-(2-chlorophenyl)pyridin-2-yl]carbonyl}amino)adamantane-2-carboxylic acid hydrochloride 1-{[(6-{4-chloro-3-[3-(dimethylamino)propoxy]phenyl}-5-[2-(difluoromethyl)-5-methylphenyl]pyridin-2-yl)carbonyl]amino}cyclohexanecarboxylic acid hydrochloride 1-{[(6-{4-chloro-3-[3-(dimethylamino)propoxy]phenyl}-5-[5-(2-methoxyethoxy)-2-methylphenyl]pyridin-2-yl)carbonyl]amino}cyclohexanecarboxylic acid hydrochloride 1-{[(6-{4-chloro-3-[3-(dimethylamino)propoxy]phenyl}-5-[5-(methoxymethyl)-2-methylphenyl]pyridin-2-yl)carbonyl]amino}cyclohexanecarboxylic acid hydrochloride 1-{[(6-{4-chloro-3-[3-(dimethylamino)propoxy]phenyl}-5-[2-methyl-5-(1-methylethoxy)phenyl]pyridin-2-yl)carbonyl]amino}cyclohexanecarboxylic acid hydrochloride 1-{[(6-{4-chloro-3-[3-(dimethylamino)propoxy]phenyl}-5-[2-methyl-5-(2-methylpropoxy)phenyl]pyridin-2-yl)carbonyl]amino}cyclohexanecarboxylic acid hydrochloride 1-{[(6-{4-chloro-3-[3-(dimethylamino)propoxy]phenyl}-5-[5-(cyclopropylmethoxy)-2-methylphenyl]pyridin-2-yl)carbonyl]amino}cyclohexanecarboxylic acid hydrochloride 1-{[6-{4-chloro-3-[3-(dimethylamino)propoxy]phenyl}-5-(2-methyl-5-propoxyphenyl)pyridin-2-yl]carbonyl}amino)cyclohexanecarboxylic acid hydrochloride 2-({[6-{4-chloro-3-[3-(dimethylamino)propoxy]phenyl}-5-(2,6-dimethoxyphenyl)pyridin-2-yl]carbonyl}amino)-2,3-dihydro-1H-indene-2-carboxylic acid 1-({[6-{4-chloro-3-[3-(dimethylamino)propoxy]phenyl}-5-(2,6-dimethoxyphenyl)pyridin-2-yl]carbonyl}amino)cyclopentanecarboxylic acid 2-({[6-{4-chloro-3-[3-(dimethylamino)propoxy]phenyl}-5-(2,6-dimethoxyphenyl)pyridin-2-yl]carbonyl}amino)bicyclo[2.2.1]heptane-2-carboxylic acid hydrochloride N-{[6-{4-chloro-3-[3-(dimethylamino)propoxy]phenyl}-5-(2,6-dimethoxyphenyl)pyridin-2-yl]carbonyl}phenylalanine 1-({[6-{4-chloro-3-[3-(dimethylamino)propoxy]phenyl}-5-(2-methylphenyl)pyridin-2-yl]carbonyl}amino)cyclohexanecarboxylic acid hydrochloride 3-({[6-{4-chloro-3-[3-(dimethylamino)propoxy]phenyl}-5-(2,6-dimethoxyphenyl)pyridin-2-yl]carbonyl}amino)-4-methylpentanoic acid 3-({[6-{4-chloro-3-[3-(dimethylamino)propoxy]phenyl}-5-(2,6-dimethoxyphenyl)pyridin-2-yl]carbonyl}amino)-4-phenylbutanoic acid 3-({[6-{4-chloro-3-[3-(dimethylamino)propoxy]phenyl}-5-(2,6-dimethoxyphenyl)pyridin-2-yl]carbonyl}amino)-4-(1H-indol-3-yl)butanoic acid ({[6-{4-chloro-3-[3-(dimethylamino)propoxy]phenyl}-5-(2,6-dimethoxyphenyl)pyridin-2-yl]carbonyl}amino)(phenyl)acetic acid 3-({[6-{4-chloro-3-[3-(dimethylamino)propoxy]phenyl}-5-(2,6-dimethoxyphenyl)pyridin-2-yl]carbonyl}amino)-3-cyclohexylpropanoic acid 1-({[6-{4-chloro-3-[3-(dimethylamino)propoxy]phenyl}-5-(2,6-dimethoxyphenyl)pyridin-2-yl]carbonyl}amino)cyclohexanecarboxylic acid N-{[6-{4-chloro-3-[3-(dimethylamino)propoxy]phenyl}-5-(2,6-dimethoxyphenyl)pyridin-2-yl]carbonyl}-alpha-methylphenylalanine N-{[6-{4-chloro-3-[3-(dimethylamino)propoxy]phenyl}-5-(2,6-dimethoxyphenyl)pyridin-2-yl]carbonyl}-3-methylisovaline 2-({[6-{4-chloro-3-[(1-methylpyrrolidin-3-yl)oxy]phenyl}-5-(2,6-dimethoxyphenyl)pyridin-2-yl]carbonyl}amino)adamantane-2-carboxylic acid hydrochloride 2-({[6-{4-chloro-3-[(1-methylpiperidin-4-yl)oxy]phenyl}-5-(2,6-dimethoxyphenyl)pyridin-2-yl]carbonyl}amino)adamantane-2-carboxylic acid hydrochloride 2-({[6-{4-chloro-3-[3-(dimethylamino)propoxy]phenyl}-5-(2-methoxyphenyl)pyridin-2-yl]carbonyl}amino)adamantane-2-carboxylic acid hydrochloride 2-({[6-{4-chloro-3-[3-(dimethylamino)propoxy]phenyl}-5-(2-methylphenyl)pyridin-2-yl]carbonyl}amino)adamantane-2-carboxylic acid hydrochloride 2-({[6-{4-chloro-3-[2-(dimethylamino)ethoxy]phenyl}-5-(2,6-dimethoxyphenyl)pyridin-2-yl]carbonyl}amino)adamantane-2-carboxylic acid hydrochloride 2-({[6-{4-chloro-3-[(1-ethylpyrrolidin-3-yl)oxy]phenyl}-5-(2,6-dimethoxyphenyl)pyridin-2-yl]carbonyl}amino)adamantane-2-carboxylic acid hydrochloride 2-{[(6-{4-chloro-3-[3-(dimethylamino)propoxy]phenyl}-5-phenylpyridin-2-yl)carbonyl]amino}adamantane-2-carboxylic acid hydrochloride 2-({[6-{4-chloro-3-[3-(dimethylamino)propoxy]phenyl}-5-(2-oxopyrrolidin-1-yl}pyridin-2-yl]carbonyl}amino)adamantane-2-carboxylic acid hydrochloride 9-({[6-{4-chloro-3-[3-(dimethylamino)propoxy]phenyl}-5-(2,6-dimethoxyphenyl)pyridin-2-yl]carbonyl}amino)bicyclo[3.3.1]nonane-9-carboxylic acid hydrochloride 2-({[6-{4-chloro-3-[3-(diethylamino)propoxy]phenyl}-5-(2,6-dimethoxyphenyl)pyridin-2-yl]carbonyl}amino)adamantane-2-carboxylic acid hydrochloride 2-{[(2-{4-chloro-3-[3-(dimethylamino)propoxy]phenyl}-3,4'-bipyridin-6-yl)carbonyl]amino}adamantane-2-carboxylic acid hydrochloride 2-{[(2'-{4-chloro-3-[3-(dimethylamino)propoxy]phenyl}-2,3'-bipyridin-6'-yl)carbonyl]amino}adamantane-2-carboxylic acid hydrochloride 3-[({4"-chloro-3"-[3-(dimethylamino)propoxy]-2,6-dimethoxy-1,1':2',1"-terphenyl-4'-yl}carbonyl)amino]-4-methylpentanoic acid 3-({[5-{4-chloro-3-[3-(dimethylamino)propoxy]phenyl}-6-(2-methylphenyl)pyridin-3-yl]carbonyl}amino)-4-methylpentanoic acid hydrochloride N-{[6-{4-chloro-3-[3-(dimethylamino)propoxy]phenyl}-5-(2-methylphenyl)pyridin-2-yl]carbonyl}-3-hydroxyphenylalanine hydrochloride 2-({[6-{4-chloro-3-[2-(1-methylpyrrolidin-2-yl)ethoxy]phenyl}-5-(2-methylphenyl)pyridin-2-yl]carbonyl}amino)adamantane-2-carboxylic acid hydrochloride 2-({[6-{4-chloro-3-[2-(1-methylpiperidin-2-yl)ethoxy]phenyl}-5-(2-methylphenyl)pyridin-2-yl]carbonyl}amino)adamantane-2-carboxylic acid hydrochloride 2-({[6-{3-[3-(dimethylamino)propoxy]-4-(trifluoromethyl)phenyl}-5-(2-methylphenyl)pyridin-2-yl]carbonyl}amino)adamantane-2-carboxylic acid hydrochloride 2-({[6-{4-chloro-3-[3-(dimethylamino)propoxy]phenyl}-5-(2-ethylphenyl)pyridin-2-yl]carbonyl}amino)adamantane-2-carboxylic acid hydrochloride 2-{[(6-{4-chloro-3-[3-(dimethylamino)propoxy]phenyl}-5-[2-(trifluoromethyl)phenyl]pyridin-2-yl)carbonyl]amino}adamantane-2-carboxylic acid hydrochloride 2-({[6-(4-chloro-3-{3-[cyclopropyl(methyl)amino]propoxy}phenyl)-5-(2-methylphenyl)pyridin-2-yl]carbonyl}amino)adamantane-2-carboxylic acid hydrochloride 2-{[(6-{4-chloro-3-[3-(dimethylamino)propoxy]phenyl}-5-[2-(dimethylamino)phenyl]pyridin-2-yl)carbonyl]amino}adamantane-2-carboxylic acid hydrochloride 1-{[(3,5-dichloro-2'-{4-chloro-3-[3-(dimethylamino)propoxy]phenyl}-2,3'-bipyridin-6'-yl)carbonyl]amino}cyclohexanecarboxylic acid hydrochloride 1-({[6-{4-chloro-3-[3-(dimethylamino)propoxy]phenyl}-5-(2,4-dimethylphenyl)pyridin-2-yl]carbonyl}amino)cyclohexanecarboxylic acid hydrochloride 4-({[6-{4-chloro-3-[3-(dimethylamino)propoxy]phenyl}-5-(2-methylphenyl)pyridin-2-yl]carbonyl}amino)tetrahydro-2H-pyran-4-carboxylic acid hydrochloride (3R)-3-({[6-{4-chloro-3-[3-(dimethylamino)propoxy]phenyl}-5-(2-methylphenyl)pyridin-2-yl]carbonyl}amino)-4-methylpentanoic acid hydrochloride 2-[({6-[4-chloro-3-(3-piperidin-1-ylpropoxy)phenyl]-5-(2-methylphenyl)pyridin-2-yl}carbonyl)amino]adamantane-2-carboxylic acid hydrochloride 2-({[6-{4-chloro-3-[3-(dimethylamino)butoxy]phenyl}-5-(2-methylphenyl)pyridin-2-yl]carbonyl}amino)adamantane-2-carboxylic acid hydrochloride 2-[({6-[4-chloro-3-(2-piperidin-1-ylethoxy)phenyl]-5-(2-methylphenyl)pyridin-2-yl}carbonyl)amino]adamantane-2-carboxylic acid hydrochloride (3S)-3-({[6-{4-chloro-3-[3-(dimethylamino)propoxy]phenyl}-5-(2-methylphenyl)pyridin-2-yl]carbonyl}amino)-4-methylpentanoic acid hydrochloride 2-[({6-[4-chloro-3-(2-pyrrolidin-1-ylethoxy)phenyl]-5-(2-methylphenyl)pyridin-2-yl}carbonyl)amino]adamantane-2-carboxylic acid hydrochloride 2-[({6-[4-chloro-3-(3-pyrrolidin-1-ylpropoxy)phenyl]-5-(2-methylphenyl)pyridin-2-yl}carbonyl)amino]adamantane-2-carboxylic acid hydrochloride 2-{[(2'-{4-chloro-3-[3-(dimethylamino)propoxy]phenyl}-3-methyl-2,3'-bipyridin-6'-yl)carbonyl]amino}adamantane-2-carboxylic acid hydrochloride 1-({[6-{4-chloro-3-[3-(dimethylamino)propoxy]phenyl}-5-(2-methylphenyl)pyridin-2-yl]carbonyl}amino)-4-methylcyclohexanecarboxylic acid hydrochloride 2-({[6-{4-chloro-3-[3-(dimethylamino)-1-methylpropoxy]phenyl}-5-(2-methylphenyl)pyridin-2-yl]carbonyl}amino)adamantane-2-carboxylic acid hydrochloride 1-({[6-{4-chloro-3-[3-(dimethylamino)propoxy]phenyl}-5-(2-chloro-4-fluorophenyl)pyridin-2-yl]carbonyl}amino)cyclohexanecarboxylic acid hydrochloride 1-({[6-{4-chloro-3-[3-(dimethylamino)propoxy]phenyl}-5-(2-chloro-4-methoxyphenyl)pyridin-2-yl]carbonyl}amino)cyclohexanecarboxylic acid hydrochloride (3S)-3-({[6-{4-chloro-3-[3-(dimethylamino)propoxy]phenyl}-5-(2-chlorophenyl)pyridin-2-yl]carbonyl}amino)-4-methylpentanoic acid hydrochloride 1-({[6-{4-chloro-3-[3-(dimethylamino)propoxy]phenyl}-5-(2-methylphenyl)pyridin-2-yl]carbonyl}amino)-4-hydroxycyclohexanecarboxylic acid hydrochloride 1-({[6-{4-chloro-3-[3-(dimethylamino)propoxy]phenyl}-5-(2-chlorophenyl)pyridin-2-yl]carbonyl}amino)cyclohexanecarboxylic acid hydrochloride 2-({[6-(4-chloro-3-{[(2R)-3-(dimethylamino)-2-hydroxypropyl]oxy}phenyl)-5-(2-methylphenyl)pyridin-2-yl]carbonyl}amino)adamantane-2-carboxylic acid hydrochloride 2-({[6-(4-chloro-3-{[(2S)-3-(dimethylamino)-2-hydroxypropyl]oxy}phenyl)-5-(2-methylphenyl)pyridin-2-yl]carbonyl}amino)adamantane-2-carboxylic acid hydrochloride acetyl-4-({[6-{4-chloro-3-[3-(dimethylamino)propoxy]phenyl}-5-(2-methylphenyl)pyridin-2-yl]carbonyl}amino)piperidine-4-carboxylic acid hydrochloride 2-({[6-{4-chloro-3-[2-(diethylamino)ethoxy]phenyl}-5-(2-methylphenyl)pyridin-2-yl]carbonyl}amino)adamantane-2-carboxylic acid hydrochloride 1-{[(6-{4-chloro-3-[3-(dimethylamino)propoxy]phenyl}-5-[2-(difluoromethyl)phenyl]pyridin-2-yl)carbonyl]amino}cyclohexanecarboxylic acid hydrochloride

[1-({[6-{4-chloro-3-[3-(dimethylamino)propoxy]phenyl}-5-(2-methylphenyl)pyridin-2-yl]carbonyl}amino)cyclohexyl]acetic acid hydrochloride 1-({[6-{4-chloro-3-[3-(dimethylamino)propoxy]phenyl}-5-(2-chlorophenyl)pyridin-2-yl]carbonyl}amino)-4-hydroxycyclohexanecarboxylic acid hydrochloride 1-{[(3-chloro-2'-{4-chloro-3-[3-(dimethylamino)propoxy]phenyl}-2,3'-bipyridin-6'-yl)carbonyl]amino}cyclohexanecarboxylic acid hydrochloride 1-{[(3-amino-2'-{4-chloro-3-[3-(dimethylamino)propoxy]phenyl}-2,3'-bipyridin-6'-yl)carbonyl]amino}cyclohexanecarboxylic acid hydrochloride 1-({[6-{4-chloro-3-[3-(dimethylamino)propoxy]phenyl}-5-(2-methylphenyl)pyridin-2-yl]carbonyl}amino)-3-hydroxycyclohexanecarboxylic acid hydrochloride 1-({[6-{4-chloro-3-[3-(dimethylamino)propoxy]phenyl}-5-(2-methylphenyl)pyridin-2-yl]carbonyl}amino)-3-hydroxycyclohexanecarboxylic acid hydrochloride cis-1-({[6-{4-chloro-3-[3-(dimethylamino)propoxy]phenyl}-5-(2-chlorophenyl)pyridin-2-yl]carbonyl}amino)-4-methoxycyclohexanecarboxylic acid hydrochloride trans-1-({[6-{4-chloro-3-[3-(dimethylamino)propoxy]phenyl}-5-(2-chlorophenyl)pyridin-2-yl]carbonyl}amino)-4-methoxycyclohexanecarboxylic acid hydrochloride trans-1-({[6-{4-chloro-3-[3-(dimethylamino)propoxy]phenyl}-5-(2-methylphenyl)pyridin-2-yl]carbonyl}amino)-4-hydroxycyclohexanecarboxylic acid hydrochloride 1-{[(6-{4-chloro-3-[3-(dimethylamino)propoxy]phenyl}-5-[2-(methylsulphonyl)phenyl]pyridin-2-yl)carbonyl]amino}cyclohexanecarboxylic acid hydrochloride 1-{[(6-{4-chloro-3-[3-(dimethylamino)propoxy]phenyl}-5-[2-(methylsulphonyl)phenyl]pyridin-2-yl)carbonyl]amino}cyclohexanecarboxylic acid hydrochloride 1-{[(2'-{4-chloro-3-[3-(dimethylamino)propoxy]phenyl}-3-methyl-2,3'-bipyridin-6'-yl)carbonyl]amino}cyclohexanecarboxylic acid hydrochloride 1-{[(5-[2-(acetylamino)phenyl]-6-{4-chloro-3-[3-(dimethylamino)propoxy]phenyl}pyridin-2-yl)carbonyl]amino}cyclohexanecarboxylic acid hydrochloride N-{[6-{4-chloro-3-[3-(dimethylamino)propoxy]phenyl}-5-(2-chlorophenyl)pyridin-2-yl]carbonyl}-D-valine hydrochloride 1-{[(2-{4-chloro-3-[3-(dimethylamino)propoxy]phenyl}-2'-methyl-3,3'-bipyridin-6-yl)carbonyl]amino}cyclohexanecarboxylic acid hydrochloride 1-{[(2-{4-chloro-3-[3-(dimethylamino)propoxy]phenyl}-4'-methyl-3,3'-bipyridin-6-yl)carbonyl]amino}cyclohexanecarboxylic acid hydrochloride 1-[({6-[4-chloro-3-(2-pyrrolidin-1-ylethoxy)phenyl]-5-(2-methylphenyl)pyridin-2-yl}carbonyl)amino]-4-hydroxycyclohexanecarboxylic acid hydrochloride 1-({[6-(4-chloro-3-{3-[ethyl(methyl)amino]propoxy}phenyl)-5-(2-methylphenyl)pyridin-2-yl]carbonyl}amino)-4-hydroxycyclohexanecarboxylic acid hydrochloride 1-({[6-{4-chloro-3-[3-(diethylamino)propoxy]phenyl}-5-(2-methylphenyl)pyridin-2-yl]carbonyl}amino)-4-hydroxycyclohexanecarboxylic acid hydrochloride 1-({[6-{4-chloro-3-[4-(dimethylamino)butoxy]phenyl}-5-(2-methylphenyl)pyridin-2-yl]carbonyl}amino)-4-hydroxycyclohexanecarboxylic acid hydrochloride 1-{[(6-{4-chloro-3-[3-(dimethylamino)propoxy]phenyl}-5-[2-(1-methylethyl)phenyl]pyridin-2-yl)carbonyl]amino}-4-hydroxycyclohexanecarboxylic acid hydrochloride 1-({[6-{4-chloro-3-[3-(dimethylamino)propoxy]phenyl}-5-(2-ethylphenyl)pyridin-2-yl]carbonyl}amino)-4-hydroxycyclohexanecarboxylic acid hydrochloride 1-({[6-{4-chloro-3-[3-(dimethylamino)propoxy]phenyl}-5-(5-chloro-2-methylphenyl)pyridin-2-yl]carbonyl}amino)-4-hydroxycyclohexanecarboxylic acid hydrochloride 1-({[6-{4-chloro-3-[3-(dimethylamino)propoxy]phenyl}-5-(2,4-dimethylphenyl)pyridin-2-yl]carbonyl}amino)-4-hydroxycyclohexanecarboxylic acid hydrochloride 1-({[6-{4-chloro-3-[3-(dimethylamino)propoxy]phenyl}-5-(2,5-dimethylphenyl)pyridin-2-yl]carbonyl}amino)-4-hydroxycyclohexanecarboxylic acid hydrochloride 1-({[6-(4-chloro-3-{3-[ethyl(methyl)amino]propoxy}phenyl)-5-(2,4-dimethylphenyl)pyridin-2-yl]carbonyl}amino)-4-hydroxycyclohexanecarboxylic acid hydrochloride 1-({[6-{4-chloro-3-[3-(dimethylamino)propoxy]phenyl}-5-(4-fluoro-2-methylphenyl)pyridin-2-yl]carbonyl}amino)-4-hydroxycyclohexanecarboxylic acid hydrochloride 1-({[6-(4-chloro-3-{3-[methyl(propyl)amino]propoxy}phenyl)-5-(2-ethylphenyl)pyridin-2-yl]carbonyl}amino)-4-hydroxycyclohexanecarboxylic acid hydrochloride 1-({[6-{4-chloro-3-[3-(diethylamino)propoxy]phenyl}-5-(2,4-dimethylphenyl)pyridin-2-yl]carbonyl}amino)-4-hydroxycyclohexanecarboxylic acid hydrochloride 1-({[6-(4-chloro-3-{3-[ethyl(methyl)amino]propoxy}phenyl)-5-(2-ethylphenyl)pyridin-2-yl]carbonyl}amino)-4-hydroxycyclohexanecarboxylic acid hydrochloride 1-({[6-{4-chloro-3-[3-(dimethylamino)propoxy]phenyl}-5-(2-ethylphenyl)pyridin-2-yl]carbonyl}amino)cyclohexanecarboxylic acid hydrochloride 1-({[6-{4-chloro-3-[3-(dimethylamino)-2-methylpropoxy]phenyl}-5-(2-ethylphenyl)pyridin-2-yl]carbonyl}amino)-3-hydroxycyclohexanecarboxylic acid hydrochloride 1-({[6-{4-chloro-3-[3-(dimethylamino)propoxy]phenyl}-5-(2-propylphenyl)pyridin-2-yl]carbonyl}amino)-4-hydroxycyclohexanecarboxylic acid hydrochloride 1-{[(3-chloro-2'-{4-chloro-3-[3-(dimethylamino)propoxy]phenyl}-5-fluoro-2,3'-bipyridin-6α-yl)carbonyl]amino}cyclohexanecarboxylic acid hydrochloride 1-({[6-{4-chloro-3-[3-(dimethylamino)propoxy]phenyl}-5-(2-chloro-5-methylphenyl)pyridin-2-yl]carbonyl}amino)-4-hydroxycyclohexanecarboxylic acid hydrochloride 1-({[3-chloro-2'-(4-chloro-3-{3-[ethyl(methyl)amino]propoxy}phenyl)-2,3'-bipyridin-6'-yl]carbonyl}amino)cyclohexanecarboxylic acid hydrochloride 1-({[6-{4-chloro-3-[3-(dimethylamino)propoxy]phenyl}-5-(2,5-dimethylphenyl)pyridin-2-yl]carbonyl}amino)cyclohexanecarboxylic acid hydrochloride 1-({[6-{4-chloro-3-[3-(dimethylamino)propoxy]phenyl}-5-(2-methylphenyl)pyridin-2-yl]carbonyl}amino)cycloheptanecarboxylic acid hydrochloride (3S)-3-({[6-{4-chloro-3-[3-(dimethylamino)propoxy]phenyl}-5-(2-chloro-5-methylphenyl)pyridin-2-yl]carbonyl}amino)-4-methylpentanoic acid hydrochloride 1-({[6-{4-chloro-3-[3-(dimethylamino)propoxy]phenyl}-5-(2-chloro-5-fluorophenyl)pyridin-2-yl]carbonyl}amino)cyclohexanecarboxylic acid hydrochloride 1-({[6-{4-chloro-3-[3-(dimethylamino)propoxy]phenyl}-5-(3,5-dimethyl-1H-pyrazol-1-yl)pyridin-2-yl]carbonyl}amino)cyclohexanecarboxylic acid hydrochloride 1-({[6-{4-chloro-3-[3-(dimethylamino)propoxy]phenyl}-5-(2-chloro-5-methoxyphenyl)pyridin-2-yl]carbonyl}amino)cyclohexanecarboxylic acid hydrochloride 1-({[6-{3-[3-(dimethylamino)propoxy]-4-ethylphenyl}-5-(2-methylphenyl)pyridin-2-yl]carbonyl}amino)cyclohexanecarboxylic acid hydrochloride 3-({[6-{4-chloro-3-[3-(dimethylamino)propoxy]phenyl}-5-(2-chloro-5-methylphenyl)pyridin-2-yl]carbonyl}amino)-3-cyclobutylpropanoic acid hydrochloride 1-({[6-{4-chloro-3-[3-(dimethylamino)propoxy]phenyl}-5-(2-methylthiophen-3-yl)pyridin-2-yl]carbonyl}amino)cyclohexanecarboxylic acid hydrochloride 3-({[6-{4-chloro-3-[3-(dimethylamino)propoxy]phenyl}-5-(2-chloro-5-methylphenyl)pyridin-2-yl]carbonyl}amino)-3-cyclopropylpropanoic acid hydrochloride 1-({[6-{4-chloro-3-[3-(dimethylamino)propoxy]phenyl}-5-(2-methylphenyl)pyrazin-2-yl]carbonyl}amino)cyclohexanecarboxylic acid hydrochloride 1-({[6-{4-chloro-3-[3-(dimethylamino)propoxy]phenyl}-5-(2-chloro-4-hydroxyphenyl)pyridin-2-yl]carbonyl}amino)cyclohexanecarboxylic acid hydrochloride 1-({[6-{4-chloro-3-[3-(dimethylamino)propoxy]phenyl}-5-(2-chloro-4,5-dimethylphenyl)pyridin-2-yl]carbonyl}amino)cyclohexanecarboxylic acid hydrochloride 1-({[6-{4-chloro-3-[3-(dimethylamino)propoxy]phenyl}-5-(5-methyl-1,3-thiazol-4-yl)pyridin-2-yl]carbonyl}amino)cyclohexanecarboxylic acid hydrochloride 4-({[6-{4-chloro-3-[3-(dimethylamino)propoxy]phenyl}-5-(2-methylphenyl)pyridin-2-yl]carbonyl}amino)oxepane-4-carboxylic acid hydrochloride 3-({[6-{4-chloro-3-[3-(dimethylamino)propoxy]phenyl}-5-(2-chlorophenyl)pyridin-2-yl]carbonyl}amino)-4,4-dimethylpentanoic acid hydrochloride 1-({[6-{4-chloro-3-[3-(dimethylamino)propoxy]phenyl}-5-(2-cyanophenyl)pyridin-2-yl]carbonyl}amino)cyclohexanecarboxylic acid hydrochloride 1-({[6-{4-chloro-3-[3-(dimethylamino)propoxy]phenyl}-5-(4-hydroxy-2-methylphenyl)pyridin-2-yl]carbonyl}amino)cyclohexanecarboxylic acid hydrochloride 1-({[6-{4-chloro-3-[3-(dimethylamino)propoxy]phenyl}-5-(3-fluoro-2-methylphenyl)pyridin-2-yl]carbonyl}amino)cyclohexanecarboxylic acid hydrochloride 1-({[6-{4-chloro-3-[3-(dimethylamino)propoxy]phenyl}-5-(5-hydroxy-2-methylphenyl)pyridin-2-yl]carbonyl}amino)cyclohexanecarboxylic acid hydrochloride 1-({[6-{4-chloro-3-[3-(dimethylamino)propoxy]phenyl}-5-(2-chloro-6-fluorophenyl)pyridin-2-yl]carbonyl}amino)cyclohexanecarboxylic acid hydrochloride 1-({[6-(4-chloro-3-{3-[(2-hydroxyethyl)(methyl)amino]propoxy}phenyl)-5-(2,4-dimethylphenyl)pyridin-2-yl]carbonyl}amino)cyclohexanecarboxylic acid hydrochloride 1-({[6-{4-chloro-3-[3-(dimethylamino)propoxy]phenyl}-5-(3-hydroxy-2-methylphenyl)pyridin-2-yl]carbonyl}amino)cyclohexanecarboxylic acid hydrochloride 1-({[6-{4-chloro-3-[3-(dimethylamino)propoxy]phenyl}-5-(4,5-difluoro-2-methylphenyl)pyridin-2-yl]carbonyl}amino)cyclohexanecarboxylic acid hydrochloride 1-({[6-{4-chloro-3-[3-(dimethylamino)propoxy]phenyl}-5-(6-methyl-1,3-benzodioxol-5-yl)pyridin-2-yl]carbonyl}amino)cyclohexanecarboxylic acid hydrochloride 1-({[6-{4-chloro-3-[3-(dimethylamino)propoxy]phenyl}-5-(3,5-diethyl-1H-pyrazol-1-yl)pyridin-2-yl]carbonyl}amino)cyclohexanecarboxylic acid hydrochloride 1-({[6-{4-chloro-3-[3-(dimethylamino)propoxy]phenyl}-5-(2-chloro-5-ethoxyphenyl)pyridin-2-yl]carbonyl}amino)cyclohexanecarboxylic acid hydrochloride 1-({[5-chloro-2'-{4-chloro-3-[3-(dimethylamino)propoxy]phenyl}-3-(difluoromethyl)-2,3'-bipyridin-6'-yl]carbonyl}amino)cyclohexanecarboxylic acid hydrochloride 1-{[(6-{4-chloro-3-[3-(dimethylamino)propoxy]phenyl}-5-[2-methylphenyl]pyridin-2-yl)carbonyl]amino}cyclohexanecarboxylic acid hydrochloride 1-{[(6-{4-chloro-3-[3-(dimethylamino)propoxy]phenyl}-5-[2-methylphenyl]-3-[methylamino]pyridin-2-yl)carbonyl]amino}cyclohexanecarboxylic acid hydrochloride 1-({[6-{4-chloro-3-[3-(dimethylamino)propoxy]phenyl}-5-(5-ethyl-3-methyl-1H-pyrazol-1-yl)pyridin-2-yl]carbonyl}amino)cyclohexanecarboxylic acid hydrochloride 1-{[(5-[2-chloro-4-(dimethylamino)phenyl]-6-{4-chloro-3-[3-(dimethylamino)propoxy]phenyl}pyridin-2-yl)carbonyl]amino}cyclohexanecarboxylic acid hydrochloride (3S)-3-({[6-{4-chloro-3-[3-(dimethylamino)propoxy]phenyl}-5-(2-chlorophenyl)pyridin-2-yl]carbonyl}amino)-4,4-dimethylpentanoic acid hydrochloride 1-{[(6-{4-chloro-3-[3-(dimethylamino)propoxy]phenyl}-5-[2-chloro-5-(trifluoromethoxy)phenyl]pyridin-2-yl)carbonyl]amino}cyclohexanecarboxylic acid hydrochloride 1-({[3-amino-6-{4-chloro-3-[3-(dimethylamino)propoxy]phenyl}-5-(2-methylphenyl)pyrazin-2-yl]carbonyl}amino)cyclohexanecarboxylic acid hydrochloride 1-({[6-{4-chloro-3-[3-(dimethylamino)propoxy]phenyl}-5-(2,4-dichlorophenyl)pyridin-2-yl]carbonyl}amino)cyclohexanecarboxylic acid hydrochloride 1-({[6-{4-chloro-3-[3-(dimethylamino)propoxy]phenyl}-5-(2-methylphenyl)pyridin-2-yl]carbonyl}amino)-4,4-difluorocyclohexanecarboxylic acid hydrochloride 1-({[6-{4-chloro-3-[3-(dimethylamino)propoxy]phenyl}-3-(methylamino)-5-(2-methylphenyl)pyridin-2-yl]carbonyl}amino)cyclohexanecarboxylic acid hydrochloride 1-({[6-{4-chloro-3-[3-(dimethylamino)propoxy]phenyl}-5-(2-chloro-4-fluorophenyl)pyridin-2-yl]carbonyl}amino)cyclohexanecarboxylic acid hydrochloride 1-({[6-{4-chloro-3-[3-(dimethylamino)propoxy]phenyl}-5-(2-chloro-4-methoxyphenyl)pyridin-2-yl]carbonyl}amino)cyclohexanecarboxylic acid hydrochloride 1-{[(6-{4-chloro-3-[3-(dimethylamino)propoxy]phenyl}-5-[2-(difluoromethyl)phenyl]pyridin-2-yl)carbonyl]amino}cyclohexanecarboxylic acid hydrochloride In accordance with the invention, the compounds of general formula (I) can be prepared according to the method given below, shown in scheme 1.

When, in the starting compound of formula (XI), X represents a nitrogen atom, Y represents a carbon atom (i.e. a group of formula —CR$_3$— as defined with reference to the compounds of formula (I) according to the invention) and U represents a hydrogen atom, or alternatively X represents a carbon atom, Y represents a nitrogen atom and U represents a hydrogen atom, or alternatively X and Y represent a nitrogen atom and U represents a hydrogen atom, then we can carry out, in a stage (i), a coupling reaction of the SUZUKI type, catalysed by a palladium (0) derivative such as tetrakis(triphenylphosphine)palladium (0) [Pd(PPh$_3$)$_4$], between the compound of formula (XI) (where Q=OH or Br and T=halogen atom, such as a bromine or iodine atom) and a boronic acid of formula (IX), where GP represents a benzyl group optionally substituted with one or more alkoxy groups, in the presence of a base such as potassium phosphate and in a solvent such as N,N-dimethylformamide (DMF) at a temperature of about 95° C. This reaction permits regioselective substitution of function T with the phenoxy nucleus to give compound (VIII).

The OH function of compound (VIII) is then converted to a leaving group such as trifluoromethanesulphonate (OTf), in stage (ii), by means of trifluoromethanesulphonic anhydride in the presence of a base such as triethylamine (TEA) and in a solvent such as dichloromethane (DCM) to give the compound of formula (VII).

The trifluoromethanesulphonate group thus obtained makes it possible, owing to its reactivity, to introduce, in stage (iii), the nucleus A by an organopalladium coupling reaction of the type:

either SUZUKI, between compound (VII) and a boronic acid or ester of respective formulae A-B(OH)$_2$ or

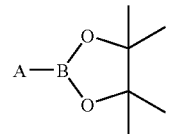

in the presence of a catalytic amount of a palladium derivative such as Pd(PPh$_3$)$_4$, in the presence of a base such as potassium phosphate and of a solvent such as DMF, at a temperature of 90° C.;

or STILLE, between compound (VII) and an aryltributylstannane or heteroarylstannane derivative ASnBu$_3$ in the presence of a catalytic amount of copper iodide (CuI) and of a derivative of palladium (II) such as [1,1'-bis(cyclopentadienyldiphenylphosphino)ferrocene]palladium (II) dichloride [PdCl$_2$(dppf)] and of a solvent such as 1,4-dioxan at a temperature of 90° C.;

or HARTWIG-BUCHWALD, between compound (VII) and an amide such as 2-pyrrolidinone, in the presence of a catalytic amount of a phosphine such as 9,9-dimethyl-4,5-bis-(diphenylphosphino)xanthene (XantPhos) and of a derivative of palladium (0) such as tris(dibenzylideneacetone)dipalladium (0) [Pd$_2$(dba)$_3$], using a base such as caesium carbonate, and in a solvent such as DMF at a temperature of 70° C.

We thus obtain compound (VI).

Alternatively, in the starting compound of formula (XI), when X and Y represent carbon atoms and U represents a hydrogen atom, Q an iodine atom and T a bromine atom, or alternatively X and Y represent a nitrogen atom and U represents a group NHR (as defined with reference to the compounds of formula (I) according to the invention), Q and T atoms of chlorine, bromine or iodine, the order of introduction of groups A and phenoxy on the starting phenyl nucleus is reversed (scheme 1).

In this case, a first reaction of the SUZUKI type (stage (iv)) with a boronic acid A-B(OH)$_2$ permits the selective introduction of a group A in place of the halogen atom Q. The reaction is carried out in the presence of a catalytic amount of a palladium derivative such as Pd(PPh$_3$)$_4$ and of a base such as caesium carbonate, in a solvent such as DMF at a temperature of 90° C. Then a second reaction of the SUZUKI type is carried out (stage (v)) between the boronic ester (XII) or the boronic acid (IX) and compound (X), in the presence of a catalytic amount of a palladium derivative such as Pd(PPh$_3$)$_4$ and of a base such as caesium carbonate, in a solvent such as DMF at a temperature of 90° C. We thus obtain compound (VI).

Deprotection of the phenol function of the compound of formula (VI) by boron tribromide at −78° C., trifluoroacetic acid (TFA) at room temperature or hydrogen chloride at 0° C. in DCM (stage (vi)) leads to the compound of formula (V).

The introduction of group Z—B in stage (vii) can be carried out:
either by alkylation of compound (V) with a chlorine derivative Cl—Z—B in the presence of a weak inorganic base such as caesium carbonate and in a polar aprotic solvent such as DMF at a temperature between 80 and 100° C., such as 90° C.,
or by MITSUNOBU reaction between compound (V) and an alcohol of formula HO—Z—B in the presence of triphenylphosphine, diisopropyl azodicarboxylate (DIAD), and a catalytic amount of a weak organic base such as TEA at 0° C. in an aprotic solvent such as tetrahydrofuran (THF).

The compound of formula (IV) is then saponified in stage (viii), by means of a strong inorganic base such as potassium hydroxide in a water/methanol mixture maintained at room temperature (RT) or heated under reflux, to give, after acidification with a strong acid such as 1N hydrochloric acid (HCl), compound (III).

Within the scope of the present invention, room temperature means a temperature between 20 and 25° C.

A peptide coupling reaction (stage (ix)) between compound (III) and amines of formula (II) in the presence of a coupling agent such as carbonyldiimidazole (CDI), N-[(1H-benzotriazol-1-yloxy)(dimethylamino)methylidene]-N-methylmethanaminium tetrafluoroborate (TBTU) or N-[3-(dimethylamino)propyl-N'-ethyl carbodiimide hydrochloride (EDC.HCl) and an organic base such as N,N'-diisopropylethylamine (DIEA) and in a polar aprotic solvent such as DMF at room temperature leads to the compounds of formula (I) according to the present invention.

Scheme 2 describes the synthesis of the boronic derivatives (IX) and (XII).

The case when W=CF$_3$

2-Amino-5-nitrophenol (XVI) is converted to the iodine derivative (XV) by a SANDMEYER reaction in an aqueous environment at 0° C., in the presence of sodium iodide and with a co-solvent such as dimethylsulphoxide (DMSO). Protection of the phenol function (stage i) by a benzyl group is effected with a halogen derivative such as benzyl bromide in the presence of a base such as potassium carbonate (K$_2$CO$_3$) in a solvent such as DMF at 60° C. Substitution of the iodine atom with the trifluoromethyl group (*Eur. J. Org. Chem.* (2003) pp. 1559-1568), carried out with trifluoromethyltrimethylsilane in the presence of CuI and potassium fluoride in a solvent such as N-methylpyrrolidinone (NMP) at 45° C. (stage ii), leads to compound (XIV) which, after reduction of the nitro function to an amino function by a reducing agent such as iron at 70° C. in an ethanol (EtOH)/water/acetic acid (AcOH) mixture, is converted to the iodine derivative (XIII) by means of a second SANDMEYER reaction (stage iii).

In stage (iv), a reaction of metal-halogen exchange effected between compound (XIII) and isopropyl magnesium chloride (iPrMgCl) at −50° C. in a solvent such as THF, followed by addition of triisopropylborate, leads after acidolysis with an acid such as HCl 5N, to boronic acid (IX).

The case when W=Cl

Protection of the 2-chloro-5-iodophenol (XVIIa) by a benzyl or paramethoxybenzyl group as described in stage (i) leads to the iodine derivative (XVII) which can be converted:
either, in stage (iv), to boronic acid (IX) as described previously,
or, in stage (v), to boronic ester (XII) by a coupling reaction with 4,4,4',4',5,5,5',5'-octamethyl-2,2'-bi-dioxaborolane in the presence of a base such as potassium acetate (KOAc) and a catalytic amount of a palladium derivative (II) such as [PdCl$_2$(dppf)], in a solvent such as DMSO at 100° C.

Alternatively, a subgroup of compounds of formula (Ia) according to the present invention, where group A represents a 2,6-dimethoxybenzene nucleus, was prepared in the following way (scheme 3):
Condensation of 2,6-dimethoxybenzaldehyde on 2-cyanoacetic acid (stage i) in the presence of ammonium acetate and a base such as pyridine, heating under reflux of a solvent such as toluene, leads to derivative (XX).
Derivative (XX) is then treated with diisobutylaluminium hydride (DIBAL-H) at 0° C. in a solvent such as toluene. The aldehyde thus obtained is reacted (stage ii) with ethyl 2-azido acetate at −10° C. in the presence of a base such as sodium ethoxide in a solvent such as ethanol to obtain the diene (XIX). In stage (iii), treatment of diene (XIX) with triphenylphosphine al RT in a solvent such as DCM leads to azatriphenylphosphoranylidene (XVIII).
Reaction (stage iv) between derivative (XVIII) and the aldehyde (XVII) in a solvent such as acetonitrile leads, via the cyclization in situ at 100° C. of an intermediate imine according to an electrocyclic cyclization/dehydrogenation multistep process, to the pyridine derivative (IVa).
The steps of alkylation or MITSUNOBU reaction (stage v), saponification (stage vi) then peptide coupling (stage vii) described previously in scheme 1 and applied to derivative (IVa) lead to the compounds of formula (Ia) according to the present invention.

In schemes 1 and 2, when the method of preparation of the starting compounds, the intermediates and the reagents is not described, they are available commercially or are described in the literature, or alternatively can be prepared according to methods that are known by a person skilled in the art.

Scheme 1
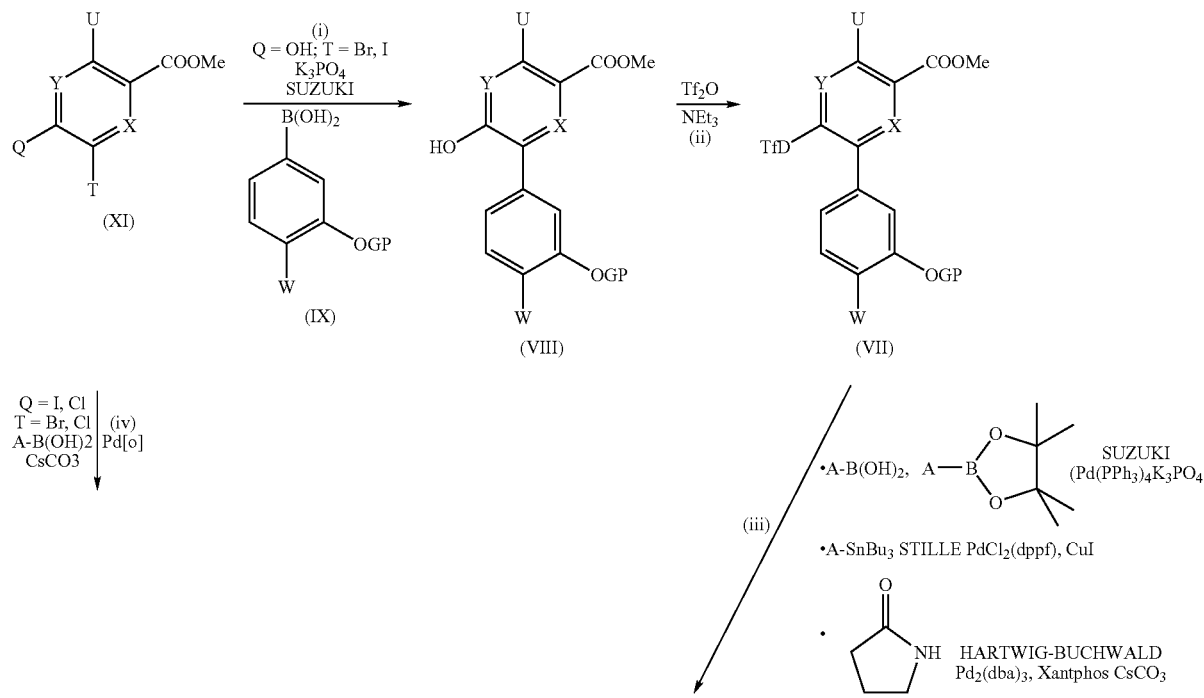
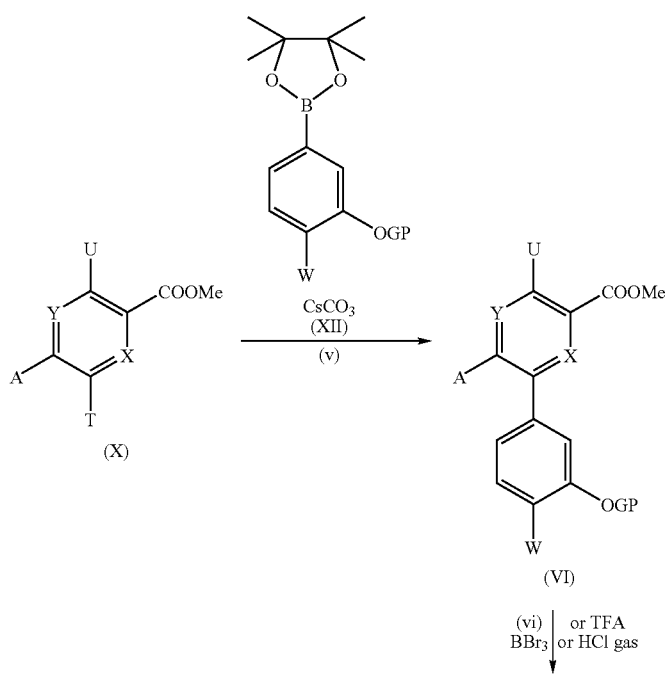

-continued
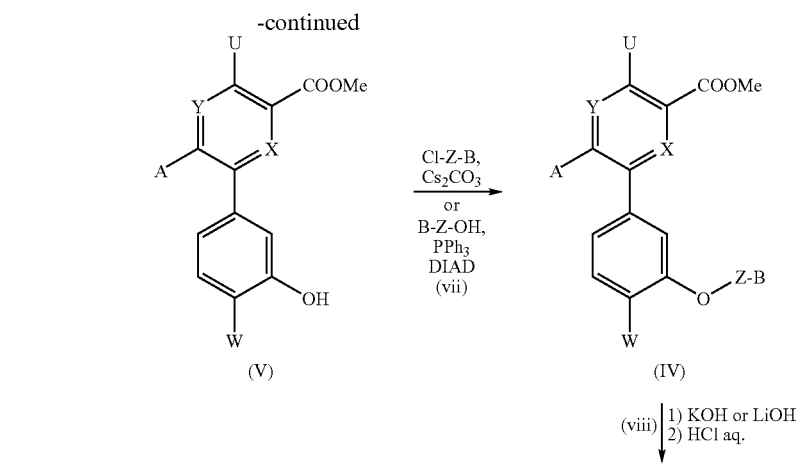
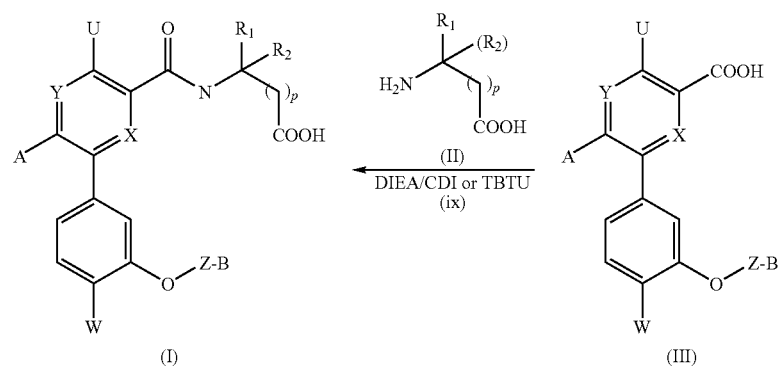
Scheme 2
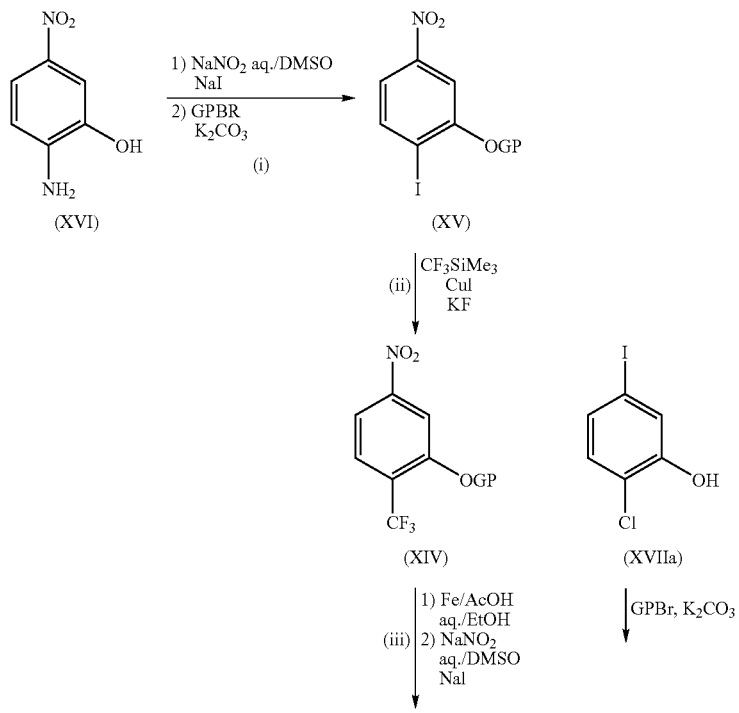

-continued
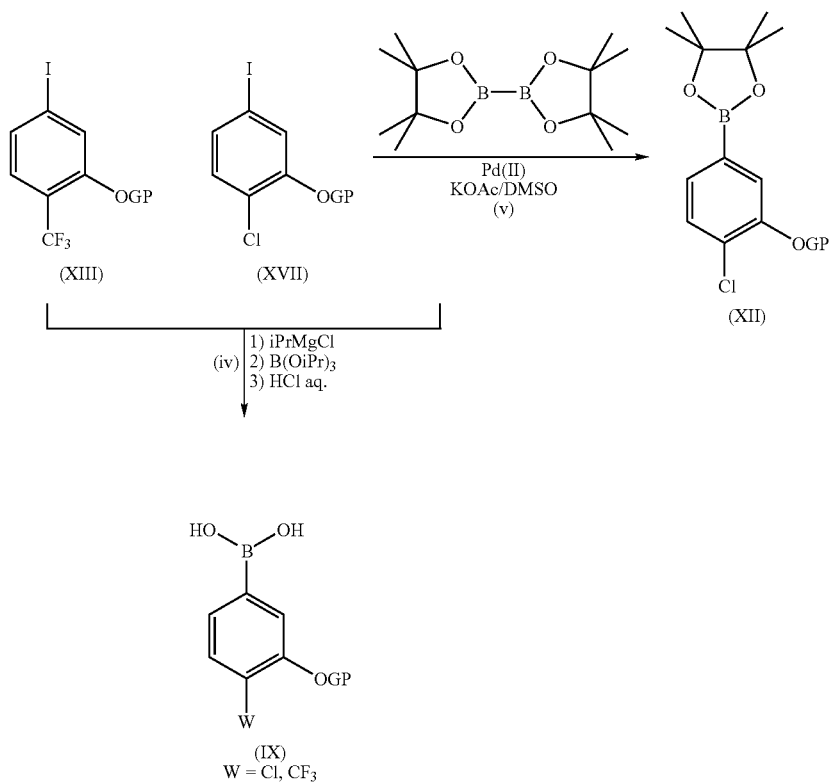
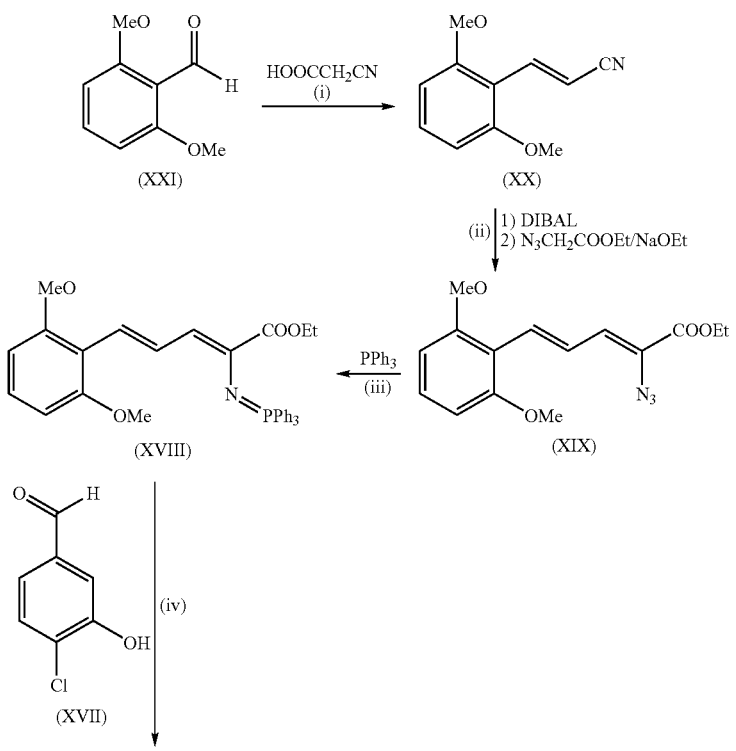
Scheme 3

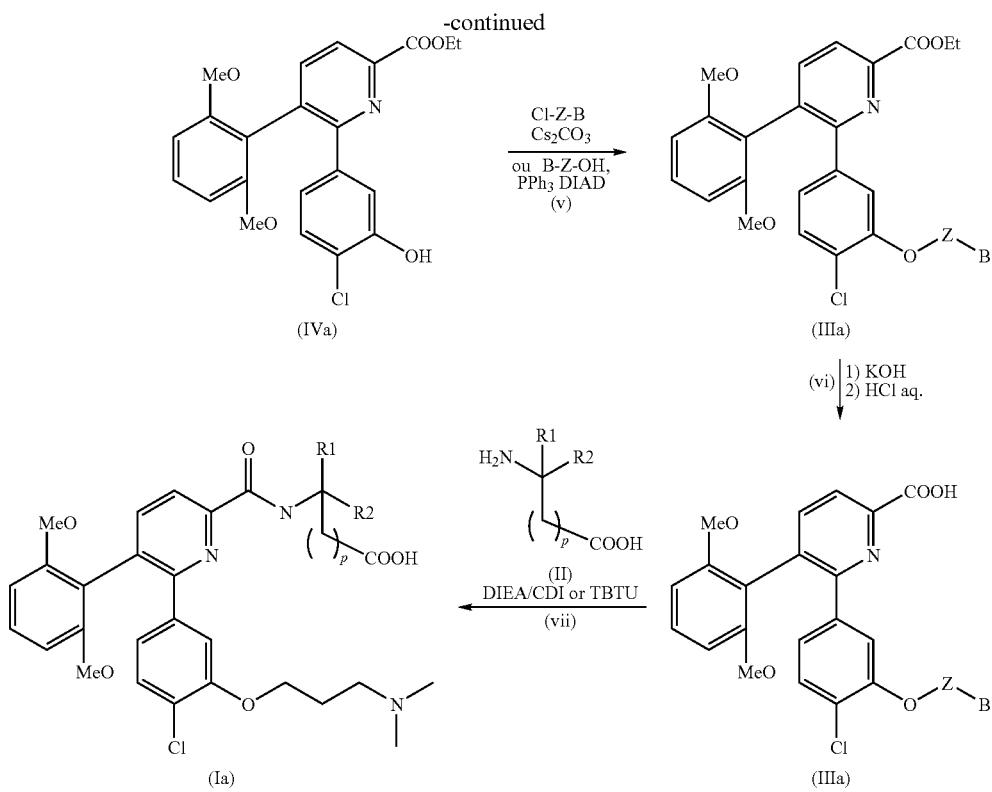

The following examples illustrate the preparation of some compounds according to the invention. The numbering of the compounds in the examples refers to the table given later showing the chemical structures and physical properties of some compounds according to the invention.

The Following Abbreviations are Used:
EtOAc Ethyl acetate
AcOH Acetic acid
BSA N,O-Bis(trimethylsilyl)acetamide
CDI Carbonyldiimidazole
CuI Copper iodide
DCM Dichloromethane
DIBAL-H Diisobutylaluminium hydride
DIAD Diisopropyl azodicarboxylate
DME Dimethoxyethane
DMF Dimethylformamide
DMSO Dimethyl sulphoxide
EDC.HCl N-[3-(Dimethylamino)propyl-N'-ethyl carbodiimide hydrochloride
EtOH Ethanol
h Hour(s)
HCl Hydrochloric acid
$K_2CO_3$ Potassium carbonate
KOAc Potassium acetate
$K_3PO_4$ Potassium phosphate or tripotassium tetraoxophosphate
$Na_2CO_3$ Sodium carbonate
$NH_4Cl$ Ammonium chloride
$NaHCO_3$ Sodium bicarbonate
$Na_2SO_4$ Sodium sulphate
NMP N-methylpyrrolidinone
$PdCl_2$ (dppf) [1,1'-bis(Cyclopentadienyldiphenylphosphino)ferrocene]palladium (II) dichloride
$Pd(PPh_3)_4$ Tetrakis(triphenylphosphine)palladium (0)
$Pd_2(dba)_3$ Tris(dibenzylideneacetone)dipalladium (0)
TBTU N-[(1H-Benzotriazol-1-yloxy)(dimethylamino)methylidene]-N-methylmethanaminium tetrafluoroborate
TEA Triethylamine
TFA Trifluoroacetic acid
THF Tetrahydrofuran
RT Room temperature

EXAMPLE 1

1-({[6-{4-Chloro-3-[3-(dimethylamino)propoxy]phenyl}-5-(2,6-dimethoxyphenyl)pyridin-2-yl]carbonyl}amino)cyclohexanecarboxylic acid (compound No. 12)

1.1. (2E)-3-(2,6-dimethoxyphenyl)acrylonitrile

Add, one after another, 1.13 g (14.7 mmol) of ammonium acetate, 40.4 mL (500 mmol) of pyridine and 31.2 g (367 mmol) of 2-cyanoacetic acid to a solution of 61 g (367 mmol) of 2,6-dimethoxybenzaldehyde in 360 mL of toluene. Reflux the reaction mixture for 15 h, distilling the toluene-water azeotrope in Dean-Stark apparatus. Take up the solution in 500 mL toluene and 40 mL pyridine and reflux again for 48 h in the Dean-Stark apparatus. After concentration under reduced pressure, take up the residue in 800 mL of dichloromethane (DCM) and wash successively with 1 L of 1N HCl aqueous solution, 500 mL of saturated aqueous solution of sodium carbonate ($Na_2CO_3$) and 1 L of water. After drying over sodium sulphate ($Na_2SO_4$) and concentration under reduced pressure, we obtain 62 g of (2E)-3-(2,6-dimethoxyphenyl)acrylonitrile in the form of brown oil, which is used "as is" in the next stage.

Yield=89%

1.2. (2E)-3-(2,6-dimethoxyphenyl)acrylaldehyde

Add 355 mL of a 1M solution of diisobutylaluminium hydride (DIBAL-H) (355 mmol) in toluene to a solution of 61 g (322 mmol) of (2E)-3-(2,6-dimethoxyphenyl)acrylonitrile in 600 mL of anhydrous toluene under argon and cooled to 0° C., maintaining the temperature at 0° C. Then bring the reaction mixture to room temperature (RT) and stir for 3 h. Then add 13 mL (322 mmol) of methanol and then, dropwise, 170 g (174 mmol) of an aqueous solution of sulphuric acid at 10 wt. %. Stir the suspension for one hour, then filter on a celite bed. Wash the filtrate with 500 mL of water then dry over $Na_2SO_4$ and concentrate under reduced pressure. Take up the residue obtained in 500 mL of DCM and filter in a silica column, eluting with DCM. After concentration under reduced pressure, we obtain 37 g of (2E)-3-(2,6-dimethoxyphenyl)acrylaldehyde in the form of colourless oil.
Yield=60%.

1.3. Ethyl (2E,4E)-2-azido-5-(2,6-dimethoxyphenyl) penta-2,4-dienoate

Add dropwise, while stirring, a solution of 37 g (192 mmol) of (2E)-3-(2,6-dimethoxyphenyl)acrylaldehyde and 85.7 g (664 mmol) of ethyl 2-azidoacetate in 200 mL of absolute ethanol EtOH to a solution of 15.5 g (673 mmol) of sodium in 500 mL of absolute EtOH cooled to −10° C. and kept under argon, maintaining the temperature at −10° C. After stirring at −10° C. for 3 h, stir the reaction mixture for 15 h at RT, then pour into 600 mL of an aqueous solution of ammonium chloride ($NH_4Cl$) at 30 wt. %. After filtration on a frit and rinsing with 2×200 mL of water, take up the precipitate in 600 mL of DCM, dry over $Na_2SO_4$ and concentrate under reduced pressure, which leads to 42 g of ethyl (2E,4E)-2-azido-5-(2,6-dimethoxyphenyl)penta-2,4-dienoate in the form of a yellow solid.
Yield=80%
M.p. (° C.)=138.

1.4 Ethyl (2E,4E)-5-(2,6-dimethoxyphenyl)-2-[(triphenylphosphoranylidene)amino]penta-2,4-dienoate Add, dropwise, a solution of 5 g of ethyl (2E,4E)-2-azido-5-(2,6-dimethoxyphenyl)penta-2,4-dienoate (16.5 mmol) in 60 mL of DCM to a solution of 4.37 g (16.7 mmol) of triphenylphosphine in 40 mL of DCM. Stir the reaction mixture for 2 h at RT, then concentrate under reduced pressure. Solidify the residue obtained in 100 mL of isopropyl ether, then filter on a frit and rinse with 50 mL of isopropyl ether, giving 7.9 g of ethyl (2E,4E)-5-(2,6-dimethoxyphenyl)-2-[(triphenylphosphoranylidene)amino]penta-2,4-dienoate in the form of a white solid.
Yield=91%
M.p. (° C.)=172

1.5. Ethyl 6-(4-chloro-3-hydroxyphenyl)-5-(2,6-dimethoxyphenyl)pyridine-2-carboxylate Reflux a solution of 7.54 g (14 mmol) of ethyl (2E,4E)-5-(2,6-dimethoxyphenyl)-2-[(triphenylphosphoranylidene)amino]penta-2,4-dienoate and 2.42 g (15.4 mmol) of 4-chloro-3-hydroxybenzaldehyde in 280 mL of anhydrous acetonitrile for 96 h. After cooling to RT, concentrate the reaction mixture under reduced pressure and purify the residue obtained by silica gel column chromatography, eluting with a cyclohexane/ethyl acetate (EtOAc) gradient from 0 to 30% of EtOAc. After concentration under reduced pressure, we obtain 2.4 g of ethyl 6-(4-chloro-3-hydroxyphenyl)-5-(2,6-dimethoxyphenyl)pyridine-2-carboxylate in the form of white powder.
Yield=41%
M.p. (° C.)=182

1.6. Ethyl 6-{4-chloro-3-[3-(dimethylamino)propoxy}phenyl)-5-(2,6-dimethoxyphenyl)pyridine-2-carboxylate Add 0.257 g (2.11 mmol) of 3-chloro-N,N-dimethylpropane-1-amine hydrochloride and 3.40 g (1.34 mmol) of caesium carbonate to a solution of 0.5 g (1.21 mmol) of ethyl 6-(4-chloro-3-hydroxyphenyl)-5-(2,6-dimethoxyphenyl)pyridine-2-carboxylate in 20 mL of anhydrous DMF under argon. Stir the reaction mixture for 15 min at RT then heat for 2 h at 80° C. After cooling to RT, add 1 mL of an aqueous solution of citric acid at 5% and concentrate the whole under reduced pressure. Take up the residue in 50 mL of EtOAc and wash with 10 mL of a 5% solution of $Na_2CO_3$ and then 10 mL of water. After drying over $Na_2SO_4$ and concentration under reduced pressure, purify the residue by silica gel column chromatography, eluting with a DCM/methanol gradient from 1 to 15% of methanol. After concentration under reduced pressure, we obtain 0.55 g of ethyl 6-{4-chloro-3-[3-(dimethylamino)propoxy]phenyl}-5-(2,6-dimethoxyphenyl)pyridine-2-carboxylate in the form of oil.
Yield=91%

1.7. 6-{4-Chloro-3-[3-(dimethylamino)propoxy]phenyl}-5-(2,6-dimethoxyphenyl)pyridine-2-carboxylic acid Add 3.16 g (56.38 mmol) of potassium hydroxide to a solution of 5.63 g (11.28 mmol) of ethyl 6-{4-chloro-3-[3-(dimethylamino)propoxy]phenyl}-5-(2,6-dimethoxyphenyl)pyridine-2-carboxylate in 132 mL of EtOH. Reflux the reaction mixture for 2 h and then concentrate under reduced pressure. Take up the residue obtained in 10 mL of water, then neutralize with 56.5 mL (56.5 mmol) of a 1N HCl aqueous solution. The precipitate obtained is filtered on a frit and rinsed with 2×10 mL of water. After drying under reduced pressure, we obtain 5.25 g of 6-{4-chloro-3-[3-(dimethylamino)propoxy]phenyl}-5-(2,6-dimethoxyphenyl)pyridine-2-carboxylic acid in the form of white powder.
Yield=100%
M.p. (° C.)=215

1.8. 1-({[6-{4-Chloro-3-[3-(dimethylamino)propoxy]phenyl}-5-(2,6-dimethoxyphenyl)pyridin-2-yl]carbonyl}amino)cyclohexanecarboxylic acid Add, under argon, 0.74 mL (0.41 mmol) of diisopropylethylamine and 409 mg (1.28 mmol) of TBTU to a solution of 200 mg (0.42 mmol) of 6-{4-chloro-3-[3-(dimethylamino)propoxy]phenyl}-5-(2,6-dimethoxyphenyl)pyridine-2-carboxylic acid in 50 mL of anhydrous DMF. In parallel, heat, while stirring under argon, a mixture of 84 mg (0.59 mmol) of 2-aminocyclohexane-2-carboxylic acid and 0.18 mL (0.76 mmol) of N,O-bis(trimethylsilyl)acetamide (BSA) in 5 mL of anhydrous acetonitrile to 90° C. After 2 h, the mixture has dissolved completely. Cool the solution to RT, then add it to the solution of 6-{4-chloro-3-[3-(dimethylamino)propoxy]phenyl}-5-(2,6-dimethoxyphenyl)pyridine-2 carboxylic acid activated with TBTU. After stirring for 18 h at RT, add 10 mL of 0.5N HCl aqueous solution and continue stirring for 3 h. Then distribute the reaction mixture in a mixture of 20 mL of EtOAc/ether 1:1 and 10 mL of water. After extraction, extract the aqueous phase again with 10 mL of 1:1 ether/EtOAc mixture. Combine the organic phases, wash with 2×10 mL of water, dry over $Na_2SO_4$ and concentrate under reduced pressure. Then purify the residue by reverse-phase HPLC (RP18) eluting with a 0.01N HCl/acetonitrile gradient from 5% to 100% of acetonitrile. After concentration under reduced pressure and tyophilization, we obtain 106 mg of 1-({[6-{4-chloro-3-[3-(dimethylamino)propoxy]phenyl}-5-(2,6-dimethoxyphenyl)pyridin-2-yl]carbonyl}amino)cyclohexanecarboxylic acid hydrochloride in the form of white powder.

Yield=41%
M.p. (° C.)>200.
$M=C_{32}H_{38}ClN_3O_6=595$; M+H=596
$^1$H NMR (ppm, d6-DMSO, 400 MHz): 8.70 (s, 1H); 7.80 (d, 1H); 7.65 (d, 1H) 7.15 (m, 2H); 7.05 (d, 1H); 6.60 (d, 1H); 6.50 (d, 2H); 3.85 (t, 2H); 3.35 (s, 6H); 2.75 (m, 2H); 2.45 (s, 6H); 2.15 (m, 2H); 1.90 (m, 2H) 1.55 (m, 4H); 1.25 (m, 4H).

EXAMPLE 2

9-({[6-{4-Chloro-3-[3-(dimethylamino)propoxy]phenyl}-5-(2,6-dimethoxyphenyl)pyridin-2-yl]carbonyl}amino)bicyclo[3.3.1]nonane-9-carboxylic acid hydrochloride (compound No. 25)

2.1. 9-aminobicyclo[3.3.1.]nonane-9-carbonitrile

Add successively 21 mL of water, 1.12 g (22.8 mmol) of sodium cyanide, 4.52 mL (54.27 mmol) of 12N aqueous ammonia solution and 2.32 g (43.41 mmol) of $NH_4Cl$ to a solution of 3 g (21.7 mmol) of bicyclo[3.3.1.]nonan-9-one in 40 mL of EtOH. Stir the reaction mixture for 18 h at 50° C. Then add 5 mL of 12N aqueous ammonia solution and heat the mixture again for 4 h at 50° C. Cool the solution to RT then distribute in 100 mL of a 1:1 mixture of ether/1N aqueous soda solution. After extraction, wash the organic phase with 3×50 mL of water, dry over $Na_2SO_4$ and concentrate under reduced pressure. Take up the residue obtained in 50 mL of ether and then treat for 1 minute with a gentle stream of hydrogen chloride. Filter the hydrochloride thus obtained, wash with 20 mL of ether and distribute in 100 mL of a 1:1 mixture of DCM/saturated aqueous solution of $Na_2CO_3$. Extract the aqueous phase again with 50 mL of DCM, then combine the organic phases, wash with 2×20 mL of water and dry over $Na_2SO_4$. After concentration under reduced pressure, we obtain 1.88 g of 9-aminobicyclo[3.3.1.]nonane-9-carbonitrile in the form of oil.

Yield=52%

2.2. N-(9-cyanobicyclo[3.3.1]non-9-yl)benzamide

Add a solution of 2.37 g (17.17 mmol) of potassium carbonate in 30 mL of water, then 1.37 mL (11.8 mmol) of benzoyl chloride, to a solution of 1.88 g (11.45 mmol) of 9-aminobicyclo[3.3.1]nonane-9-carbonitrile in 20 mL of THF. Stir the reaction mixture for 1 h at RT, then distribute in 100 mL of a 1:1 mixture of DCM/water. Wash the organic phase with 50 mL of water, dry over $Na_2SO_4$ and concentrate under reduced pressure. Solidify the residue obtained in 100 mL of pentane giving, after filtration and washing with pentane, 2.81 g of N-(9-cyanobicyclo[3.3.1]non-9-yl)benzamide in the form of white powder.

Yield=92%
M.p. (° C.)>200

2.3. 9-Aminobicyclo[3.3.1.]nonane-9-carboxylic acid

Add 200 mL of a 12N HCl aqueous solution to a solution of 2.8 g (10.43 mmol) of N-(9-cyanobicyclo[3.3.1]non-9-yl)benzamide in 80 mL of THF. Stir the solution for 20 h at RT—a white precipitate gradually appears. After filtering the precipitate on a frit and rinsing with 3×200 mL of water, we obtain 3.6 g of wet 9-benzoylamino bicyclo[3.3.1]nonane-9-carboxylic acid.

Dissolve 3 g (10.44 mmol) of 9-benzoylamino bicyclo[3.3.1]nonane-9-carboxylic acid in 200 mL of AcOH and 50 mL of 6N HCl aqueous solution, reflux the mixture for 18 h and then concentrate partially by distillation of 150 mL of solvent. After cooling, filter the reaction mixture and distribute in 150 mL of a 1:2 mixture of 1N HCl aqueous solution/ether. After extraction, concentrate the aqueous phase and then treat it dropwise with a 12N aqueous solution of soda (NaOH) to adjust the pH to 5-6. Filter the amino acid thus precipitated, wash with 3×50 mL of water and dry under reduced pressure, which gives 1.88 g of 9-aminobicyclo[3.3.1]nonane-9-carboxylic acid in the form of white crystals.

Yield=98%
M.p. (° C.)>250.

2.4. 9-({[6-{4-Chloro-3-[3-(dimethylamino)propoxy]phenyl}-5-(2,6-dimethoxyphenyl)pyridin-2-yl]carbonyl}amino)bicyclo[3.3.1]nonane-9-carboxylic acid hydrochloride According to the method described in example 1.8, starting from 400 mg (0.85 mmol) of 6-{4-chloro-3-[3-(dimethylamino)propoxy]phenyl}-5-(2,6-dimethoxyphenyl)pyridine-2-carboxylic acid and 218 mg (1.19 mmol) of 9-aminobicyclo[3.3.1]nonane-9-carboxylic acid and after reverse-phase purification and lyophilization, we obtain 220 mg of 9-({[6-{4-chloro-3-[3-(dimethylamino)propoxy]phenyl}-5-(2,6-dimethoxyphenyl)pyridin-2-yl]carbonyl}amino)bicyclo[3.3.1]nonane-9-carboxylic acid hydrochloride in the form of white powder.

Yield=41%
M.p. (° C.): 197
$M=C_{35}H_{42}ClN_3O_6=635$; M+H=636
$^1$H NMR (ppm, d6-DMSO, 400 MHz): 8.45 (s, 1H); 8.00 (d, 1H); 7.80 (d, 1H); 7.30 (t, 2H); 7.25 (s, 1H); 7.05 (d, 1H); 6.95 (dd, 1H); 6.70 (d, 1H); 3.85 (t, 2H); 3.50 (s, 6H); 3.05 (m, 2H); 2.70 (s, 6H); 2.2-1.4 (m, 16H).

EXAMPLE 3

2-({[6-{4-Chloro-3-[(1-methylpyrrolidin-3-yl)oxy]phenyl}-5-(2,6-dimethoxyphenyl)pyridin-2-yl]carbonyl}amino)adamantane-2-carboxylic acid hydrochloride (compound No. 15)

3.1. Ethyl 6-{4-chloro-3-[(1-methylpyrrolidin-3-yl)oxy]phenyl}-5-(2,6-dimethoxyphenyl)pyridine-2-carboxylate Add 88 mg (0.87 mmol) of 1-methyl-3-hydroxypyrrolidine, 246 mg (1.09 mmol) of triphenylphosphine and 0.01 mL (0.07 mmol) of TEA to a solution of 300 mg (0.72 mmol) of ethyl 6-(4-chloro-3-hydroxyphenyl)-5-(2,6-dimethoxyphenyl)pyridine-2-carboxylate in 2.5 mL of anhydrous THF cooled to 0° C. and placed under argon. After dissolution, add dropwise, at 0° C., a solution of 0.24 mL (1.09 mmol) of DIAD in 2.5 mL of anhydrous THF. Bring the reaction mixture to RT, stir for 18 h, then take up in 50 mL of EtOAc. Wash the organic phase successively with 20 mL of a saturated aqueous solution of sodium bicarbonate (NaHCO$_3$) then 20 mL of water. After drying over Na$_2$SO$_4$ and concentration under reduced pressure, purify the residue obtained by silica gel column chromatography, eluting with a DCM/methanol gradient from 0 to 20% of methanol. After concentration under reduced pressure, we obtain 250 mg of ethyl 6-{4-chloro-3-[(1-methylpyrrolidin-3-yl)oxy]phenyl}-5-(2,6-dimethoxyphenyl)pyridine-2-carboxylate in the form of oil.
Yield=70%

3.2. 2-({[6-{4-Chloro-3-[(1-methylpyrrolidin-3-yl)oxy]phenyl}-5-(2,6-dimethoxyphenyl)pyridin-2-yl]carbonyl}amino)adamantane-2-carboxylic acid hydrochloride According to the saponification/peptide coupling steps described in examples 1.7 and 1.8 respectively, starting from 250 mg (0.5 mmol) of ethyl 6-{4-chloro-3-[(1-methylpyrrolidin-3-yl)oxy]phenyl}-5-(2,6-dimethoxyphenyl)pyridine-2-carboxylate and 100 mg (0.51 mmol) of 2-aminoadamantane-2-carboxylic acid, we obtain 160 mg of 2-({[6-{4-chloro-3-[2-(dimethylamino)ethoxy]phenyl}-5-(2,6-dimethoxyphenyl)pyridin-2-yl]carbonyl}amino)adamantane-2-carboxylic acid in the form of white powder.
Yield=47%
M.p. (° C.)=215
M=C$_{36}$H$_{40}$ClN$_3$O$_6$=645; M+H=646
$^1$H NMR (ppm, d6-DMSO, 400 MHz): 8.40 (s, 1H); 8.00 (d, 1H); 7.85 (d, 1H); 7.35 (m, 2H); 7.05 (dd, 1H); 6.95 (t, 1H); 6.65 (d, 2H); 4.90 (m, 1H); 3.80 (m, 2H); 3.50 (s, 6H); 3.15 (m, 2H); 2.85 (m, 3H); 2.55 (s, 2H); 2.2-1.6 (m, 14H).

EXAMPLE 4

2-({[6-{4-Chloro-3-[3-(dimethylamino)propoxy]phenyl}-5-(2-methylphenyl)pyridin-2-yl]carbonyl}amino)adamantane-2-carboxylic acid hydrochloride (compound No. 18)

Methyl 6-bromo-5-hydroxy-2-pyridine carboxylate is synthesized according to a method already described in the literature (*J. Org. Chem.*, 1996, 4623-4633).

4.1. 2-(benzyloxy)-1-chloro-4-iodobenzene

A suspension of 300 g (1179 mmol) of 2-chloro-5-iodophenol and 140 mL (1179 mmol) of benzyl bromide and 195.5 g (1415 mmol) of anhydrous potassium carbonate, in 1.2 L of anhydrous DMF is stirred for 5 h at 70° C. and then cooled to RT. The reaction mixture is then distributed in 3 L of a 2:1 ether/water mixture. The organic phase is washed with 2×1 L of water, dried over Na$_2$SO$_4$, concentrated under reduced pressure and the residue obtained is solidified in pentane. We thus obtain 376 g of 2-(benzyloxy)-1-chloro-4-iodobenzene in the form of beige powder.
Yield=92%
M.p. (° C.)=72.

4.2. [3-(Benzyloxy)-4-chlorophenyl]boronic acid

Add dropwise 374 mL (748 mmol) of a solution of iPrMgCl 2N in THF to a solution of 198 g (575 mmol) of 2-(benzyloxy)-1-chloro-4-iodobenzene in 1.2 L of anhydrous THF under argon and stirred at −50° C., maintaining the temperature between −40 and −50° C. Allow the reaction mixture to return to −10° C. and continue stirring for 1 h. Then add 172 mL (748 mmol) of triisopropyl borate and leave the reaction mixture to return slowly to RT. After stirring for 2 h, treat the mixture with 1 L of aqueous solution of HCl 5N, then extract with ether (2×600 mL). Wash the organic phase with 2×1 L of water, dry over Na$_2$SO$_4$ then concentrate under reduced pressure. Solidify the residue obtained in pentane, filter on a frit and wash with pentane. We thus obtain 113 g of [3-(benzyloxy)-4-chlorophenyl]boronic acid in the form of a white solid.
Yield=76%
M.p. (° C.)=148 (decomposition).

4.3. Methyl 6-[3-(benzyloxy)-4-chlorophenyl]-5-hydroxypyridine-2-carboxylate Stir a solution of 37 g (163 mmol) of methyl 6-bromo-5-hydroxy-2-pyridine carboxylate and 51 g (196 mmol) of [3-(benzyloxy)-4-chlorophenyl]boronic acid in 300 mL of anhydrous DMF for 15 min while bubbling with argon, then add 63.8 g (196 mmol) of anhydrous caesium carbonate and 5 g (4.33 mmol) of Pd(PPh$_3$)$_4$. Stir the reaction mixture for 10 h at 90° C. under argon, cool to RT, then distribute in 1 L of ether/EtOAc 1:1 mixture and 1 L of a 0.5N aqueous HCl solution. Extract the aqueous phase again with 500 mL of EtOAc/ether 1:1 mixture. Combine the organic phases and wash with 4×500 mL of water. After drying over Na$_2$SO$_4$ and concentration under reduced pressure, take up the precipitate with 500 mL of a 7:3 mixture of pentane/DCM, filter and wash with pentane. We thus obtain 32 g of methyl 6-[3-(benzyloxy)-4-chlorophenyl]-5-hydroxypyridine-2-carboxylate in the form of yellow ochre powder.
Yield=53%
M.p. (° C.)=202

4.4. Methyl 6-[3-(benzyloxy)-4-chlorophenyl]-5-{[(trifluoromethyl)sulphonyl]oxy}pyridine-2-carboxylate Add 17.7 mL (126 mmol) of TEA to a mixture of 38.8 g (105 mmol) of methyl 6-[3-(benzyloxy)-4-chlorophenyl]-5-hydroxypyridine-2-carboxylate in 200 mL of DCM. The mixture dissolves gradually and is cooled to −5° C. under argon. Add, dropwise, 19.42 mL (115.4 mmol) of trifluoromethanesulphonic anhydride, maintaining the temperature at 0° C. After 3 h at 0° C., take up the reaction mixture in 300 mL of DCM and wash with 2×200 mL of water, dry over Na$_2$SO$_4$, then concentrate under reduced pressure. Purify the residue obtained by chromatography on a silica column, eluting with a pentane/EtOAc gradient from 0 to 30% of EtOAc. After concentration under reduced pressure, we obtain 47.5 g of methyl 6-[3-(benzyloxy)-4-chlorophenyl]-5-{[(trifluoromethyl)sulphonyl]oxy}pyridine-2-carboxylate in the form of white crystals.
Yield=90%
M.p. (° C.)=89.

4.5. Methyl 6-[3-(benzyloxy)-4-chlorophenyl]-5-(2-methylphenyl)pyridine-2-carboxylate Stir a solution of 25 g (48.8 mmol) of methyl 6-[3-(benzyloxy)-4-chlorophenyl]-5-{[(trifluoromethyl)sulphonyl]oxy}pyridine-2-carboxylate and 8.8 g (64.8 mmol) of 2-methylphenylboronic acid in 200 mL of anhydrous DMF for 15 min while bubbling with argon, then add 12.7 g (60 mmol) of anhydrous potassium phosphate ($K_3PO_4$) and 5.76 g (5 mmol) of $Pd(PPh_3)_4$ and stir the reaction mixture for 18 h at 90° C. under argon. Then distribute the reaction mixture at RT in 600 mL of ether/EtOAc 1:1 mixture and 600 ml of water. After extraction, extract the aqueous phase again with 100 mL of EtOAc, combine the organic phases and wash with 4×300 mL of water, dry over $Na_2SO_4$, then concentrate under reduced pressure. Purify the residue obtained by silica gel column chromatography, eluting with a heptane/EtOAc gradient from 0 to 20% of EtOAc. After concentration under reduced pressure, we obtain 18 g of methyl 6-[3-(benzyloxy)-4-chlorophenyl]-5-(2-methylphenyl)pyridine-2-carboxylate in the form of oil.

Yield=81%

4.6. Methyl 6-(4-chloro-3-hydroxyl]phenyl)-5-(2-methylphenyl)pyridine-2-carboxylate Add dropwise, in 1 h 30 min, 85.6 mL (85.6 mmol) of a 1N solution of boron tribromide in DCM to a solution of 19 g (42.8 mmol) of methyl 6-[3-(benzyloxy)-4-chlorophenyl]-5-(2-methylphenyl)pyridine-2-carboxylate in 70 mL of anhydrous DCM cooled under argon to −70° C., maintaining the temperature at −65° C. After stirring for 2 h at −70° C., add dropwise 20 mL (520 mmol) of anhydrous methanol, maintaining the temperature at −65° C. Bring the reaction mixture to RT, then concentrate under reduced pressure. Take up the residue in 100 mL of toluene and concentrate again. Repeat the operation two more times. Take up the residue obtained in 100 mL of methanol and cool under argon at 0° C., then add dropwise 9 mL (128 mmol) of thionyl chloride. Stir the reaction mixture for 48 h at RT, then concentrate under reduced pressure. Take up the residue obtained in 200 mL of EtOAc, cool to 0° C. and treat with 300 mL of a saturated aqueous solution of $NaHCO_3$. After extraction, extract the aqueous phase again with 100 mL of EtOAc. Combine the organic phases, wash with 100 mL of water, dry over $Na_2SO_4$ and concentrate under reduced pressure. Purify the residue by silica gel column chromatography, eluting with a heptane/EtOAc gradient from 0 to 30% of EtOAc. After concentration under reduced pressure, we obtain 14.7 g of methyl 6-(4-chloro-3-hydroxyphenyl)-5-(2-methylphenyl)pyridine-2-carboxylate in the form of white powder.

Yield=97%

M.p. (° C.)=190

4.7. Methyl 6-{4-chloro-3-[3-(dimethylamino)propoxy]phenyl}-5-(2-methylphenyl)pyridine-2-carboxylate According to the method described in example 1.6, starting from 5.4 g (15.26 mmol) of methyl 6-(4-chloro-3-hydroxyphenyl)-5-(2-methylphenyl)pyridine-2-carboxylate, 9.95 g (30.53 mmol) of caesium carbonate and 2.9 g (18.3 mmol) of 3-chloro-N,N-dimethylpropan-1-amine hydrochloride in 60 mL of DMF, we obtain 6 g of methyl 6-{4-chloro-3-[3-(dimethylamino)propoxy]phenyl}-5-(2-methylphenyl)pyridine-2-carboxylate in the form of oil.

Yield=90%

4.8. 2-({[6-{4-Chloro-3-[3-(dimethylamino)propoxy]phenyl}-5-(2-methylphenyl)pyridin-2-yl]carbonyl}amino)adamantane-2-carboxylic acid hydrochloride According to the saponification/peptide coupling steps described in examples 1.7 and 1.8 respectively, starting from 4.65 g (10.6 mmol) of methyl 6-{4-chloro-3-[3-(dimethylamino)propoxy]phenyl}-5-(2-methylphenyl)pyridine-2-carboxylate and 2.38 g (12.18 mmol) of 2-aminoadamantane-2-carboxylic acid, we obtain 4.1 g of 2-({[6-{4-chloro-3-[3-(dimethylamino)propoxy]phenyl}-5-(2-methylphenyl)pyridin-2-yl]carbonyl}amino)adamantane-2-carboxylic acid hydrochloride in the form of white powder.

Yield=54%

M.p. (° C.): 224.

$M=C_{35}H_{40}ClN_3O_4=601$; M+H=602

$^1$H NMR (ppm, d6-DMSO, 400 MHz): 8.50 (s, 1H); 8.05 (d, 1H); 7.90 (d, 1H); 7.25 (m, 5H); 7.10 (dd, 1H); 6.95 (dd, 1H); 3.80 (m, 2H); 3.1 (m, 2H); 2.75 (s, 6H); 2.60 (s, 2H); 1.90 (s, 3H); 2.2-1.6 (m, 14H).

EXAMPLE 5

2-({[6-{4-Chloro-3-[3-(dimethylamino)propoxy]phenyl}-5-(2-oxopyrrolidin-1-yl)pyridin-2-yl]carbonyl}amino)adamantane-2-carboxylic acid hydrochloride (compound No. 23)

5.1. Methyl 6-[3-(benzyloxy)-4-chlorophenyl]-5-(2-oxopyrrolidin-1-yl)pyridine-2-carboxylate Stir a solution of 500 mg (1 mmol) of methyl 6-[3-(benzyloxy)-4-chlorophenyl]-5-{[(trifluoromethyl)sulphonyl]oxy}pyridine-2-carboxylate, 0.1 mL (1.1 mmol) of 2-pyrrolidinone and 450 mg (1.4 mmol) of caesium carbonate in 10 mL of anhydrous 1,4-dioxan for 10 minutes while bubbling with argon, then add 9 mg (0.01 mmol) of $Pd_2(dba)_3$ and 17 mg (0.03 mmol) of Xantphos and heat the reaction mixture for 6 h at 70° C. while stirring. Then distribute the mixture in 100 mL of ether/EtOAc 1:1 mixture and 50 mL of a saturated aqueous solution of $NH_4Cl$. After extraction, wash the organic phase with 2×50 mL of water, dry over $Na_2SO_4$ and concentrate under reduced pressure. Purify the residue obtained by silica gel column chromatography, eluting with a heptane/EtOAc gradient from 0 to 30% of EtOAc. After concentration under reduced pressure, we obtain 293 mg of methyl 6-[3-(benzyloxy)-4-chlorophenyl]-5-(2-oxopyrrolidin-1-yl)pyridine-2-carboxylate in the form of oil.

Yield=67%.

5.2. Methyl 6-{4-chloro-3-[3-(dimethylamino)propoxy]phenyl}-5-(2-oxopyrrolidin-1-yl)pyridine-2-carboxylate According to the debenzylation/O-alkylation steps described in examples 4.6 and 1.6 respectively, starting from 511 mg (1.17 mmol) of methyl 6-[3-(benzyloxy)-4-chlorophenyl]-5-(2-oxopyrrolidin-1-yl)pyridine-2-carboxylate, we obtain 391 mg of methyl 6-{4-chloro-3-[3-(dimethylamino)propoxy]phenyl}-5-(2-oxopyrrolidin-1-yl)pyridine-2-carboxylate in the form of oil.

Yield=77%

5.3. 2-({[6-{4-Chloro-3-[3-(dimethylamino)propoxy]phenyl}-5-(2-oxopyrrolidin-1-yl)pyridin-2-yl]carbonyl}amino)adamantane-2-carboxylic acid hydrochloride According to the saponification/peptide coupling steps described in examples 1.7 and 1.8 respectively, starting from 391 mg (0.91 mmol) of methyl 6-{4-chloro-3-[3-(dimethylamino)propoxy]phenyl}-5-(2-oxopyrrolidin-1-yl)pyridine-2-carboxylate and 265 mg (1.36 mmol) of 2-aminoadamantane-2-carboxylic acid, we obtain 241 mg of 2-({[6-{4-chloro-3-[3-(dimethylamino)propoxy]phenyl}-5-(2-oxopyrrolidin-1-yl)pyridin-2-yl]carbonyl}amino) adamantane-2-carboxylic acid hydrochloride in the form of white powder.

Yield=39%
M.p. (° C.): 199
M=$C_{32}H_{39}ClN_4O_5$=594; M+H=595
$^1$H NMR (ppm, d6-DMSO, 400 MHz): 8.40 (s, 1H); 8.05 (t, 2H); 7.55 (d, 1H); 7.50 (s, 1H); 7.20 (dd, 1H); 4.15 (t, 2H); 3.65 (t, 2H); 2.75 (s, 6H); 2.55 (s, 2H); 2.2-1.6 (m, 20H).

EXAMPLE 6

2-{[(2'-{4-Chloro-3-[3-(dimethylamino)propoxy] phenyl}-2,3'-bipyridin-6'-yl)carbonyl] amino}adamantane-2-carboxylic acid hydrochloride (compound No. 27)

6.1. Methyl 2'-[3-(benzyloxy)-4-chlorophenyl]-2,3'-bipyridine-6'-carboxylate Stir a suspension of 0.5 g (1 mmol) of methyl 6-[3-(benzyloxy)-4-chlorophenyl]-5-{[(trifluoromethyl)sulphonyl] oxy}pyridine-2-carboxylate, 0.44 g (1.2 mmol) of 2-tri-n-butylstannylpyridine and 42 mg (1 mmol) of anhydrous lithium chloride in 2 mL of anhydrous DMF for 10 min while bubbling with argon, then add 9.5 mg (0.05 mmol) of CuI, 45 mg (0.05 mmol) of Pd$_2$(dba)$_3$ and 27 mg (0.05 mmol) of PdCl$_2$ (dppf) and then heat the reaction mixture to 90° C. After stirring for 5 h at 90° C., cool the mixture to RT, take up in 30 ml of EtOAc, treat and stir for 15 minutes with 30 mL of a 5 wt. % aqueous solution of potassium fluoride. Then filter the two-phase mixture on a bed of celite, and rinse the celite with 30 mL of EtOAc. Wash the organic phase with 4×60 mL of water, dry over Na$_2$SO$_4$ and concentrate at reduced pressure. Purify the residue obtained by chromatography on a silica column, eluting with a toluene/EtOAc gradient from 0 to 15% of EtOAc. After concentration under reduced pressure, we obtain 240 mg of methyl 2'-[3-(benzyloxy)-4-chlorophenyl]-2,3'-bipyridine-6'-carboxylate in the form of oil.

Yield=55%

6.2. Methyl 2'-{4-chloro-3-[3-(dimethylamino)propoxy]phenyl}-2,3'-bipyridine-6'-carboxylate According to the debenzylation/O-alkylation steps described in examples 4.6 and 1.6 respectively, starting from 680 mg (1.58 mmol) of methyl 2'-[3-(benzyloxy)-4-chlorophenyl]-2,3'-bipyridine-6'-carboxylate, we obtain 580 mg of methyl 2'-{4-chloro-3-[3-(dimethylamino)propoxy]phenyl}-2,3'-bipyridine-6'-carboxylate in the form of oil.

Yield=86%

6.3. 2-{[(2'-(4-Chloro-3-[3-(dimethylamino)propoxy]phenyl}-2,3'-bipyridin-6'-yl)carbonyl] amino}adamantane-2-carboxylic acid hydrochloride According to the saponification/peptide coupling steps described in examples 1.7 and 1.8 respectively, starting from 581 mg (1.36 mmol) of methyl 2'-{4-chloro-3-[3-(dimethylamino)propoxy]phenyl}-2,3'-bipyridine-6'-carboxylate and 365 mg (1.87 mmol) of 2-aminoadamantane-2-carboxylic acid, we obtain 435 mg of 2-{[(2'-{4-chloro-3-[3-(dimethylamino)propoxy]phenyl}-2,3'-bipyridin-6'-yl)carbonyl] amino}adamantane-2-carboxylic acid hydrochloride in the form of white powder.

Yield=48%
M.p. (° C.): 209
M=$C_{33}H_{37}ClN_4O_4$=588; M+H=589
$^1$H NMR (ppm, d6-DMSO, 400 MHz): 10.55 (s, 1H); 8.65 (s, 1H); 8.50 (s, 1H); 8.25 (d, 1H); 8.10 (d, 1H); 7.80 (t, 1H); 7.40 (dd, 1H); 7.35 (d, 2H); 7.25 (s, 1H); 6.80 (d, 1H); 3.95 (t, 2H); 3.15 (m, 2H); 2.75 (s, 3H); 2.70 (s, 3H); 2.60 (s, 2H); 2.2-1.6 (m, 14H).

EXAMPLE 7

2-({[6-{4-Chloro-3-[3-(dimethylamino)propoxy] phenyl}-5-(2-chlorophenyl)pyridin-2-yl] carbonyl}amino)adamantane-2-carboxylic acid hydrochloride (compound No. 22)

7.1. Methyl 6-{4-chloro-3-[3-(dimethylamino)propoxy]phenyl}-5-(2-chlorophenyl)pyridine-2-carboxylate According to the debenzylation/O-alkylation steps described in examples 4.6 and 1.6 respectively, starting from 625 mg (1.35 mmol) of methyl 6-[3-(benzyloxy)-4-chlorophenyl]-5-(2-chlorophenyl)pyridine-2-carboxylate, we obtain 173 mg of methyl 6-{4-chloro-3-[3-(dimethylamino)propoxy]phenyl}-5-(2-chlorophenyl)pyridine-2-carboxylate in the form of oil.

Yield=28%

7.2. 2-({[6-{4-Chloro-3-[3-(dimethylamino)propoxy]phenyl}-5-(2-chlorophenyl)pyridin-2-yl] carbonyl}amino)adamantane-2-carboxylic acid hydrochloride According to the saponification/peptide coupling steps described in examples 1.7 and 1.8 respectively, starting from 290 mg (0.63 mmol) of methyl 6-{4-chloro-3-[3-(dimethylamino)propoxy]phenyl}-5-(2-chlorophenyl)pyridine-2-carboxylate and 184 mg (0.94 mmol) of 2-aminoadamantane-2-carboxylic acid, we obtain 120 mg of 2-({[6-{4-chloro-3-[3-(dimethylamino)propoxy]phenyl}-5-(2-chlorophenyl) pyridin-2-yl]carbonyl}amino)adamantane-2-carboxylic acid hydrochloride in the form of white powder.

Yield=29%
M.p. (° C.): 214
M=$C_{34}H_{37}Cl_2N_3O_4$=621; M+H=622
$^1$H NMR (ppm, d6-DMSO, 400 MHz): 8.50 (s, 1H); 8.10 (d, 1H); 8.00 (d, 1H); 7.45 (m, 2H); 7.40 (d, 2H); 7.35 (d, 1H); 7.20 (dd, 1H); 6.90 (dd, 1H); 3.90 (m, 2H); 3.15 (m, 2H); 2.75 (s, 6H); 2.60 (s, 2H); 2.2-1.6 (m, 14H).

EXAMPLE 8

1-({[6-{4-Chloro-3-[3-(dimethylamino)propoxy] phenyl}-5-(2-methylphenyl)pyridin-2-yl] carbonyl}amino)cyclohexanecarboxylic acid hydrochloride (compound No. 34)

According to the saponification/peptide coupling steps described in examples 1.7 and 1.8 respectively, starting from 465 mg (1.06 mmol) of methyl 6-{4-chloro-3-[3-(dimethylamino)propoxy]phenyl}-5-(2-methylphenyl)pyridine-2-carboxylate (example 4.7) and 174 mg (1.22 mmol) of 2-aminocyclohexane-2-carboxylic acid, we obtain 330 mg of 1-({[6-{4-chloro-3-[3-(dimethylamino)propoxy]phenyl}-5-(2- methylphenyl)pyridin-2-yl]carbonyl}amino) cyclohexanecarboxylic acid hydrochloride in the form of white powder.
Yield=53%
M.p. (° C.)=146-150
M=$C_{31}H_{36}ClN_3O_4$=549; M+H=550
$^1$H NMR (ppm, d6-DMSO, 400 MHz): 10.5 (s, 1H); 8.40 (s, 1H); 8.05 (d, 1H); 7.90 (d, 1H); 7.35 (d, 1H); 7.25 (m, 5H); 7.05 (dd, 1H); 3.80 (m, 2H); 3.1 (m, 2H); 2.75 (s, 6H); 1.75 (s, 3H); 2.2-1.6 (m, 12H).

EXAMPLE 9 cis-1-({[6-{4-Chloro-3-[3-(diethylamino)propoxy]phenyl}-5-(2-methylphenyl)pyridin-2-yl]carbonyl}amino)-4-hydroxycyclohexane carboxylic acid hydrochloride (compound No. 147)

Add successively, under argon and at RT, 127 mg (1.1 mmol) of N-hydroxysuccinimide and 211 mg (1.1 mmol) of EDC.HCl to a mixture of 490 mg (1 mmol) of 6-{4-chloro-3-[3-(diethylamino)propoxy]phenyl}-5-(2-methylphenyl) pyridine-2-carboxylic acid hydrochloride in 5 mL of anhydrous DMF. After stirring for 18 h, add successively to the (bright yellow, clear) reaction mixture, 0.9 mL (5.4 mmol) of DIEA and 215 mg (1.1 mmol) of cis-1-amino-4-hydroxycyclohexane carboxylic acid (*J. Chem. Soc, Perkin Trans.* 1 (1999) pp. 3375-3379). Continue stirring for 18 h at RT, then concentrate the reaction mixture under reduced pressure. Then treat the residue obtained for 18 h at RT with 7 mL (7 mmol) of 1N HCl, then concentrate under reduced pressure. Purify the residue by HPLC on a column of RP18, eluting with a $10^{-2}$N HCl/acetonitrile gradient from 0% to 100% of acetonitrile. After lyophilization, we obtain 350 mg of cis-1-({[6-{4-chloro-3-[3-(diethylamino)propoxy]phenyl}-5-(2-methylphenyl)pyridin-2-yl]carbonyl}amino)-4-hydroxycyclohexane carboxylic acid hydrochloride in the form of white powder.
Yield=55%
M.p. (° C.)=168
M=$C_{33}H_{40}ClN_3O_5$=565; M+H=566
$^1$H NMR (ppm, d6-DMSO, 400 MHz): 8.55 (s, 1H); 8.05 (d, 1H); 7.90 (d, 1H); 7.25 (m, 6H); 6.90 (dd, 1H); 4.65 (sl, 1H); 3.90 (m, 2H); 3.50 (m, 1H); 3.10 (m, 2H), 2.95 (q, 4H); 2.30 (m, 2H); 2.05 (m, 2H); 1.90 (s, 3H); 1.80 (m, 4H); 1.35 (m, 2H); 1.10 (t, 6H)

EXAMPLE 10

3-[({4"-Chloro-3"-[3-(dimethylamino)propoxy]-2,6-dimethoxy-1,1':2',1"-terphenyl-4'-yl}carbonyl)amino]-4-methylpentanoic acid hydrochloride (compound No. 28)

10.1. 2-[3-(benzyloxy)-4-chlorophenyl]-4,4,5,5-tetramethyl-1,3,2-dioxaborolane Stir a suspension of 20 g (67.2 mmol) of 2-benzyloxy-4-bromo-1-chlorobenzene, 28 g (94 mmol) of 4,4,4',4',5,5,5',5'-octamethyl-2,2'-bi-1,3,2-dioxaborolane and 26.4 g (26.9 mmol) of potassium acetate in 280 mL of anhydrous DMSO for 10 minutes under argon, then add 2.46 g (3.4 mmol) of $PdCl_2$ (dppf) and heat for 1 h at 110° C. After distributing in 1 L of a 1:1 ether/water mixture and filtering on a bed of celite, wash the organic phase with 100 mL of water, dry over $Na_2SO_4$, then concentrate under reduced pressure. Purify the residue obtained by silica gel column chromatography, eluting with a heptane/EtOAc gradient from 0 to 10% of EtOAc. After concentration under reduced pressure, we obtain 17.5 g of 2-[3-(benzyloxy)-4-chlorophenyl]-4,4,5,5-tetramethyl-1,3,2-dioxaborolane in the form of oil.
Yield=74%.

10.2. Methyl 2-bromo-2',6'-dimethoxybiphenyl-4-carboxylate

Stir a solution of 4.84 g (14.2 mmol) of methyl 3-bromo-4-iodobenzoate (*J. Med. Chem.,* 1999, 42, 4088) and 3.88 g (21.29 mmol) of 2,6-dimethoxyphenyl boronic acid in 120 mL of DMF and 14.2 mL of a 2M aqueous solution of caesium carbonate for 15 minutes under argon, then add 984 mg (0.85 mmol) of $Pd(PPh_3)_4$ and heat for 2.5 h at 85° C. After concentration under reduced pressure, distribute the residue obtained in 600 mL of a 1:1 DCM/water mixture. Wash the organic phase with 100 mL of water, dry over $MgSO_4$ and concentrate at reduced pressure. Purify the residue obtained by silica gel column chromatography, eluting with a heptane/EtOAc gradient from 0 to 10% of EtOAc. After concentration under reduced pressure, we obtain 2.79 g of methyl 2-bromo-2',6'-dimethoxybiphenyl-4-carboxylate in the form of oil.
Yield=56%

10.3. Methyl 3"-(benzyloxy)-4"-chloro-2,6-dimethoxy-1,1':2',1"-terphenyl-4'-carboxylate According to the method described in example 10.2, starting from 2.79 g (7.94 mmol) of methyl 2-bromo-2',6'-dimethoxybiphenyl-4-carboxylate and 3.28 g (9.53 mmol) of 2-[3-(benzyloxy)-4-chlorophenyl]-4,4,5,5-tetramethyl-1,3,2-dioxaborolane, we obtain 1.75 g of methyl 3"-(benzyloxy)-4"-chloro-2,6-dimethoxy-1,1':2',1"-terphenyl-4'-carboxylate in the form of oil.
Yield=45%

10.4. Methyl 4"-chloro-3"-[3-(dimethylamino)propoxy]-2,6-dimethoxy-1,1':2',1"-terphenyl-4'-carboxylate According to the debenzylation/O-alkylation steps described in examples 4.6 and 1.6 respectively, starting from 1.75 g (3.58 mmol) of methyl 3"-(benzyloxy)-4"-chloro-2,6-dimethoxy-1,1':2',1"-terphenyl-4'-carboxylate, we obtain 900 mg of methyl 4"-chloro-3"-[3-(dimethylamino)propoxy]-2,6-dimethoxy-1,1':2',1"-terphenyl-4'-carboxylate in the form of oil.
Yield=52%

10.5. 4"-Chloro-3"-[3-(dimethylamino)propoxy]-2,6-dimethoxy-1,1':2',1"-terphenyl-4'-carboxylic acid According to the method described in example 1.7, starting from 900 mg (1.86 mmol) of methyl 4"-chloro-3"-[3-(dimethylamino)propoxy]-2,6-dimethoxy-1,1':2',1"-terphenyl-4'-carboxylate, we obtain 700 mg of 4"-chloro-3"-[3-(dimethylamino)propoxy]-2,6-dimethoxy-1,1':2',1"-terphenyl-4'-carboxylic acid in the form of a pinkish solid.
Yield=82%
M.p. (° C.)=230.

10.6. 3-[({4"-Chloro-3"-[3-(dimethylamino)propoxy]-2,6-dimethoxy-1,1':2',1"-terphenyl-4'-yl}carbonyl)amino]-4-methylpentanoic acid hydrochloride Add 141 mg (0.87 mmol) of CDI to a solution of 315 mg (0.67 mmol) of 4"-chloro-3"-[3-(dimethylamino)propoxy]-

2,6-dimethoxy-1,1':2',1''-terphenyl-4'-carboxylic acid in 7 mL of anhydrous THF, and stir the reaction mixture at 55° C. for 1 h under argon. Add 70 mg (0.43 mmol) of carbonyl-1,1'-diimidazole and continue the reaction for 1 h at 50° C. Then add a suspension of 97 mg (0.74 mmol) of racemic 3-amino-4-methylpentanoic acid in a mixture of 4 mL of THF and 0.8 mL of DMF and continue stirring for 15 h at 55° C. After concentration under reduced pressure, distribute the residue obtained in 30 mL of a 2:1 DCM/water mixture. Wash the organic phase with 10 mL of water, dry over magnesium sulphate ($MgSO_4$) and concentrate under reduced pressure. Purify the residue obtained by silica gel column chromatography, eluting with a DCM/methanol gradient from 0 to 5% of methanol. After concentration under reduced pressure, solidify the residue in ether, filter on a frit and wash with ether. We thus obtain 91 mg of 3-[({4''-chloro-3''-[3-(dimethylamino)propoxy]-2,6-dimethoxy-1,1':2',1''-terphenyl-4'-yl}carbonyl)amino]-4-methylpentanoic acid hydrochloride in the form of white powder.

Yield=23%

M.p. (° C.)=152

M=$C_{32}H_{39}ClN_2O_6$=582; M+H=583

$^1$H NMR (ppm, d6-DMSO, 400 MHz): 8.3 (d, 1H); 7.75 (d, 1H); 7.7 (s, 1H); 7.2 (m, 3H); 6.7 (m, 2H); 6.55 (d, 2H); 4.1 (q, 1H) 3.8 (t, 2H); 3.5 (s, 6H); 2.45 (m, 4H); 2.3 (s, 6H) 1.8 (m, 3H); 0.9 (d, 6H).

EXAMPLE 11

3-({[5-{4-Chloro-3-[3-(dimethylamino)propoxy]phenyl}-6-(2-methylphenyl)pyridin-3-yl]carbonyl}amino)-4-methylpentanoic acid hydrochloride (compound 29)

11.1. Methyl 5-[3-(benzyloxy)-4-chlorophenyl]-6-oxo-1,6-dihydropyridine-3-carboxylate Stir a solution of 4 g (14.35 mmol) of methyl 5-iodo-6-oxo-1,6-dihydropyridine-3-carboxylate and 6.42 g (18.64 mmol) of 2-[3-(benzyloxy)-4-chlorophenyl]-4,4,5,5-tetramethyl-1,3,2-dioxaborolane in a mixture of 160 mL of dimethoxyethane (DME), 80 mL of EtOH and 120 mL of a saturated aqueous solution of $NaHCO_3$ for 15 minutes under argon, then add 662 mg of $Pd(PPh_3)_4$ and heat the reaction mixture for 4 h 30 min at 90° C. After concentration under reduced pressure, distribute the residue obtained in a mixture of 200 mL of DCM and 10 mL of water. Extract the aqueous phase again with 100 mL of DCM, combine the organic phases, dry over $MgSO_4$, filter and concentrate under reduced pressure. Purify the residue obtained by silica gel column chromatography, eluting with a DCM/methanol gradient from 0 to 2% of methanol. After concentration under reduced pressure, solidify the residue in a 5/95 methanol/ether mixture, then filter and wash with ether. We thus obtain 1.99 g of methyl 5-[3-(benzyloxy)-4-chlorophenyl]-6-oxo-1,6-dihydropyridine-3-carboxylate in the form of a beige solid.

Yield=40%

M.p. (° C.): 190

11.2. Methyl 5-[3-(benzyloxy)-4-chlorophenyl]-6-{[(trifluoromethyl)sulphonyl]oxy}nicotinate According to the method described in example 4.4, starting from 1.99 g (5.38 mmol) of methyl 5-[3-(benzyloxy)-4-chlorophenyl]-6-oxo-1,6-dihydropyridine-3-carboxylate and 2.26 ml (13.45 mmol) of trifluoromethanesulphonic anhydride, we obtain 1.6 g of methyl 5-[3-(benzyloxy)-4-chlorophenyl]-6-{[(trifluoromethyl)sulphonyl]oxy}nicotinate in the form of oil.

Yield=60%

11.3. Methyl 5-[3-(benzyloxy)-4-chlorophenyl]-6-(2-methylphenyl)nicotinate

According to the method described in example 4.5, starting from 1.5 g (2.99 mmol) of methyl 5-[3-(benzyloxy)-4-chlorophenyl]-6-{[(trifluoromethyl)sulphonyl]oxy}nicotinate and of 508 mg (3.74 mmol) of 2-methylphenyl boronic acid, we obtain 1.26 g of methyl 5-[3-(benzyloxy)-4-chlorophenyl]-6-(2-methylphenyl)nicotinate in the form of oil.

Yield=95%

11.4. Methyl 5-{4-chloro-3-[3-(dimethylamino)propoxy]phenyl}-6-(2-methylphenyl)nicotinate According to the debenzylation/O-alkylation steps described in examples 4.6 and 1.6 respectively, starting from 1.26 g (2.84 mmol) of methyl 5-[3-(benzyloxy)-4-chlorophenyl]-6-(2-methylphenyl)nicotinate, we obtain 843 mg of methyl 5-{4-chloro-3-[3-(dimethylamino)propoxy]phenyl}-6-(2-methylphenyl)nicotinate in the form of oil.

Yield=68%

11.5. 3-({[5-{4-Chloro-3-[3-(dimethylamino)propoxy]phenyl}-6-(2-methylphenyl)pyridin-3-yl]carbonyl}amino)-4-methylpentanoic acid hydrochloride According to the saponification/peptide coupling steps described in examples 1.7 and 10.6 respectively, starting from 835 mg (1.90 mmol) of methyl 5-{4-chloro-3-[3-(dimethylamino)propoxy]phenyl}-6-(2-methylphenyl)nicotinate and 258 mg (1.97 mmol) of racemic 3-amino-4-methylpentanoic acid, we obtain 130 mg of 3-({[5-{4-chloro-3-[3-(dimethylamino)propoxy]phenyl}-6-(2-methylphenyl)pyridin-3-yl]carbonyl}amino)-4-methylpentanoic acid hydrochloride in the form of a white solid.

Yield=13%

M.p. (° C.)=139

M=$C_{30}H_{36}ClN_3O_4$=537; M+H=538

$^1$H NMR (ppm, d6-DMSO, 400 MHz): 9.05 (d, 1H); 9.5 (d, 1H); 9.25 (d, 1H); 8.3 (d, 1H); 7.3 (d, 1H) 7.15 (d, 1H); 7.15 (m, 4H); 4.25 (m, 1H); 3.8 (t, 2H); 2.65 (t, 2H); 2.45 (s, 6H) 1.95 (s, 3H); 1.85 (m, 5H); 0.90 (d, 6H).

EXAMPLE 12

2-({[6-[3-[3-(Dimethylamino)propoxy]-4-(trifluoromethyl)phenyl]-5-(2-methylphenyl)pyridin-2-yl]carbonyl}amino)adamantane-2-carboxylic acid hydrochloride (compound No. 43)

12.1. 2-iodo-5-nitrophenol

Add, dropwise, a solution of 20.7 g (300 mmol) of sodium nitrite ($NaNO_2$) in 100 mL of water to a solution of 30.81 g (200 mmol) of 2-amino-5-nitrophenol in a mixture of 500 mL of sulphuric acid at 30 wt. % and 500 mL of DMSO cooled to 5° C., maintaining the temperature at 5° C. After 30 min at 5° C., add dropwise a solution of 90 g (600 mmol) of sodium iodide in 100 mL of water, then bring the reaction mixture up to RT. After stirring for 2 h, distribute the reaction mixture in 2 L of a mixture of ether/aqueous solution at 10 wt. % of sodium bisulphite 1:1. Extract the aqueous phase again with 200 mL of ether, combine the organic phases and wash with 3×1 L of water, then dry over Na₂SO₄. After concentration under reduced pressure, purify the residue obtained by silica gel column chromatography, eluting with a cyclohexane/ EtOAc gradient from 0 to 10% of EtOAc. After concentration under reduced pressure, we obtain 39.8 g of 2-iodo-5-nitrophenol in the form of a brown solid.
Yield=75%
M.p. (° C.)=150

12.2. 2-(benzyloxy)-1-iodo-4-nitrobenzene

According to the method described in example 4.1., starting from 20.8 g (78.5 mmol) of 2-iodo-5-nitrophenol and 9.3 mL (78.5 mmol) of benzyl bromide, we obtain 25.2 g of 2-(benzyloxy)-1-iodo-4-nitrobenzene in the form of oil.
Yield=90%

12.3. 2-(benzyloxy)-4-nitro-1-(trifluoromethyl)benzene

Add 10.4 mL (70.18 mmol) of trifluoromethyltrimethylsilane to a mixture of 4.08 g (70.2 mmol) of anhydrous potassium fluoride and 13.36 g (70.18 mmol) of anhydrous CuI and 19.17 g (54 mmol) of 2-(benzoxy)-1-iodo-nitrobenzene in 77 mL of anhydrous NMP, and heat the reaction mixture for 18 h at 45° C. under argon. Distribute the suspension at RT in 1 L of a 1:1 ether/water mixture, then wash the organic phase with 4×300 mL of water, dry over Na₂SO₄, and concentrate under reduced pressure. We thus obtain 15 g of 2-(benzyloxy)-4-nitro-1-(trifluoromethyl)benzene in the form of oil.
Yield=94%

12.4. 3-(benzyloxy)-4-(trifluoromethyl)aniline

Add 14.1 g (252 mmol) of iron filings to a mixture of 15 g (50.3 mmol) of 2-(benzyloxy)-4-nitro-1-(trifluoromethyl)benzene in 200 mL of EtOH, 10 mL of AcOH and 100 mL of water, then stir the reaction mixture vigorously at 70° C. for 20 minutes. After cooling to RT, slowly add the reaction mixture to a mixture of 300 mL of ether and 1 L of a saturated aqueous solution of Na₂CO₃. After neutralizing, extract the aqueous phase again with 2×100 mL of ether. Combine the organic phases, wash with 100 mL of water, dry over calcium chloride and concentrate under reduced pressure. Purify the residue obtained by silica gel column chromatography, eluting with a pentane/EtOAc gradient from 0 to 50% of EtOAc. After concentration under reduced pressure, we obtain 8.1 g of 3-(benzyloxy)-4-(trifluoromethyl)aniline in the form of oil.
Yield=60%

12.5. 2-(benzyloxy)-4-iodo-1-(trifluoromethyl)benzene

According to the method described in example 12.1., starting from 8 g (30 mmol) of 3-(benzyloxy)-4-(trifluoromethyl) aniline, we obtain 8 g of 2-(benzyloxy)-4-iodo-1-(trifluoromethyl)benzene in the form of oil.
Yield=70%

12.6. [3-(Benzyloxy)-4-(trifluoromethyl)phenyl]boronic acid

According to the method described in example 4.2, starting from 8 g (21.2 mmol) of 2-(benzyloxy)-4-iodo-1-(trifluoromethyl)benzene, 11.1 mL (22.2 mmol) of iPrMgCl and 5 mL (21.6 mmol) of triisopropyl borate, we obtain 4.95 g of [3-(benzyloxy)-4-(trifluoromethyl)phenyl]boronic acid in the form of oil.
Yield=79%

12.7. Methyl 6-[3-(benzyloxy)-4-(trifluoromethyl) phenyl]-5-hydroxypyridine-2-carboxylate According to the method described in example 4.3, starting from 4.95 g (16.7 mmol) of [3-(benzyloxy)-4-(trifluoromethyl)phenyl]boronic acid and 3.88 g (16.72 mmol) of methyl 6-bromo-5-hydroxypyridine-2-carboxylate, we obtain 4.38 g of methyl 6-[3-(benzyloxy)-4-(trifluoromethyl)phenyl]-5-hydroxypyridine-2-carboxylate in the form of a white solid.
Yield=65%
M.p. (° C.)=82

12.8. Methyl 6-[3-(benzyloxy)-4-(trifluoromethyl) phenyl]-5-(2-methylphenyl)pyridine-2-carboxylate According to the triflate/Suzuki coupling steps described in examples 4.4 and 4.5 respectively, starting from 4.38 g (10.9 mmol) of methyl 6-[3-(benzyloxy)-4-(trifluoromethyl) phenyl]-5-hydroxypyridine-2-carboxylate and 1.8 g (13.1 mmol) of 2-methylphenylboronic acid, we obtain 4.63 g of methyl 6-[3-(benzyloxy)-4-(trifluoromethyl)phenyl]-5-(2-methylphenyl)pyridine-2-carboxylate in the form of a white solid.
Yield=89%
M.p. (° C.)=226

12.9. Methyl 6-[3-[3-(dimethylamino)propoxy]-4-(trifluoromethyl)phenyl]-5-(2-methylphenyl)pyridine-2-carboxylate According to the debenzylation/O-alkylation steps described in examples 4.6 and 1.6 respectively, starting from 2.57 g (5.38 mmol) of methyl 6-[3-(benzyloxy)-4-(trifluoromethyl)phenyl]-5-(2-methylphenyl)pyridine-2-carboxylate, we obtain 2.26 g of methyl 6-[3-[3-(dimethylamino) propoxy]-4-(trifluoromethyl)phenyl]-5-(2-methylphenyl) pyridine-2-carboxylate in the form of a white solid.
Yield=89%
M.p. (° C.)=142

12.10. 2-({[6-[3-[3-(Dimethylamino)propoxy]-4-(trifluoromethyl)phenyl]-5-(2-methylphenyl)pyridin-2-yl]carbonyl}amino)adamantane-2-carboxylic acid hydrochloride According to the saponification/peptide coupling steps described in examples 1.7 and 1.8 respectively, starting from 565 mg (1.19 mmol) of methyl 6-[3-[3-(dimethylamino)propoxy]-4-(trifluoromethyl)phenyl]-5-(2-methylphenyl)pyridine-2-carboxylate and 256 mg (1.31 mmol) of 2-aminoadamantane-2-carboxylic acid, we obtain 440 mg of 2-({[6-[3-[3-(dimethylamino)propoxy]-4-(trifluoromethyl) phenyl]-5-(2-methylphenyl)pyridin-2-yl]carbonyl}amino) adamantane-2-carboxylic acid hydrochloride in the form of white powder.
Yield=55%
M.p. (° C.)=231
M=$C_{36}H_{40}F3N_3O_4$=634; M+H=635
¹H NMR (ppm, d6-DMSO, 400 MHz): 8.50 (s, 1H); 8.10 (d, 1H); 7.95 (d, 1H); 7.55 (d, 1H); 7.25 (m, 5H); 7.10 (d, 1H);

3.90 (m, 2H); 3.05 (m, 2H); 2.70 (s, 6H); 2.60 (s, 2H); 2.05 (m, 7H); 1.90 (s, 3H); 1.65 (m, 7H).

EXAMPLE 13

1-{[(3-Chloro-2'-{4-chloro-3-[3-(dimethylamino) propoxy]phenyl}-2,3'-bipyridin-6'-yl)carbonyl] amino}cyclohexane carboxylic acid hydrochloride (compound No. 55)

13.1. Methyl 6-[3-(benzyloxy)-4-chlorophenyl]-5-(4,4,5,5-tetramethyl-1,3,2-dioxaborolan-2-yl)pyridine-2-carboxylate Stir a solution of 5 g (10 mmol) of methyl 6-[3-(benzyloxy)-4-chlorophenyl]-5-{[(trifluoromethyl)sulphonyl] oxy}pyridine-2-carboxylate and 2.78 g (11 mmol) of 4,4,4',4',5,5,5',5'-octamethyl-2,2'-bi-1,3,2-dioxaborolane in 50 mL of anhydrous 1,4-dioxan for 15 min while bubbling with argon, then add 2.93 g (30 mmol) of anhydrous potassium acetate and 0.37 g (0.45 mmol) of $PdCl_2(dppf)$ and heat the reaction mixture for 26 h at 80°. Then distribute the reaction mixture in 100 mL of EtOAc/brine 1:1 mixture. Dry the organic phase over $Na_2SO_4$, filter, and then concentrate under reduced pressure. Purify the residue obtained by chromatography on a silica column, eluting with a cyclohexane/EtOAc gradient from 0 to 20% of EtOAc. After concentration under reduced pressure, we obtain 3.2 g of methyl 6-[3-(benzyloxy)-4-chlorophenyl]-5-(4,4,5,5-tetramethyl-1,3,2-dioxaborolan-2-yl)pyridine-2-carboxylate in the form of a wax.

Yield=67%

13.2. Methyl 2'-[3-(benzyloxy)-4-chlorophenyl]-3-chloro-2,3'-bipyridine-6'-carboxylate Stir a solution of 850 mg (1.77 mmol) of methyl 6-[3-(benzyloxy)-4-chlorophenyl]-5-(4,4,5,5-tetramethyl-1,3,2-dioxaborolan-2-yl)pyridine-2-carboxylate and 524 mg (3.54 mmol) of 2,3-dichloropyridine in a mixture of 4 mL of DME and 2 mL of water for 15 minutes under argon, then add successively 734 mg (5.32 mmol) of $K_2CO_3$ and 61 mg (0.05 mmol) of $Pd(PPh_3)_4$ and heat the reaction mixture for 4 h at 85° C. Then distribute the reaction mixture between 10 mL of EtOAc and 10 mL of brine. Dry the organic phase over $Na_2SO_4$, filter, and then concentrate under reduced pressure. Purify the residue obtained on a silica column, eluting with a cyclohexane/EtOAc gradient from 0 to 20% of EtOAc. After concentration under reduced pressure, we obtain 237 mg of methyl 2'-[3-(benzyloxy)-4-chlorophenyl]-3-chloro-2,3'-bipyridine-6'-carboxylate in the form of oil.

Yield=28%

13.3. Methyl 3-chloro-2'-{4-chloro-3-[3-(dimethylamino)propoxy]phenyl}-2,3'-bipyridine-6'-carboxylate According to the debenzylation/O-alkylation steps described in examples 4.6 and 1.6 respectively, starting from 360 mg (0.77 mmol) of methyl 2'-[3-(benzyloxy)-4-chlorophenyl]-3-chloro-2,3'-bipyridine-6'-carboxylate, we obtain 130 mg of methyl 3-chloro-2'-{4-chloro-3-[3-(dimethylamino)propoxy]phenyl}-2,3'-bipyridine-6'-carboxylate in the form of oil.

Yield=37%

13.4. 1-{[(3-Chloro-2'-{4-chloro-3-[3-(dimethylamino)propoxy]phenyl}-2,3'-bipyridin-6'-yl)carbonyl]amino}cyclohexane carboxylic acid hydrochloride According to the saponification/peptide coupling steps described in examples 1.7 and 1.8 respectively, starting from 130 mg (0.28 mmol) of methyl 3-chloro-2'-{4-chloro-3-[3-(dimethylamino)propoxy]phenyl}-2,3'-bipyridine-6'-carboxylate and 44 mg (0.31 mmol) of 2-aminocyclohexanecarboxylic acid, we obtain 120 mg of 1-{[(3-chloro-2'-{4-chloro-3-[3-(dimethylamino)propoxy]phenyl}-2,3'-bipyridin-6'-yl)carbonyl]amino}cyclohexane carboxylic acid hydrochloride in the form of white powder.

Yield=70%

M.p. (° C.)=140

M=$C_{29}H_{32}Cl_2N_4O_4$=570; M+H=571

$^1$H NMR (ppm, d6-DMSO, 400 MHz): 10.45 (s, 1H); 8.65 (d, 1H); 8.45 (s, 1H); 8.10 (s, 2H); 7.95 (d, 1H); 7.50 (dd, 1H); 7.35 (d, 1H); 7.25 (d, 1H); 6.90 (dd, 1H); 3.95 (t, 2H); 3.15 (m, 2H); 2.80 (d, 6H); 2.20 (m, 4H); 1.80 (t, 2H); 1.70-1.2 (m, 6H).

EXAMPLE 14

(3S)-3-({[6-{4-chloro-3-[3-(dimethylamino)propoxy]phenyl}-5-(2-chloro-5-methylphenyl)pyridin-2-yl]carbonyl}amino)-4-methylpentanoic acid hydrochloride (compound No. 72)

14.1. Methyl 6-{4-chloro-3-[3-(dimethylamino)propoxy]phenyl}-5-(2-chloro-5-methylphenyl)pyridine-2-carboxylate According to the debenzylation/O-alkylation steps described in examples 4.6 and 1.6 respectively, starting from 743 mg (1.55 mmol) of 6-[3-(benzyloxy)-4-chlorophenyl]-5-(2-chloro-5-methylphenyl)pyridine-2-carboxylate, we obtain 530 mg of 6-{4-chloro-3-[3-(dimethylamino)propoxy]phenyl}-5-(2-chloro-5-methylphenyl)pyridine-2-carboxy in the form of oil.

Yield=72%

14.2. (3S)-3-({[6-{4-Chloro-3-[3-(dimethylamino)propoxy]phenyl}-5-(2-chloro-5-methylphenyl)pyridin-2-yl]carbonyl}amino)-4-methylpentanoic acid hydrochloride According to the saponification/peptide coupling steps described in examples 1.7 and 9 respectively, starting from 385 mg (0.84 mmol) of 6-{4-chloro-3-[3-(dimethylamino)propoxy]phenyl}-5-(2-chloro-5-methylphenyl)pyridine-2-carboxylate and 130 mg (1 mmol) of (3S)-3-amino-4-methylpentanoic acid (*J. Org. Chem.*, 1999, 6411-6417), we obtain 333 mg of (3S)-3-({[6-{4-chloro-3-[3-(dimethylamino)propoxy]phenyl}-5-(2-chloro-5-methylphenyl)pyridin-2-yl]carbonyl}amino)-4-methylpentanoic acid hydrochloride in the form of white powder.

Yield=67%

M.p. (° C.)=157

$[\alpha]_D^{22}$=−18°; (c=0.1; MeOH)

M=$C_{30}H_{35}Cl_2N_3O_4$=571; M+H=572

$^1$H NMR (ppm, d6-DMSO, 400 MHz): 8.60 (dd, 1H); 8.10 (d, 1H); 7.95 (d, 1H); 7.40-7.15 (m, 5H); 6.90 (d, 1H); 4.15

(m, 1H); 3.90 (m, 2H); 3.15 (t, 2H); 2.75 (s, 6H); 2.55 (t, 2H); 2.25 (d, 3H (conformers)); 2.10 (m, 2H); 1.90 (m, 1H); 0.85 (dd, 6H (conformers)).

EXAMPLE 15

1-({[6-{4-Chloro-3-[3-(dimethylamino)propoxy]phenyl}-5-(2,4-dimethylphenyl)pyridin-2-yl]carbonyl}amino)cyclohexanecarboxylic acid hydrochloride (compound No. 66)

15.1. Methyl 6-[3-(benzyloxy)-4-chlorophenyl]-5-(2,4-dimethylphenyl)pyridine-2-carboxylate According to the method described in example 4.5, Suzuki coupling effected between 1 g (2 mmol) of methyl 6-[3-(benzyloxy)-4-chlorophenyl]-5-{[(trifluoromethyl)sulphonyl]oxy}pyridine-2-carboxylate and 418 mg (2.8 mmol) of 2,4-dimethylphenylboronic acid leads to 820 mg of methyl 6-[3-(benzyloxy)-4-chlorophenyl]-5-(2,4-dimethylphenyl)pyridine-2-carboxylate in the form of oil.
Yield=90%

15.2. 6-{4-Chloro-3-[3-(dimethylamino)propoxy]phenyl}-5-(2,4-dimethylphenyl)pyridine-2-carboxylic acid hydrochloride According to the debenzylation/O-alkylation/saponification steps described in examples 4.6, 1.6 and 1.7 respectively, starting from 820 mg (1.8 mmol) of methyl 6-[3-(benzyloxy)-4-chlorophenyl]-5-(2,4-dimethylphenyl)pyridine-2-carboxylate, we obtain 659 mg of 6-{4-chloro-3-[3-(dimethylamino)propoxy]phenyl}-5-(2,4-dimethylphenyl)pyridine-2-carboxylic acid hydrochloride in the form of gum.
Yield=77%

15.3. 1-({[6-{4-Chloro-3-[3-(dimethylamino)propoxy]phenyl}-5-(2,4-dimethylphenyl)pyridin-2-yl]carbonyl}amino)cyclohexanecarboxylic acid hydrochloride According to the method described in example 1.8, peptide coupling effected between 356 mg (0.75 mmol) of 6-{4-chloro-3-[3-(dimethylamino)propoxy]phenyl}-5-(2,4-dimethylphenyl)pyridine-2-carboxylic acid hydrochloride and 113 mg (0.79 mmol) of 2-aminocyclohexane-2-carboxylic acid leads to 160 mg of 1-({[6-{4-chloro-3-[3-(dimethylamino)propoxy]phenyl}-5-(2,4-dimethylphenyl)pyridin-2-yl]carbonyl}amino)cyclohexanecarboxylic acid hydrochloride in the form of white powder.
Yield=38%
M.p. (° C.)=158
$M=C_{32}H_{38}ClN_3O_4=563$; M+H=564
$^1$H NMR (ppm, d6-DMSO, 400 MHz): 12.45 (s, 1H); 10.40 (s, 1H); 8.45 (s, 1H); 8.05 (d, 1H); 7.95 (d, 1H); 7.40 (d, 1H); 7.20 (s, 1H); 7.15 (s, 2H); 2.75 (s, 6H); 7.10 (d, 1H); 7.05 (d, 1H); 3.90 (m, 2H); 3.20 (t, 2H); 2.70 (s, 6H); 2.35 (s, 3H); 2.2-2.05 (m, 4H); 1.90 (s, 3H); 1.85 (t, 2H); 1.75-1.30 (m, 6H).

EXAMPLE NO. 16

(3S)-3-({[6-{4-Chloro-3-[3-(dimethylamino)propoxy]phenyl}-5-(2,4-dimethylphenyl)pyridin-2-yl]carbonyl}amino)-4,4-dimethylpentanoic acid hydrochloride (compound No. 117)

According to the method described in example 9, peptide coupling effected between 950 mg (2 mmol) of 6-{4-chloro-3-[3-(dimethylamino)propoxy]phenyl}-5-(2,4-dimethylphenyl)pyridine-2-carboxylic acid hydrochloride and 412 mg (2.05 mmol) of tert-butyl (3S)-3-amino-4,4-dimethylpentanoate (J. Org. Chem., 1999, 64, 6411-6417) leads to 830 mg of (3S)-3-({[6-{4-chloro-3-[3-(dimethylamino)propoxy]phenyl}-5-(2,4-dimethylphenyl)pyridin-2-yl]carbonyl}amino)-4,4-dimethylpentanoic acid hydrochloride in the form of white powder.
Yield=70%
M.p. (° C.)=130
$[\alpha]_D^{22}=-5°$; (c=0.1; MeOH)
$M=C_{32}H_{40}ClN_3O_4=565$; M+H=566
$^1$H NMR (ppm, d6-DMSO, 400 MHz): 10.09 (s, 1H); 8.2 (d, 1H); 7.85 (d, 1H); 7.70 (d, 1H); 7.10 (d, 1H); 6.95 (d, 1H); 6.85 (m, 3H); 6.80 (t, 1H); 4.10 (t, 1H); 3.65 (m, 2H); 2.95 (m, 2H); 2.50 (d, 6H); 2.40 (dd, 1H); 2.30 (dd, 1H); 2.10 (s, 3H); 1.85 (m, 2H); 1.65 (s, 3H); 0.70 (d, 9H, conformers).

EXAMPLE NO. 17

1-{[(3,5-Dichloro-2'-{4-chloro-3-[3-(dimethylamino)propoxy]phenyl}-2,3'-bipyridin-6'-yl)carbonyl]amino}cyclohexanecarboxylic acid hydrochloride (compound No. 65)

17.1. Methyl 2'-[3-(benzyloxy)-4-chlorophenyl]-3,5-dichloro-2,3'-bipyridine-6'-carboxylate According to the method described in example 13.2, Suzuki-Myaura coupling effected between 4.4 g (9.17 mmol) of methyl 6-[3-(benzyloxy)-4-chlorophenyl]-5-(4,4,5,5-tetramethyl-1,3,2-dioxaborolan-2-yl)pyridine-2-carboxylate and 2.5 g (11 mmol) of 2-bromo-3,5-dichloropyridine leads to 3 g of methyl 2'-[3-(benzyloxy)-4-chlorophenyl]-3,5-dichloro-2,3'-bipyridine-6'-carboxylate in the form of oil.
Yield=65%

17.2. Methyl 3,5-dichloro-2'-{4-chloro-3-[3-(dimethylamino)propoxy]phenyl}-2,3'-bipyridine-6'-carboxylate According to the debenzylation/O-alkylation steps described in examples 4.6 and 1.6 respectively, starting from 3 g (6.2 mmol) of methyl 2'-[3-(benzyloxy)-4-chlorophenyl]-3,5-dichloro-2,3'-bipyridine-6'-carboxylate, we obtain 1.8 g of methyl 3,5-dichloro-2'-{4-chloro-3-[3-(dimethylamino)propoxy]phenyl}-2,3'-bipyridine-6'-carboxylate in the form of gum.
Yield=58%

17.3. 1-{[(3,5-Dichloro-2'-{4-chloro-3-[3-(dimethylamino)propoxy]phenyl}-2,3'-bipyridin-6'-yl)carbonyl]amino}cyclohexanecarboxylic acid hydrochloride According to the saponification/peptide coupling steps described in examples 1.7 and 1.8 respectively, starting from 1.8 g (3.62 mmol) of methyl 3,5-dichloro-2'-{4-chloro-3-[3-(dimethylamino)propoxy]phenyl}-2,3'-bipyridine-6'-carboxylate and 472 mg (3.3 mmol) of 2-aminocyclohexane-2-carboxylic acid, we obtain 1.12 g of 1-{[(3,5-dichloro-2'-{4-chloro-3-[3-(dimethylamino)propoxy]phenyl}-2,3'-bipyridin-6'-yl)carbonyl]amino}cyclohexanecarboxylic acid hydrochloride in the form of white powder.
Yield=50%
M.p. (° C.)=165
$MC_{23}H_{31}Cl_3N_4O_4=604$; M+H=605

¹H NMR (ppm, d6-DMSO, 400 MHz): 8.75 (s, 1H); 8.45 (s, 1H); 8.30 (d, 1H); 8.15 (dd, 2H); 7.35 (d, 1H); 7.30 (s, 1H); 6.75 (dd, 1H); 4.00 (t, 2H); 3.20 (m, 2H); 2.75 (d, 6H); 2.3-1.3 (m, 12H).

EXAMPLE NO. 18

1-({[6-{4-Chloro-3-[3-(dimethylamino)propoxy] phenyl}-5-(3,5-dimethyl-1H-pyrazol-1-yl)pyridin-2-yl]carbonyl}amino)cyclohexanecarboxylic acid hydrochloride (compound No. 75)

18.1. Methyl 6-[3-(benzyloxy)-4-chlorophenyl]-5-[2-(diphenylmethylidene)hydrazino]pyridine-2-carboxylate Put 2 g (4 mmol) of methyl 6-[3-(benzyloxy)-4-chlorophenyl]-5-{[(trifluoromethyl)sulphonyl]oxy}pyridine-2-carboxylate in 10 mL of anhydrous toluene in a screw-top bottle. To the solution, under argon, add successively 938 mg (4.78 mmol) of benzophenone hydrazone, 1.95 g (6 mmol) of caesium carbonate and 65 mg (0.08 mmol) of PdCl$_2$ (dppf). Heat the reaction mixture for 3 h at 90° C. while stirring, then distribute in 100 mL of ether/water 1:1 mixture. Dry the organic phase over Na$_2$SO$_4$ and concentrate under reduced pressure. Purify the residue obtained by silica gel column chromatography, eluting with a DCM/acetone gradient from 0 to 5% of acetone. After concentration under reduced pressure, we obtain 1.94 g of methyl 6-[3-(benzyloxy)-4-chlorophenyl]-5-[2-(diphenylmethylidene)hydrazino]pyridine-2-carboxylate in the form of oil.

Yield=88%

18.2. Ethyl 6-[3-(benzyloxy)-4-chlorophenyl]-5-(3,5-dimethyl-1H-pyrazol-1-yl)pyridine-2-carboxylate Put 600 mg (1.08 mmol) of methyl 6-[3-(benzyloxy)-4-chlorophenyl]-5-[2-(diphenylmethylidene)hydrazino]pyridine-2-carboxylate, 378 mg (3.78 mmol) of 2,4-pentanedione, 186 mg (1.08 mmol) of paratoluenesulphonic acid and 5 mL of ethanol in a screw-top bottle. Heat the mixture at 120° C. while stirring for 48 h, then cool, and concentrate under reduced pressure. Then distribute the residue in 50 mL of EtOAc and 50 mL of a saturated aqueous solution of NaHCO$_3$. Dry the organic phase over Na$_2$SO$_4$ and concentrate under reduced pressure. Purify the residue obtained by silica gel column chromatography, eluting with a heptane/EtOAc gradient from 0 to 50% of EtOAc. After concentration under reduced pressure, we obtain 235 mg of ethyl 6-[3-(benzyloxy)-4-chlorophenyl]-5-(3,5-dimethyl-1H-pyrazol-1-yl)pyridine-2-carboxylate in the form of oil.

Yield=47%

18.3. 6-{4-Chloro-3-[3-(dimethylamino)propoxy] phenyl}-5-(3,5-dimethyl-1H-pyrazol-1-yl)pyridine-2-carboxylic acid hydrochloride According to the debenzylation/O-alkylation/saponification steps described in examples 4.6, 1.6 and 1.7 respectively, starting from 1 g (2.25 mmol) of ethyl 6-[3-(benzyloxy)-4-chlorophenyl]-5-(3,5-dimethyl-1H-pyrazol-1-yl)pyridine-2-carboxylate, we obtain 460 mg of 6-{4-chloro-3-[3-(dimethylamino)propoxy]phenyl}-5-(3,5-dimethyl-1H-pyrazol-1-yl)pyridine-2-carboxylic acid hydrochloride.

Yield=43%

18.4. 1-({[6-{4-Chloro-3-[3-(dimethylamino)propoxy]phenyl}-5-{3,5-dimethyl-1H-pyrazol-1-yl)pyridin-2-yl]carbonyl}amino)cyclohexanecarboxylic acid hydrochloride According to the method described in example 9, peptide coupling effected between 460 mg (1 mmol) of 6-{4-chloro-3-[3-(dimethylamino)propoxy]phenyl}-5-(3,5-dimethyl-1H-pyrazol-1-yl)pyridine-2-carboxylic acid hydrochloride and 156 mg (1.09 mmol) of 2-aminocyclohexane-2-carboxylic acid leads to 270 mg of 1-({[6-{4-chloro-3-[3-(dimethylamino)propoxy]phenyl}-5-(3,5-dimethyl-1H-pyrazol-1-yl)pyridin-2-yl]carbonyl}amino)cyclohexanecarboxylic acid hydrochloride in the form of white powder.

Yield=46%

M.p. (° C.)=202

MC$_{29}$H$_{36}$ClN$_5$O$_4$=553; M+H=554

¹H NMR (ppm, d6-DMSO, 400 MHz): 12.45 (s, 1H); 10.3 (s, 1H); 8.40 (s, 1H); 8.15 (s, 2H); 7.45 (d, 1H); 7.00 (m, 2H); 6.05 (s, 1H); 3.95 (t, 2H); 3.15 (m, 2H); 2.75 (d, 6H); 2.20 (s, 3H); 2.15 (m, 4H); 1.70 (s, 3H); 2.9-1.2 (m, 8H).

EXAMPLE NO. 19

1-({[6-{4-Chloro-3-[3-(dimethylamino)propoxy] phenyl}-5-(2-methylphenyl)pyrazin-2-yl] carbonyl}amino)cyclohexanecarboxylic acid hydrochloride (compound No. 80)

19.1. 5-aminopyrazine-2-carbonitrile

Heat a suspension of 1.85 g (20.7 mmol) of copper cyanide and 1 g (20.7 mmol) of sodium cyanide in 20 ml of DMF to 135° C., while stirring. Add 3.6 g (20.7 mmol) of 5-bromopyrazin-2-amine to the solution obtained, and maintain the temperature of 135° C. for 18 h. Then add 2 equivalents of sodium cyanide and of copper cyanide and continue heating for a further 24 h. After cooling, add 100 mL of 0.3N aqueous solution of sodium cyanide, stir the mixture for 1 h at 40° C., then distribute it in 300 mL of EtOAc/water 1:1 mixture. After washing with 2×100 mL of water, dry the organic phase over Na$_2$SO$_4$ and concentrate under reduced pressure. Purify the residue obtained by silica gel column chromatography, eluting with a cyclohexane/EtOAc gradient from 0 to 100% of EtOAc. After concentration under reduced pressure, we obtain 1.24 g of 5-aminopyrazine-2-carbonitrile in the form of oil.

Yield=50%

19.2. Methyl 5-aminopyrazine-2-carboxylate

Reflux a solution of 2.24 g (18.65 mmol) of 5-aminopyrazine-2-carbonitrile and 9.45 mL (74.40 mmol) of boron trifluoride etherate in 50 mL of methanol for 2 h. Concentrate the reaction mixture under reduced pressure and take up the residue obtained in 200 mL of EtOAc and 10 mL of a saturated aqueous solution of NaHCO$_3$. Dry the organic phase over Na$_2$SO$_4$ and concentrate under reduced pressure. Purify the residue obtained by silica gel column chromatography, eluting with a cyclohexane/EtOAc 1:1 mixture. After concentration under reduced pressure, we obtain 1.4 g of methyl 5-aminopyrazine-2-carboxylate in the form of oil.

Yield=49%

19.3. Methyl 5-amino-6-bromopyrazine-2-carboxylate

Add 1.79 g (10.05 mmol) of N-bromosuccinimide to a solution of 1.4 g (9.14 mmol) of methyl 5-aminopyrazine-2- carboxylate in 10 mL of acetonitrile. Stir the reaction mixture for 2 h at 20° C. then distribute in 100 mL of EtOAc/water 1:1 mixture. Wash the organic phase with 2×50 mL of water, dry over Na$_2$SO$_4$ and concentrate under reduced pressure. Purify the residue obtained by silica gel column chromatography, eluting with a cyclohexane/EtOAc gradient from 0 to 50% of EtOAc. After concentration under reduced pressure, we obtain 1.66 g of methyl 5-amino-6-bromopyrazine-2-carboxylate in the form of yellow wax.

Yield=78%

19.4. Methyl 5-amino-6-[3-(benzyloxy)-4-chlorophenyl]pyrazine-2-carboxylate

Stir a suspension of 137 mg (0.36 mmol) of (bis-benzonitrile)-palladium II dichloride and 183 mg (0.43 mmol) of diphenylphosphinobutane in 7 mL of toluene under argon for 30 min at room temperature. Then add, while bubbling with argon, 1.66 g (7.15 mmol) of methyl 5-amino-6-bromopyrazine-2-carboxylate, 1.97 g (7.51 mmol) of [3-(benzyloxy)-4-chlorophenyl]boronic acid, 2.4 mL of ethanol and 3.58 mL (7.15 mmol) of a 2N aqueous solution of sodium carbonate. Reflux the reaction mixture for 5 h 30 min and then distribute in 100 mL of a water/EtOAc 1:1 mixture. Wash the organic phase with 50 mL of water, dry over Na$_2$SO$_4$ and concentrate under reduced pressure. Purify the residue, obtained by silica gel column chromatography, eluting with a cyclohexane/EtOAc gradient from 50 to 100% of EtOAc. After concentration under reduced pressure, we obtain 1.33 g of methyl 5-amino-6-[3-(benzyloxy)-4-chlorophenyl]pyrazine-2-carboxylate in the form of yellow wax.

Yield=50%

19.5. Methyl 6-[3-(benzyloxy)-4-chlorophenyl]-5-bromopyrazine-2-carboxylate

Add, dropwise, 0.82 mL (6.9 mmol) of tert-butyl nitrite to a solution of 1.28 g (3.46 mmol) of methyl 5-amino-6-[3-(benzyloxy)-4-chlorophenyl]pyrazine-2-carboxylate in 10 mL of anhydrous acetonitrile cooled to 0° C., under argon. After 2 h at 0° C., add 1.54 g of copper dibromide and stir the suspension obtained for 1 h 30 min at 65° C. After cooling, distribute the reaction mixture in 100 mL of EtOAc/water 1:1 mixture. Wash the organic phase with 3×50 mL of water and 50 mL of brine, then dry over Na$_2$SO$_4$ and concentrate under reduced pressure. Purify the residue obtained by silica gel column chromatography, eluting with a cyclohexane/EtOAc gradient from 0 to 30% of EtOAc. After concentration under reduced pressure, we obtain 645 mg of methyl 6-[3-(benzyloxy)-4-chlorophenyl]-5-bromopyrazine-2-carboxylate in the form of yellow wax.

Yield=43%

19.6. Methyl 6-[3-(benzyloxy)-4-chlorophenyl]-5-(2-methylphenyl)pyrazine-2-carboxylate According to the method described in example 4.5, Suzuki coupling effected between 545 mg (1.26 mmol) of methyl 6-[3-(benzyloxy)-4-chlorophenyl]-5-bromopyrazine-2-carboxylate and 205 mg (1.51 mmol) of 2-methylphenylboronic acid leads to 430 mg of methyl 6-[3-(benzyloxy)-4-chlorophenyl]-5-(2-methylphenyl)pyrazine-2-carboxylate in the form of wax.

Yield=76%

19.7. 1-({[6-{4-Chloro-3-[3-(dimethylamino)propoxy]phenyl}-5-(2-methylphenyl)pyrazin-2-yl]carbonyl}amino)cyclohexanecarboxylic acid hydrochloride According to the debenzylation/O-alkylation/saponification/peptide coupling steps described in examples 4.6, 1.6, 1.7 and 9, starting from 485 mg (1.09 mmol) of methyl 6-[3-(benzyloxy)-4-chlorophenyl]-5-(2-methylphenyl)pyrazine-2-carboxylate, we obtain 154 mg of 1-({[6-{4-chloro-3-[3-(dimethylamino)propoxy]phenyl}-5-(2-methylphenyl)pyrazin-2-yl]carbonyl}amino)cyclohexanecarboxylic acid hydrochloride in the form of white powder.

Yield=20%

M.p. (° C.)=162

M C$_{30}$H$_{35}$ClN$_4$O$_4$=550; M+H=551

$^1$H NMR (ppm, d6-DMSO, 400 MHz): 10.40 (s, 1H); 9.15 (s, 1H); 8.40 (s, 1H); 7.40 (d, 1H); 7.30 (m, 5H); 7.10 (dd, 1H); 3.85 (t, 2H); 3.15 (m, 2H); 2.75 (d, 6H); 1.95 (s, 3H); 2.3-1.3 (m, 12H).

EXAMPLE NO. 20

1-({[3-amino-6-{4-chloro-3-[3-(dimethylamino)propoxy]phenyl}-5-(2-methylphenyl)pyrazin-2-yl]carbonyl}amino)cyclohexanecarboxylic acid hydrochloride (compound No. 129)

20.1. Methyl 3-amino-6-chloro-5-(2-methylphenyl)pyrazine-2-carboxylate

Put 5 g (22.5 mmol) of methyl 3-amino-5,6-dichloropyrazine-2-carboxylate, 3.2 g (23.65 mmol) of 2-methylphenyl boronic acid in 45 mL of anhydrous toluene in a screw-top bottle. After dissolution, add 34 mL (67.6 mmol) of a 2N aqueous solution of sodium carbonate and degas the two-phase mixture for 30 min by bubbling with argon. Then add 1.3 g (1.13 mmol) of Pd(PPh$_3$)$_4$ and stir the reaction mixture vigorously at 110° C. for 48 h. After cooling, distribute the solution in 500 mL of EtOAc/brine 1:1 mixture and extract the aqueous phase again with 4×50 mL of EtOAc. Combine the organic phases, dry over Na$_2$SO$_4$ and concentrate under reduced pressure. Purify the residue obtained by silica gel column chromatography, eluting with a cyclohexane/EtOAc gradient from 0 to 20% of EtOAc. After concentration under reduced pressure, we obtain 2 g of methyl 3-amino-6-chloro-5-(2-methylphenyl)pyrazine-2-carboxylate in the form of yellow wax.

Yield 50%

20.2. Methyl 3-amino-6-[3-(benzyloxy)-4-chlorophenyl]-5-(2-methylphenyl)pyrazine-2-carboxylate According to the method described previously (example 20.1), Suzuki coupling effected between 1.7 g (6.12 mmol) of methyl 3-amino-6-chloro-5-(2-methylphenyl)pyrazine-2-carboxylate and 3.2 g (12.24 mmol) of methyl 5-amino-6-bromopyrazine-2-carboxylate, 1.97 g (7.51 mmol) of [3-(benzyloxy)-4-chlorophenyl]boronic acid leads to 2.7 g of methyl 3-amino-6-[3-(benzyloxy)-4-chlorophenyl]-5-(2-methylphenyl)pyrazine-2-carboxylate in the form of gum.

Yield=80%

20.3. 1-({[3-amino-6-{4-chloro-3-[3-(dimethylamino)propoxy]phenyl}-5-(2-methylphenyl)pyrazin-2-yl]carbonyl}amino)cyclohexanecarboxylic acid hydrochloride According to the debenzylation/O-alkylation/saponification/peptide coupling steps described in examples 4.6, 1.6, 1.7 and 9, starting from 263 mg (0.57 mmol) of methyl 3-amino-6-[3-(benzyloxy)-4-chlorophenyl]-5-(2-methylphenyl)pyrazine-2-carboxylate, we obtain 40 mg of 1-({[3-amino-6-{4-chloro-3-[3-(dimethylamino)propoxy]phenyl}-5-(2-methylphenyl)pyrazin-2-yl]carbonyl}amino)cyclohexanecarboxylic acid hydrochloride in the form of white powder.

Yield=12.5%

M.p. (° C.)=138

$MC_{30}H_{36}ClN_5O_4$=565; M+H=566

$^1$H NMR (ppm, d6-DMSO, 400 MHz): 12.40 (s, 1H); 10.1 (s, 1H); 8.30 (s, 1H); 7.55 (s, 2H); 7.30 (q, 1H); 7.20 (m, 4H); 7.05 (s, 1H); 6.85 (d, 1H); 3.80 (t, 2H); 3.10 (m, 2H); 2.70 (s, 6H); 2.15 (d, 2H); 2.05 (m, 2H); 1.95 (s, 3H); 1.75 (t, 2H); 1.55 (m, 3H); 1.40 (m, 2H); 1.25 (m, 1H).

EXAMPLE NO. 21

1-({[6-{4-Chloro-3-[3-(dimethylamino)propoxy]phenyl}-5-(2-chloro-5-ethoxyphenyl)pyridin-2-yl]carbonyl}amino)cyclohexanecarboxylic acid hydrochloride (compound No. 105)

21.1. 4-chloro-3-iodophenol

According to the steps of reduction/Sandmeyer reaction described in examples 12.4 and 12.1 respectively, starting from 25 g (144 mmol) of 4-chloro-3-nitrophenol we obtain 24 g of 4-chloro-3-iodophenol in the form of oil.

Yield=66%

21.2. 1-chloro-2-iodo-4-ethoxybenzene

Add 2 g (14.5 mmol) of $K_2CO_3$ and 1.16 mL (14.5 mmol) of iodoethane to a solution of 2.45 g (9.6 mmol) of 4-chloro-3-iodophenol in 30 mL of DMF. Heat the reaction mixture at 50° C. while stirring for 3 h, then distribute in 200 mL of ether/water 1:1 mixture. Wash the organic phase with 3×50 mL of water then dry over $Na_2SO_4$ and concentrate under reduced pressure. We obtain 2.38 g of 1-chloro-2-iodo-4-ethoxybenzene in the form of oil.

Yield=87%

21.3. (2-Chloro-5-ethoxyphenyl)boronic acid

Add, dropwise, 5.5 mL (8.8 mmol) of a 1.6N solution of butyllithium in hexane in the space of 30 min to a solution of 2.38 g (8.4 mmol) of 1-chloro-2-iodo-4-ethoxybenzene in 50 mL of anhydrous THF cooled under argon to −78° C. After 2 h at −70° C., add 1.74 g (9.2 mmol) of triisopropyl borate and stir the reaction mixture for 3 h at room temperature, then distribute in 200 mL of EtOAc/HCl aq 5N 1:1 mixture. Wash the organic phase with 50 mL of water, dry over $Na_2SO_4$ and concentrate under reduced pressure. Purify the residue obtained by silica gel column chromatography, eluting with a DCM/methanol gradient from 0 to 10% of methanol. After concentration under reduced pressure, we obtain 990 mg of (2-chloro-5-ethoxyphenyl)boronic acid, in the form of oil.

Yield=59%

21.4. Methyl 5-(2-chloro-5-ethoxyphenyl)-6-{4-chloro-3-[(4-methoxybenzyl)oxy]phenyl}pyridine-2-carboxylate According to the method described in example 4.5, the Suzuki reaction effected between 452 mg (2.26 mmol) of (2-chloro-5-ethoxyphenyl)boronic acid and 1 g (1.88 mmol) of methyl 6-{4-chloro-3-[(4-methoxybenzyl)oxy]phenyl}-5-{[(trifluoromethyl)sulphonyl]oxy}pyridine-2-carboxylate (obtained in 3 stages from 1-chloro-4-iodo-2-[(4-methoxybenzyl)oxy]benzene according to the borylation/Suzuki coupling/triflate steps described in examples 4.2, 4.3 and 4.4 respectively) leads to 700 mg of methyl 5-(2-chloro-5-ethoxyphenyl)-6-{4-chloro-3-[(4-methoxybenzyl)oxy]phenyl}pyridine-2-carboxylate in the form of oil.

Yield=70%

21.5. Methyl 5-(2-chloro-5-ethoxyphenyl)-6-(4-chloro-3-hydroxyphenyl)pyridine-2-carboxylate Add 1 mL (13 mmol) of trifluoroacetic acid to a solution of 700 mg (1.3 mmol) of methyl 5-(2-chloro-5-ethoxyphenyl)-6-{4-chloro-3-[(4-methoxybenzyl)oxy]phenyl}pyridine-2-carboxylate in 10 mL of DCM stirred at 0° C. Stir the reaction mixture for 2 h at 20° C. then concentrate under reduced pressure. Take up the residue in 50 mL of DCM and wash with 50 mL of a saturated aqueous solution of $NaHCO_3$. Dry the organic phase over $Na_2SO_4$ and concentrate under reduced pressure. Purify the residue obtained by silica gel column chromatography, eluting with a cyclohexane/EtOAc gradient from 0 to 30% of EtOAc. After concentration under reduced pressure, we obtain 524 mg of methyl 5-(2-chloro-5-ethoxyphenyl)-6-(4-chloro-3-hydroxyphenyl)pyridine-2-carboxylate in the form of oil.

Yield=96%

21.6. 1-({[6-{4-chloro-3-[3-(dimethylamino)propoxy]phenyl}-5-(2-chloro-5-ethoxyphenyl)pyridin-2-yl]carbonyl}amino)cyclohexanecarboxylic acid hydrochloride According to the O-alkylation/saponification/peptide coupling steps described in examples 1.6, 1.7 and 9, starting from 524 mg (1.25 mmol) of methyl 6-{4-chloro-3-[(4-methoxybenzyl)oxy]phenyl}-5-{[(trifluoromethyl)sulphonyl]oxy}pyridine-2-carboxylate, we obtain 125 mg of 1-({[6-{4-chloro-3-[3-(dimethylamino)propoxy]phenyl}-5-(2-chloro-5-ethoxyphenyl)pyridin-2-yl]carbonyl}amino)cyclohexanecarboxylic acid hydrochloride in the form of white powder.

Yield=18%

M.p. (° C.)=160

$MC_{32}H_{37}Cl_2N_3O_5$=613; M+H=614

$^1$H NMR (ppm, d6-DMSO, 400 MHz): 8.45 (s, 1H); 8.10 (d, 1H); 8.00 (d, 1H); 7.40 (d, 2H); 7.35 (s, 1H); 7.00 (m, 3H); 4.05 (m, 2H); 3.95 (m, 2H); 3.20 (m, 2H); 2.80 (s, 6H); 2.20 (d, 2H); 2.15 (m, 2H); 1.85 (t, 2H); 1.65 (m, 3H); 1.45 (m, 2H); 1.35 (m, 1H); 1.30 (t, 3H).

The chemical structures and physical properties of some examples of compounds according to the invention are shown in the following table.

TABLE I

TABLE OF COMPOUNDS

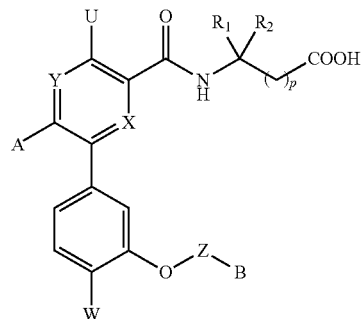
(I)

Some of the compounds presented below are in the form of hydrochloride.

| No. | A | Z | B | p | $R_1$ | $R_2$ | W | X | Y | U | Melting point (° C.) |
|---|---|---|---|---|---|---|---|---|---|---|---|
| 1 | MeO, 2-Me, 3-OMe phenyl | $(CH_2)_3$ | $NMe_2$ | 0 | | adamantyl | Cl | N | CH | H | 175 |
| 2 | MeO, 2-Me, 3-OMe phenyl | $(CH_2)_3$ | $NMe_2$ | 0 | | indanyl | Cl | N | CH | H | >200 |
| 3 | MeO, 2-Me, 3-OMe phenyl | $(CH_2)_3$ | $NMe_2$ | 0 | | cyclopentyl | Cl | N | CH | H | >200 |
| 4 | MeO, 2-Me, 3-OMe phenyl | $(CH_2)_3$ | $NMe_2$ | 0 | | norbornyl | Cl | N | CH | H | >200 |
| 5 | MeO, 2-Me, 3-OMe phenyl | $(CH_2)_3$ | $NMe_2$ | 0 | $CH_2$-phenyl | H | Cl | N | CH | H | 164 |
| 7 | MeO, 2-Me, 3-OMe phenyl | $(CH_2)_3$ | $NMe_2$ | 1 | $CH(Me)_2$ | H | Cl | N | CH | H | 202 |
| 8 | MeO, 2-Me, 3-OMe phenyl | $(CH_2)_3$ | $NMe_2$ | 1 | $CH_2$-phenyl | H | Cl | N | CH | H | 166 |

TABLE I-continued

TABLE OF COMPOUNDS

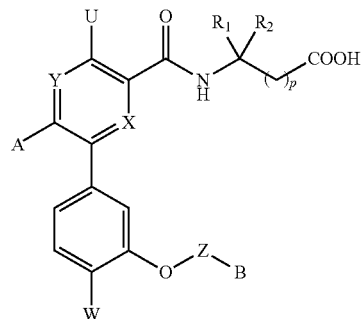

(I)

Some of the compounds presented below are in the form of hydrochloride.

| No. | A | Z | B | p | R₁ | R₂ | W | X | Y | U | Melting point (° C.) |
|---|---|---|---|---|---|---|---|---|---|---|---|
| 9 | MeO-(2-Me-3-OMe-phenyl) | (CH₂)₃ | NMe₂ | 1 | 3-indolylmethyl (CH₂-indole) | H | Cl | N | CH | H | 170 |
| 10 | MeO-(2-Me-3-OMe-phenyl) | (CH₂)₃ | NMe₂ | 0 | phenyl | H | Cl | N | CH | H | >200 |
| 11 | MeO-(2-Me-3-OMe-phenyl) | (CH₂)₃ | NMe₂ | 1 | cyclohexyl | H | Cl | N | CH | H | >200 |
| 12 | MeO-(2-Me-3-OMe-phenyl) | (CH₂)₃ | NMe₂ | 0 | cyclohexyl | | Cl | N | CH | H | >200 |
| 13 | MeO-(2-Me-3-OMe-phenyl) | (CH₂)₃ | NMe₂ | 0 | CH₂-phenyl | CH₃ | Cl | N | CH | H | >200 |
| 14 | MeO-(2-Me-3-OMe-phenyl) | (CH₂)₃ | NMe₂ | 0 | CH(Me)₂ | CH₃ | Cl | N | CH | H | >200 |
| 15 | MeO-(2-Me-3-OMe-phenyl) | (CH₂)₀ | 3-methyl-1-methylpyrrolidinyl | 0 | adamantyl | | Cl | N | CH | H | 215 |

TABLE I-continued

TABLE OF COMPOUNDS

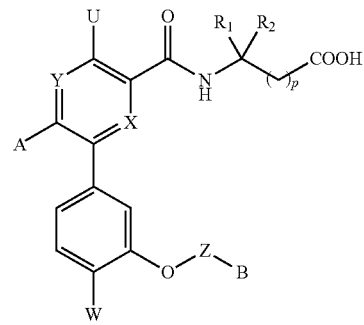
(I)

Some of the compounds presented below are in the form of hydrochloride.

| No. | A | Z | B | p | R₁ | R₂ | W | X | Y | U | Melting point (° C.) |
|---|---|---|---|---|---|---|---|---|---|---|---|
| 16 | MeO, OMe (2,3-dimethoxyphenyl) | (CH₂)₀ | 4-methyl-N-methylpiperidine | 0 | | adamantyl | Cl | N | CH | H | 231 |
| 17 | MeO (2-methoxyphenyl) | (CH₂)₃ | NMe₂ | 0 | | adamantyl | Cl | N | CH | H | 184 |
| 18 | Me (2-methylphenyl) | (CH₂)₃ | NMe₂ | 0 | | adamantyl | Cl | N | CH | H | 224 |
| 19 | MeO, OMe | (CH₂)₀ | 3-methyl-N-ethylpyrrolidine | 0 | | adamantyl | Cl | N | CH | H | 217 |
| 20 | MeO, OMe | (CH₂)₂ | NMe₂ | 0 | | adamantyl | Cl | N | CH | H | 219 |
| 21 | phenyl | (CH₂)₃ | NMe₂ | 0 | | adamantyl | Cl | N | CH | H | 192 |
| 22 | Cl (2-chlorophenyl) | (CH₂)₃ | NMe₂ | 0 | | adamantyl | Cl | N | CH | H | 214 |

TABLE I-continued

TABLE OF COMPOUNDS

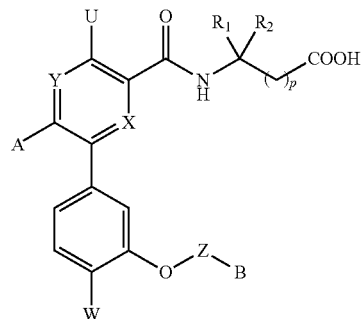

(I)

Some of the compounds presented below are in the form of hydrochloride.

| No. | A | Z | B | p | R₁ | R₂ | W | X | Y | U | Melting point (° C.) |
|---|---|---|---|---|---|---|---|---|---|---|---|
| 23 | 1-methyl-2-pyrrolidinone | (CH₂)₃ | NMe₂ | 0 | | adamantyl | Cl | N | CH | H | 199 |
| 24 | 2,3-dimethoxytoluene | (CH₂)₃ | NEt₂ | 0 | | adamantyl | Cl | N | CH | H | 189 |
| 25 | 2,3-dimethoxytoluene | (CH₂)₃ | NMe₂ | 0 | | bicyclooctyl | Cl | N | CH | H | 197 |
| 26 | 4-methylpyridine | (CH₂)₃ | NMe₂ | 0 | | adamantyl | Cl | N | CH | H | 219 |
| 27 | 2-methylpyridine | (CH₂)₃ | NMe₂ | 0 | | adamantyl | Cl | N | CH | H | 209 |
| 28 | 2,3-dimethoxytoluene | (CH₂)₃ | NMe₂ | 1 | CH(Me)₂ | H | Cl | CH | CH | H | 152 |
| 29 | Me-toluene | (CH₂)₃ | NMe₂ | 1 | CH(Me)₂ | H | Cl | CH | N | H | 139 |

TABLE I-continued

TABLE OF COMPOUNDS

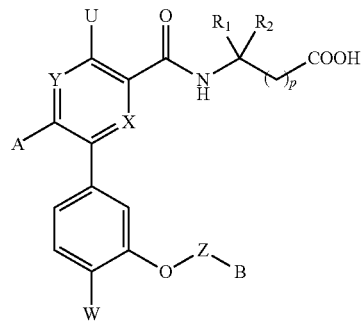
(I)

Some of the compounds presented below are in the form of hydrochloride.

| No. | A | Z | B | p | R$_1$ | R$_2$ | W | X | Y | U | Melting point (° C.) |
|---|---|---|---|---|---|---|---|---|---|---|---|
| 30 | o-Me-phenyl | (CH$_2$)$_3$ | NMe$_2$ | 0 | OH | 3-hydroxybenzyl (CH$_2$-C$_6$H$_4$-OH), H | Cl | N | CH | H | 160 |
| 31 | o-Me-phenyl | (CH$_2$)$_2$ | 2-methyl-1-methylpyrrolidinyl | 0 | adamantyl | | Cl | N | CH | H | 175 |
| 32 | o-Me-phenyl | (CH$_2$)$_2$ | 2-methyl-1-methylpiperidinyl | 0 | adamantyl | | Cl | N | CH | H | 160 |
| 33 | o-Me-phenyl | (CH$_2$)$_3$ | NMe$_2$ | 1 | cyclohexyl | | Cl | N | CH | H | 168-170 |
| 34 | o-Me-phenyl | (CH$_2$)$_3$ | NMe$_2$ | 0 | cyclohexyl | | Cl | N | CH | H | 146-150 |
| 35 | o-Me-phenyl | (CH$_2$)$_3$ | NMe$_2$ | 0 | tetrahydropyranyl | | Cl | N | CH | H | >200 |
| 36 | o-Cl-phenyl | (CH$_2$)$_3$ | NMe$_2$ | 0 | cyclohexyl | | Cl | N | CH | H | 188 |

TABLE I-continued

TABLE OF COMPOUNDS

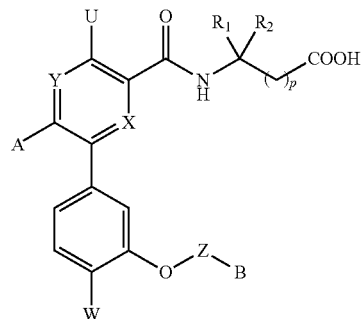
(I)

Some of the compounds presented below are in the form of hydrochloride.

| No. | A | Z | B | p | R₁ | R₂ | W | X | Y | U | Melting point (° C.) |
|---|---|---|---|---|---|---|---|---|---|---|---|
| 37 | 2-Me-phenyl | (CH₂)₃ | NMe₂ | 1 | CH(Me)₂ enantiomer (S) | H | Cl | N | CH | H | 145 |
| 38 | 2-Cl-phenyl | (CH₂)₃ | NMe₂ | 1 | CH(Me)₂ enantiomer (S) | H | Cl | N | CH | H | 162 |
| 39 | 2-Me-benzyl | (CH₂)₃ | NMe₂ | 0 | adamantyl | | Cl | N | CH | H | 195-198 |
| 40 | 2-CF₃-phenyl | (CH₂)₃ | NMe₂ | 0 | adamantyl | | Cl | N | CH | H | 178-184 |
| 41 | 2-NMe₂-phenyl | (CH₂)₃ | NMe₂ | 0 | adamantyl | | Cl | N | CH | H | 222 |
| 42 | 3-Me-pyridin-2-yl | (CH₂)₃ | NMe₂ | 0 | adamantyl | | Cl | N | CH | H | 220-222 |
| 43 | 2-Me-phenyl | (CH₂)₃ | NMe₂ | 0 | adamantyl | | CF₃ | N | CH | H | 230-232 |

TABLE I-continued

TABLE OF COMPOUNDS

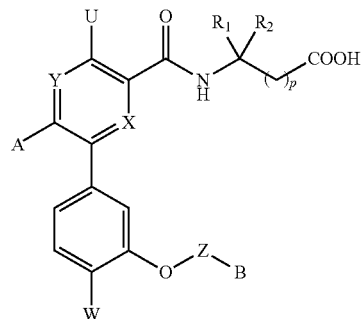
(I)

Some of the compounds presented below are in the form of hydrochloride.

| No. | A | Z | B | p | R₁ | R₂ | W | X | Y | U | Melting point (° C.) |
|---|---|---|---|---|---|---|---|---|---|---|---|
| 44 | o-Me-C₆H₄ | (CH₂)₃ | N(cyclopropyl)Me | 0 | | adamantyl | Cl | N | CH | H | 208-210 |
| 45 | o-Me-C₆H₄ | (CH₂)₃ | piperidinyl | 0 | | adamantyl | Cl | N | CH | H | >200 |
| 46 | o-Me-C₆H₄ | (CH₂)₃ | pyrrolidinyl | 0 | | adamantyl | Cl | N | CH | H | >200 |
| 47 | o-Me-C₆H₄ | (CH₂)₂ | piperidinyl | 0 | | adamantyl | Cl | N | CH | H | 185 |
| 48 | o-Me-C₆H₄ | (CH₂)₂ | pyrrolidinyl | 0 | | adamantyl | Cl | N | CH | H | 156 |
| 49 | o-Me-C₆H₄ | (CH₂)₂CHMe | NMe₂ | 0 | | adamantyl | Cl | N | CH | H | 196 |
| 50 | o-Me-C₆H₄ | CH(Me)(CH₂)₂ | NMe₂ | 0 | | adamantyl | Cl | N | CH | H | 188 |

TABLE I-continued

TABLE OF COMPOUNDS

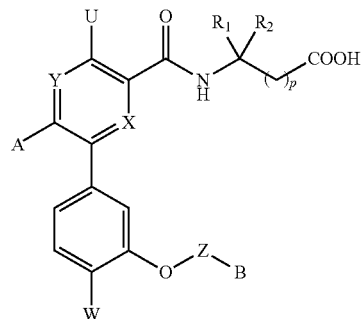

(I)

Some of the compounds presented below are in the form of hydrochloride.

| No. | A | Z | B | p | R₁ | R₂ | W | X | Y | U | Melting point (° C.) |
|---|---|---|---|---|---|---|---|---|---|---|---|
| 51 | o-tolyl (Me) | (CH₂)₃ | NMe₂ | 0 | | 4-methylcyclohexyl | Cl | N | CH | H | 216 |
| 52 | o-tolyl (Me) | (CH₂)₃ | NMe₂ | 0 | | 1-acetylpiperidin-4-yl | Cl | N | CH | H | 188-189 |
| 53 | o-tolyl (Me) | CH₂CH(OH)CH₂ enantiomer (S) | NMe₂ | 0 | | adamantyl | Cl | N | CH | H | 200 |
| 54 | o-tolyl (Me) | (CH₂)₂ | NEt₂ | 0 | | adamantyl | Cl | N | CH | H | 178 |
| 55 | 3-chloro-2-pyridyl (Cl) | (CH₂)₃ | NMe₂ | 0 | | cyclohexyl | Cl | N | CH | H | 140 |
| 56 | 3-amino-2-pyridyl (NH₂) | (CH₂)₃ | NMe₂ | 0 | | cyclohexyl | Cl | N | CH | H | >200 |
| 57 | 2-(SO₂Me)phenyl | (CH₂)₃ | NMe₂ | 0 | | cyclohexyl | Cl | N | CH | H | 190-200 |

TABLE I-continued

TABLE OF COMPOUNDS

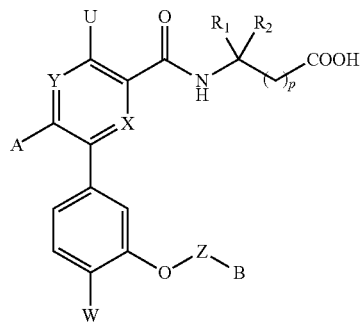

(I)

Some of the compounds presented below are in the form of hydrochloride.

| No. | A | Z | B | p | R₁ | R₂ | W | X | Y | U | Melting point (° C.) |
|---|---|---|---|---|---|---|---|---|---|---|---|
| 58 | 3-Me-2-pyridyl | (CH₂)₃ | NMe₂ | 0 | cyclohexyl* |  | Cl | N | CH | H | 174 |
| 59 | 2-Cl-phenyl | (CH₂)₃ | NMe₂ | 0 | CH(Me)₂ enantiomer (R) | H | Cl | N | CH | H | 138 |
| 60 | 2-NHAc-phenyl | (CH₂)₃ | NMe₂ | 0 | cyclohexyl* |  | Cl | N | CH | H | 196 |
| 61 | 2-Me-3-pyridyl | (CH₂)₃ | NMe₂ | 0 | cyclohexyl* |  | Cl | N | CH | H | 172 |
| 62 | 2-Me-phenyl | (CH₂)₃ | NMe₂ | 1 | CH(Me)₂ enantiomer (R) | H | Cl | N | CH | H | 145 |
| 63 | 2-Me-phenyl | CH₂CH(OH)CH₂ enantiomer (R) | NMe₂ | 0 | adamantyl* |  | Cl | N | CH | H | 200 |
| 64 | 3-Me-4-pyridyl | (CH₂)₃ | NMe₂ | 0 | cyclohexyl* |  | Cl | N | CH | H | 174 |

TABLE I-continued

TABLE OF COMPOUNDS

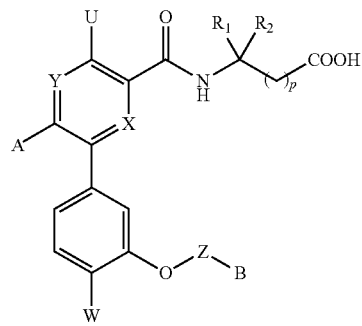
(I)

Some of the compounds presented below are in the form of hydrochloride.

| No. | A | Z | B | p | R₁ | R₂ | W | X | Y | U | Melting point (°C.) |
|---|---|---|---|---|---|---|---|---|---|---|---|
| 65 | 3,5-dichloro-2-methylpyridin-yl | (CH₂)₃ | NMe₂ | 0 | | cyclohexyl* | Cl | N | CH | H | 165 |
| 66 | 2,4-dimethylphenyl | (CH₂)₃ | NMe₂ | 0 | | cyclohexyl* | Cl | N | CH | H | 158 |
| 67 | 2-methylbenzyl (Me) | (CH₂)₃ | NMe₂ | 0 | | cyclohexyl* | Cl | N | CH | H | 150 |
| 68 | 3-chloro-5-fluoro-2-methylpyridin-yl | (CH₂)₃ | NMe₂ | 0 | | cyclohexyl* | Cl | N | CH | H | 237 |
| 69 | 3-chloro-2-methylpyridin-yl | (CH₂)₃ | NMeEt | 0 | | cyclohexyl* | Cl | N | CH | H | 156 |
| 70 | 2,6-dimethylphenyl | (CH₂)₃ | NMe₂ | 0 | | cyclohexyl* | Cl | N | CH | H | 144 |

TABLE I-continued

TABLE OF COMPOUNDS

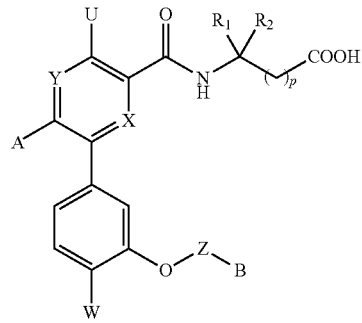
(I)

Some of the compounds presented below are in the form of hydrochloride.

| No. | A | Z | B | p | $R_1$ | $R_2$ | W | X | Y | U | Melting point (° C.) |
|---|---|---|---|---|---|---|---|---|---|---|---|
| 71 | 2-Me-phenyl | $(CH_2)_3$ | $NMe_2$ | 0 | cycloheptyl | | Cl | N | CH | H | 196 |
| 72 | 2-Cl-4-Me-phenyl | $(CH_2)_3$ | $NMe_2$ | 1 | $CH(Me)_2$ enantiomer (S) | H | Cl | N | CH | H | 157 |
| 73 | 2-Et-4-Me-phenyl | $(CH_2)_3$ | $NMe_2$ | 0 | cyclohexyl | | Cl | N | CH | H | 172 |
| 74 | 2-Cl-4-F-phenyl | $(CH_2)_3$ | $NMe_2$ | 0 | cyclohexyl | | Cl | N | CH | H | 230 |
| 75 | 1,3-diMe-pyrazol-5-yl | $(CH_2)_3$ | $NMe_2$ | 0 | cyclohexyl | | Cl | N | CH | H | 202 |
| 76 | 2-Cl-4-OMe-phenyl | $(CH_2)_3$ | $NMe_2$ | 0 | cyclohexyl | | Cl | N | CH | H | 160 |

TABLE I-continued

TABLE OF COMPOUNDS

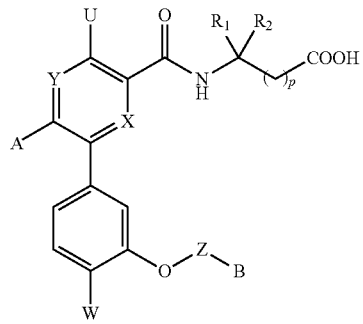
(I)

Some of the compounds presented below are in the form of hydrochloride.

| No. | A | Z | B | p | R₁ | R₂ | W | X | Y | U | Melting point (°C.) |
|---|---|---|---|---|---|---|---|---|---|---|---|
| 77 | 2-Me-phenyl | (CH₂)₃ | NMe₂ | 0 | cyclohexyl* | | CH₂CH₃ | N | CH | H | 200 |
| 78 | 4-F-2-Me-phenyl | (CH₂)₃ | NMe₂ | 0 | cyclohexyl* | | Cl | N | CH | H | 158 |
| 79 | 2-Cl-4-MeO-phenyl | (CH₂)₃ | NMe₂ | 0 | cyclohexyl* | | Cl | N | CH | H | 164 |
| 80 | 2-Me-phenyl | (CH₂)₃ | NMe₂ | 0 | cyclohexyl* | | Cl | N | N | H | 162 |
| 81 | 2-Cl-4-Me-phenyl | (CH₂)₃ | NMe₂ | 1 | cyclobutyl | H | Cl | N | CH | H | 136 |
| 82 | 2-Cl-4-Me-phenyl | (CH₂)₃ | NMe₂ | 1 | cyclopropyl | H | Cl | N | CH | H | 140 |

TABLE I-continued

TABLE OF COMPOUNDS

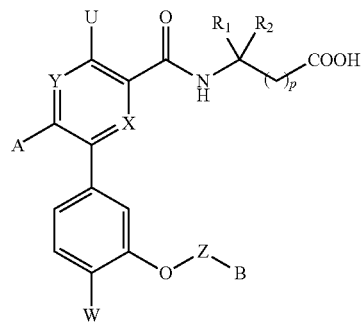

(I)

Some of the compounds presented below are in the form of hydrochloride.

| No. | A | Z | B | p | R₁ | R₂ | W | X | Y | U | Melting point (°C.) |
|---|---|---|---|---|---|---|---|---|---|---|---|
| 83 | 2,3-dimethylthiophene (Me, thiophene) | (CH₂)₃ | NMe₂ | 0 | | cyclohexyl | Cl | N | CH | H | 175 |
| 84 | 4,5-dimethylthiazole (Me, thiazole) | (CH₂)₃ | NMe₂ | 0 | | cyclohexyl | Cl | N | CH | H | 169 |
| 85 | 3-chloro-4-methyl-phenol | (CH₂)₃ | NMe₂ | 0 | | cyclohexyl | Cl | N | CH | H | 146 |
| 86 | 4-chloro-2,5-dimethylphenyl | (CH₂)₃ | NMe₂ | 0 | | cyclohexyl | Cl | N | CH | H | 163 |
| 87 | 2-(difluoromethyl)phenyl | (CH₂)₃ | NMe₂ | 0 | | cyclohexyl | Cl | N | CH | H | 117 |
| 88 | 2-(difluoromethyl)-4-methylphenyl | (CH₂)₃ | NMe₂ | 0 | | cyclohexyl | Cl | N | CH | H | 148 |

TABLE I-continued

TABLE OF COMPOUNDS

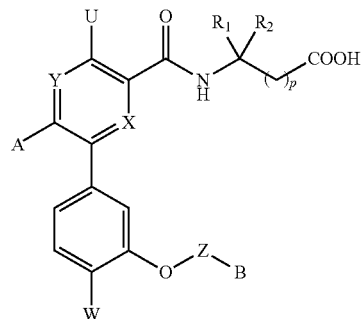

(I)

Some of the compounds presented below are in the form of hydrochloride.

| No. | A | Z | B | p | $R_1$ | $R_2$ | W | X | Y | U | Melting point (° C.) |
|-----|---|---|---|---|-------|-------|---|---|---|---|----------------------|
| 89 | 2-Me-phenyl | $(CH_2)_3$ | $NMe_2$ | 0 | oxepane* | | Cl | N | CH | H | 186 |
| 90 | 2-CN-phenyl | $(CH_2)_3$ | $NMe_2$ | 0 | cyclohexyl* | | Cl | N | CH | H | 152 |
| 91 | 2-Cl-phenyl | $(CH_2)_3$ | $NMe_2$ | 1 | $C(Me)_3$ | H | Cl | N | CH | H | 165 |
| 92 | 2-Cl-phenyl | $(CH_2)_3$ | $NMe_2$ | 1 | $C(Me)_3$ enantiomer (S) | H | Cl | N | CH | H | 170 |
| 93 | 3-Me-4-OH-phenyl | $(CH_2)_3$ | $NMe_2$ | 0 | cyclohexyl* | | Cl | N | CH | H | 134 |
| 94 | 2-F-6-Me-phenyl | $(CH_2)_3$ | $NMe_2$ | 0 | cyclohexyl* | | Cl | N | CH | H | 144 |
| 95 | 2-Me-5-OH-phenyl | $(CH_2)_3$ | $NMe_2$ | 0 | cyclohexyl* | | Cl | N | CH | H | 168 |

TABLE I-continued

TABLE OF COMPOUNDS

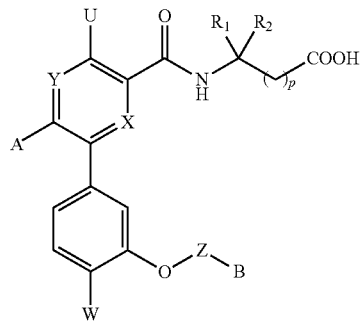

(I)

Some of the compounds presented below are in the form of hydrochloride.

| No. | A | Z | B | p | R₁ | R₂ | W | X | Y | U | Melting point (° C.) |
|---|---|---|---|---|---|---|---|---|---|---|---|
| 96 | 2-Cl, 6-F, Me-phenyl | (CH₂)₃ | NMe₂ | 0 | | cyclohexyl | Cl | N | CH | H | 147 |
| 97 | 2,6-Me, 3-F-phenyl | (CH₂)₃ | NMe₂ | 0 | | cyclohexyl | Cl | N | CH | H | 154 |
| 98 | 2-Me, 6-CH₂Me, 3-F-phenyl | (CH₂)₃ | NMe₂ | 0 | | cyclohexyl | Cl | N | CH | H | 149 |
| 99 | 2,4,5-Me-phenyl | (CH₂)₃ | NMe(CH₂)₂OH | 0 | | cyclohexyl | Cl | N | CH | H | 140 |
| 100 | 2,3-Me, 6-OH-phenyl | (CH₂)₃ | NMe₂ | 0 | | cyclohexyl | Cl | N | CH | H | 196 |
| 101 | 2,3-Me, 5,6-F-phenyl | (CH₂)₃ | NMe₂ | 0 | | cyclohexyl | Cl | N | CH | H | 157 |

TABLE I-continued

TABLE OF COMPOUNDS

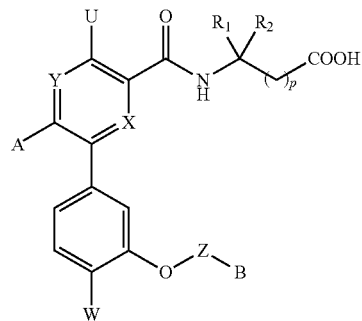

(I)

Some of the compounds presented below are in the form of hydrochloride.

| No. | A | Z | B | p | R₁ | R₂ | W | X | Y | U | Melting point (° C.) |
|---|---|---|---|---|---|---|---|---|---|---|---|
| 102 | 5,6-dimethyl-benzo[1,3]dioxole | (CH₂)₃ | NMe₂ | 0 | | cyclohexyl | Cl | N | CH | H | 195 |
| 103 | 5-methyl-1-methyl-3-methyl-pyrazole (CH₂ linker) | (CH₂)₃ | NMe₂ | 0 | | cyclohexyl | Cl | N | CH | H | 147 |
| 104 | 5-ethyl-1-methyl-3-ethyl-pyrazole (CH₂ linker) | (CH₂)₃ | NMe₂ | 0 | | cyclohexyl | Cl | N | CH | H | 152 |
| 105 | 4-chloro-3-methyl-phenyl (OCH₂Me) | (CH₂)₃ | NMe₂ | 0 | | cyclohexyl | Cl | N | CH | H | 160 |
| 106 | 3,4-dimethyl-phenyl (OCH₂Me) | (CH₂)₃ | NMe₂ | 0 | | cyclohexyl | Cl | N | CH | H | 287 |

TABLE I-continued
TABLE OF COMPOUNDS
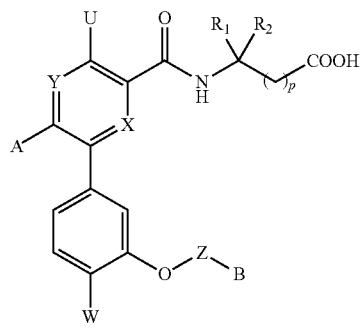
(I)
Some of the compounds presented below are in the form of hydrochloride.
| No. | A | Z | B | p | $R_1$ | $R_2$ | W | X | Y | U | Melting point (°C.) |
|---|---|---|---|---|---|---|---|---|---|---|---|
| 107 | 4-Me, 3-Me phenyl-CH2-O-Me | $(CH_2)_3$ | $NMe_2$ | 0 | | cyclohexyl | Cl | N | CH | H | 138 |
| 108 | 4-Me, 3-Me phenyl-O-CH2CH2-Me | $(CH_2)_3$ | $NMe_2$ | 0 | | cyclohexyl | Cl | N | CH | H | 152 |
| 109 | 4-Me, 3-Me phenyl-O-CH(Me)-Me | $(CH_2)_3$ | $NMe_2$ | 0 | | cyclohexyl | Cl | N | CH | H | 147 |
| 110 | 4-Me, 3-Me phenyl-O-CH2-CH(Me)-Me | $(CH_2)_3$ | $NMe_2$ | 0 | | cyclohexyl | Cl | N | CH | H | 176 |

TABLE I-continued

TABLE OF COMPOUNDS

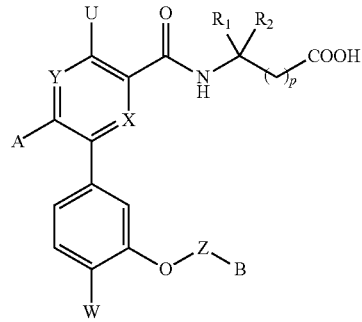

(I)

Some of the compounds presented below are in the form of hydrochloride.

| No. | A | Z | B | p | $R_1$ | $R_2$ | W | X | Y | U | Melting point (°C.) |
|---|---|---|---|---|---|---|---|---|---|---|---|
| 111 | 4-Me, 3-Me, phenyl with OCH2-cyclopropyl at 1-position | $(CH_2)_3$ | $NMe_2$ | 0 | | cyclohexyl* | Cl | N | CH | H | 185 |
| 112 | 5-Cl, 2-Me, 3-CHF2 pyridyl | $(CH_2)_3$ | $NMe_2$ | 0 | | cyclohexyl* | Cl | N | CH | H | 158 |
| 113 | 3-Cl, 4-Me, 4-NMe2 phenyl (Me2N-) | $(CH_2)_3$ | $NMe_2$ | 0 | | cyclohexyl* | Cl | N | CH | H | 172 |
| 114 | 2-Cl, 3-Me, 5-OCF3 phenyl | $(CH_2)_3$ | $NMe_2$ | 0 | | cyclohexyl* | Cl | N | CH | H | 157 |
| 115 | 2,4-diCl, methyl phenyl | $(CH_2)_3$ | $NMe_2$ | 0 | | cyclohexyl* | Cl | N | CH | H | 142 |

TABLE I-continued

TABLE OF COMPOUNDS

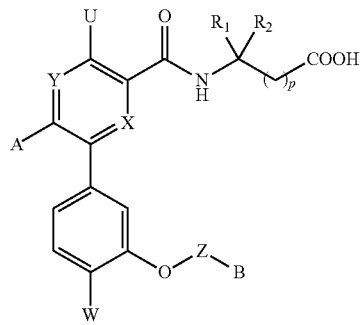
(I)

Some of the compounds presented below are in the form of hydrochloride.

| No. | A | Z | B | p | R₁ | R₂ | W | X | Y | U | Melting point (°C.) |
|---|---|---|---|---|---|---|---|---|---|---|---|
| 116 | 2-Me-phenyl | (CH₂)₃ | NMe₂ | 0 | cyclohexyl* | | Cl | N | CHOMe | H | 205 |
| 117 | 2,4-diMe-phenyl | (CH₂)₃ | NMe₂ | 1 | C(Me)₃ enantiomer (S) | H | Cl | N | CH | H | 130 |
| 118 | 2,6-diF-phenyl | (CH₂)₃ | NMe₂ | 0 | cyclohexyl* | | Cl | N | CH | H | 173 |
| 119 | 2,6-diCl-phenyl | (CH₂)₃ | NMe₂ | 0 | cyclohexyl* | | Cl | N | CH | H | 162 |
| 120 | 2-Me-4-iPr-phenyl | (CH₂)₃ | NMe₂ | 0 | cyclohexyl* | | Cl | N | CH | H | 152 |
| 121 | 4-Cl-3-Me-(MeOCH₂CH₂O)-phenyl | (CH₂)₃ | NMe₂ | 0 | cyclohexyl* | | Cl | N | CH | H | 144 |

TABLE I-continued

TABLE OF COMPOUNDS

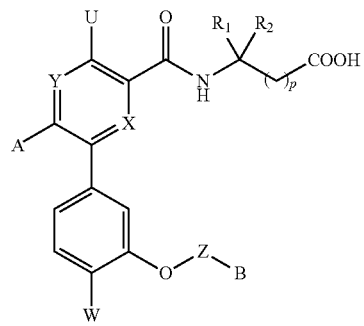

(I)

Some of the compounds presented below are in the form of hydrochloride.

| No. | A | Z | B | p | R₁ | R₂ | W | X | Y | U | Melting point (° C.) |
|---|---|---|---|---|---|---|---|---|---|---|---|
| 122 | 4-Me, 3-(OCH₂CH₂OMe)-phenyl | (CH₂)₃ | NMe₂ | 0 | | cyclohexyl* | Cl | N | CH | H | 134 |
| 123 | 2,4-diMe-phenyl | (CH₂)₃ | NMe₂ | 0 | | cyclohexyl* | Cl | N | CH | H | 135 |
| 124 | 2-Me, (CH₂OMe)-phenyl | (CH₂)₃ | NMe₂ | 0 | | cyclohexyl* | Cl | N | CH | H | 140 |
| 125 | 4-Cl, 3-Me, (OCHMeMe)-phenyl | (CH₂)₃ | NMe₂ | 0 | | cyclohexyl* | Cl | N | CH | H | 148 |
| 126 | 4-Cl, 3-Me, (OCH₂Me)-phenyl | (CH₂)₃ | NMe₂ | 0 | | cyclohexyl* | Cl | N | N | H | 122 |

TABLE I-continued
TABLE OF COMPOUNDS
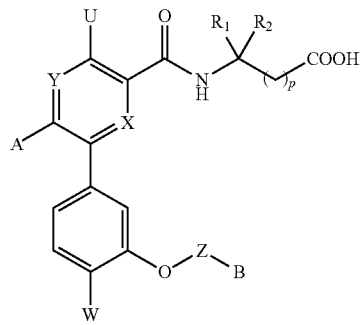
(I)
Some of the compounds presented below are in the form of hydrochloride.
| No. | A | Z | B | p | $R_1$ | $R_2$ | W | X | Y | U | Melting point (° C.) |
|---|---|---|---|---|---|---|---|---|---|---|---|
| 127 | 4-Cl, 3-Me-phenyl-O-Me (shown) | $(CH_2)_3$ | $NMe_2$ | 1 | $C(Me)_3$ enantiomer (S) | H | Cl | N | N | H | 141 |
| 128 | 4-Cl, 3-Me-phenyl with $NMe_2$ | $(CH_2)_3$ | $NMe_2$ | 0 | cyclohexyl* | | Cl | N | CH | H | 115 |
| 129 | 2-Me-phenyl | $(CH_2)_3$ | $NMe_2$ | 0 | cyclohexyl* | | Cl | N | N | $NH_2$ | 138 |
| 130 | 4-Cl, 3-Me-phenyl-O-Me | $(CH_2)_3$ | $NMe_2$ | 0 | cyclohexyl* | | Cl | N | N | $NH_2$ | 158 |

TABLE I-continued

TABLE OF COMPOUNDS

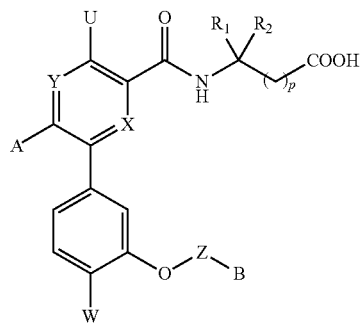

(I)

Some of the compounds presented below are in the form of hydrochloride.

| No. | A | Z | B | p | R₁ | R₂ | W | X | Y | U | Melting point (° C.) |
|---|---|---|---|---|---|---|---|---|---|---|---|
| 131 | 3-Me, 4-Me, propyl-substituted phenyl | (CH₂)₃ | NMe₂ | 0 | | cyclohexyl | Cl | N | CH | H | 144 |
| 132 | CHF₂, Me-substituted phenyl | (CH₂)₃ | NMe₂ | 0 | | cyclohexyl | Cl | N | CH | H | 160 |
| 133 | Me-phenyl | CH₂(CHF)CH₂ | NMe₂ | 0 | | cyclohexyl | Cl | N | CH | H | 158 |
| 134 | Cl, Me, OEt-substituted pyridyl | (CH₂)₃ | NMe₂ | 0 | | cyclohexyl | Cl | N | CH | H | 155 |
| 135 | Me-phenyl | (CH₂)₃ | NMe₂ | 0 | | 4,4-difluorocyclohexyl | Cl | N | CH | H | 274 |

TABLE I-continued

TABLE OF COMPOUNDS

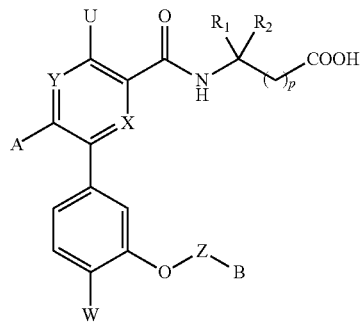
(I)

Some of the compounds presented below are in the form of hydrochloride.

| No. | A | Z | B | p | R₁ | R₂ | W | X | Y | U | Melting point (° C.) |
|---|---|---|---|---|---|---|---|---|---|---|---|
| 136 | Me (o-tolyl) | (CH₂)₃ | NMe₂ | 0 | | cyclohexyl | Cl | N | CH | NHMe | 155 |

TABLE II

TABLE OF COMPOUNDS

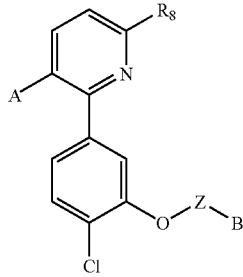
(Ibis)

R₈ represents

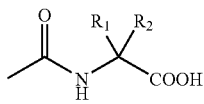

| No. | A | Z | B | R₈ | Melting point (° C.) |
|---|---|---|---|---|---|
| 137 | Me (o-tolyl) | (CH₂)₃ | NMe₂ | trans-4-acetamido-4-carboxy-cyclohexan-1-ol | 170 |
| 138 | Cl (o-chlorophenyl) | (CH₂)₃ | NMe₂ | trans-4-acetamido-4-carboxy-cyclohexan-1-ol | 166 |

TABLE II-continued

TABLE OF COMPOUNDS

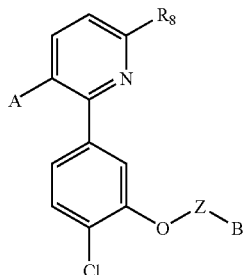

(Ibis)

$R_8$ represents

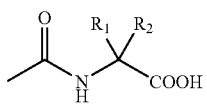

| No. | A | Z | B | $R_8$ | Melting point (° C.) |
|---|---|---|---|---|---|
| 139 | Me (o-tolyl) | $(CH_2)_3$ | $NMe_2$ | cyclohexyl with NHAc, COOH, H, OH | 180-190 |
| 140 | Me (o-tolyl) | $(CH_2)_3$ | $NMe_2$ | cyclohexyl with NHAc, COOH, OH, H | 190-200 |
| 141 | Me (o-tolyl) | $(CH_2)_3$ | $NMe_2$ | cyclohexyl with NHAc, COOH, H, OH | 160 |
| 142 | Cl (o-chlorophenyl) | $(CH_2)_3$ | $NMe_2$ | cyclohexyl with NHAc, COOH, H, OMe | >250 |
| 143 | Cl (o-chlorophenyl) | $(CH_2)_3$ | $NMe_2$ | cyclohexyl with NHAc, COOH, OMe, H | >250 |
| 144 | Me (o-tolyl) | $(CH_2)_2$ | N-methylpyrrolidinyl | cyclohexyl with NHAc, COOH, OH, H | 150 |
| 145 | Me (o-tolyl) | $(CH_2)_3$ | NMeEt | cyclohexyl with NHAc, COOH, OH, H | 160 |

103 104

TABLE II-continued

TABLE OF COMPOUNDS

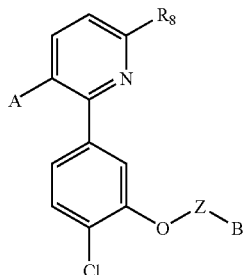
(Ibis)

$R_8$ represents

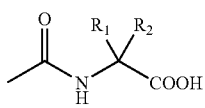

| No. | A | Z | B | $R_8$ | Melting point (° C.) |
|---|---|---|---|---|---|
| 146 | 2-Me-phenyl | $(CH_2)_4$ | $NMe_2$ | trans-4-OH, 1-COOH, 1-NHAc cyclohexyl | 148 |
| 147 | 2-Me-phenyl | $(CH_2)_3$ | $NEt_2$ | trans-4-OH, 1-COOH, 1-NHAc cyclohexyl | 158 |
| 148 | 2-(iPr)-phenyl | $(CH_2)_3$ | $NMe_2$ | trans-4-OH, 1-COOH, 1-NHAc cyclohexyl | 162 |
| 149 | 2-(CH$_2$Me)-phenyl | $(CH_2)_3$ | $NMe_2$ | trans-4-OH, 1-COOH, 1-NHAc cyclohexyl | 170 |
| 150 | 2-Me-4-Cl-phenyl | $(CH_2)_3$ | $NMe_2$ | trans-4-OH, 1-COOH, 1-NHAc cyclohexyl | 167-170 |
| 151 | 2,4-diMe-phenyl | $(CH_2)_3$ | $NMe_2$ | trans-4-OH, 1-COOH, 1-NHAc cyclohexyl | 202 |

TABLE II-continued

TABLE OF COMPOUNDS

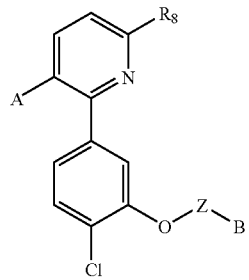
(Ibis)

$R_8$ represents

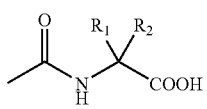

| No. | A | Z | B | $R_8$ | Melting point (° C.) |
|---|---|---|---|---|---|
| 152 | 2,4-diMe-phenyl | $(CH_2)_3$ | NMeEt | trans-4-OH-cyclohexyl-NHAc-COOH | 178 |
| 153 | 2,4-diMe-phenyl | $(CH_2)_3$ | $NEt_2$ | trans-4-OH-cyclohexyl-NHAc-COOH | 162 |
| 154 | 2,5-diMe-phenyl | $(CH_2)_3$ | $NMe_2$ | trans-4-OH-cyclohexyl-NHAc-COOH | 174 |
| 155 | 4-F-2-Me-phenyl | $(CH_2)_3$ | $NMe_2$ | trans-4-OH-cyclohexyl-NHAc-COOH | 170-175 |
| 156 | 2-Me-benzyl | $(CH_2)_3$ | NMePr | trans-4-OH-cyclohexyl-NHAc-COOH | 138 |
| 157 | 2-Me-benzyl | $(CH_2)_3$ | NMeEt | trans-4-OH-cyclohexyl-NHAc-COOH | 145 |

TABLE II-continued

TABLE OF COMPOUNDS (Ibis)

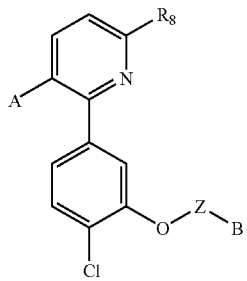

R₈ represents

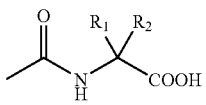

| No. | A | Z | B | R₈ | Melting point (° C.) |
|---|---|---|---|---|---|
| 158 | Me-(2-methylphenethyl) | (CH₂)₃ | NMe₂ | trans-4-acetamido-4-hydroxycyclohexane-1-carboxylic acid | 150 |
| 159 | 4-Cl-3-Me-phenyl | (CH₂)₃ | NMe₂ | trans-4-acetamido-4-hydroxycyclohexane-1-carboxylic acid | 165 |
| 160 | Me-(2-methylbenzyl) | CH₂CH(Me)CH₂ | NMe₂ | trans-4-acetamido-4-hydroxycyclohexane-1-carboxylic acid | 158 |

The compounds according to the invention have undergone pharmacological testing for determining the properties of the compounds of the invention, including in particular:
 a test in vitro of intracellular calcium mobilization (FlipR test) employing urotensin II antagonists (the compounds of the present invention) of the human GPR14 receptor,
 a function test of contraction of rat aorta rings, also employing urotensin II antagonists represented by the compounds of the present invention.

These two tests are described below:

1. FlipR (Fluorometric Imaging Plate Reader) Protocol 1.1 Purpose

The purpose is to measure the activation of the GPR14 receptor by human urotensin II.

1.2. Test Principle

GPR14 is a Gq-coupled receptor with 7 transmembrane domains. Its activation by a specific ligand causes an increase in $Ca^{2+}$ in the cell via the PLC (Phospholipase C), IP3 (Inositol-1,4,5-triphosphate) DAG (Diacylglycerol) pathway. The increase in $Ca^{2+}$ in the cell is measured by means of the Fluo4AM permeating probe (mono-excitation, mono-emission probe) which binds to free $Ca^{2+}$ and emits at 520 nm. The free probe is non-fluorescent in the absence of $Ca^{2+}$.

1.3. Protocol

Experimental Plan
 1) Seeding of the cells on D−1 (Day−1) or D−2
 2) Incorporation/loading (D0) of the probe (1 h)
 3) Addition of the products to the FlipR and measurement
 4) Addition of the ligand to the FlipR and measurement in the presence of the products
 5) Processing and exporting the data CHOGPR14Cells The cells are cultivated in complete medium in Flask T225. For the experiments, the cells are transplanted in 200 μl of culture medium in 96-well (black, transparent-bottom) plates at a rate of 60 000 cells/well for use on D+1 or 40 000 cells/well for use on D+2.

Incorporation of the Fluo 4 M

The Fluo-4AM is prepared at 20 mM then aliquots are taken (50 µl) and stored at −20° C. away from the light. A solution of pluronic acid at 200 mg/ml in DMSO is also prepared (it has a shelf life of one week at room temperature away from the light).

The cells are charged with the Fluo-4AM+pluronic acid mixture (aliquot 50 µl+50 µl of pluronic acid) diluted to 1/100 in the measurement buffer.

After washing the wells with 150 µl of measurement buffer (cf. annex), the cells are then charged as follows:
- distribution of 100 µl of measurement buffer in each well
- addition of 10 µl of the Fluo-4AM+pluronic acid mixture diluted to 1/100.

The cells are incubated for 1 h at 37° C. away from the light, in an incubator in the presence of 5% $CO_2$.

The cells are then washed 3 times with 150 µl of measurement buffer to remove the excess of the probe. A volume of 150 µl of buffer is added to each well at the end of washing.

After incubating the plates for 20 min at room temperature away from the light, they are placed in the FlipR for measurement of fluorescence.

The level of basic incorporation of the Fluo-4 is checked for each plate (sd<10%) before the first injection.

After stabilization of the basic signal, the GPR14 inhibiting compounds are injected by the FlipR under a volume of 50 µl from a dilution plate effected by Biomek 2000 in measurement buffer. Urotensin II (3 nM final, concentration equal to the $EC_{50}$) is added under a volume of 50 µl by the FlipR on the cells from a stock plate at 15 nM diluted in the measurement buffer. Data recording is carried out continuously throughout the experiment.

1.4. Data Analysis

For each plate, the basic fluorescence before injection of the compounds is standardized by the "spatial uniformity correction" function of the FlipR. The values of fluorescence measured just before injection of urotensin II (min) and those of the fluorescence measured at the peak of the effect of urotensin II (max) are exported under Excel. In each plate, a series of wells is treated with urotensin alone in the absence of inhibitor compound. The min and max fluorescence values for these wells are averaged for defining 100% effect of urotensin II.

The percentage inhibition calculated for each concentration of inhibitor is calculated as follows:
- for each well with Uro II (urotensin II)+inhibitor, calculation of the delta product value=max−min
- for the well with Uro II alone, calculation of the value delta Uro II (average max−average min)

The percentage inhibition for each concentration of product is calculated as follows:

Inhibition(%)=100×(delta Uro *II*−delta product)/delta Uro *II*

1.5. Annex

Composition of the measurement buffer (in demineralized water, to be prepared when required)

|  | Qsf 500 mL | QSF 1 L | QSF 2 L |
|---|---|---|---|
| HBSS | 50 mL | 100 mL | 200 mL |
| $MgSO_4$ 19.72 g/L | 5 mL | 10 mL | 20 mL |
| Hepes | 2.38 g | 4.76 g | 9.52 g |
| $Na_2CO_3$ 35 g/L | 5 mL | 10 mL | 20 mL |
| $CaCl_2$ 14.7 g/L | 5 mL | 10 mL | 20 mL |
| BSA 10% | 50 mL | 100 mL | 200 mL |

HBSS = Hanks' Balanced Salt Solution
BSA = Bovine Serum Albumin

The various saline solutions can be stored for 2 months at 4° C.

Adjust the volume of $H_2O$ and add probenecid dissolved in 1N sodium hydroxide

| +Probenecid | 0.355 g in 5 mL of 1N NaOH | 0.71 g in 10 mL of 1N NaOH | 1.42 g in 20 mL of 1N NaOH |
|---|---|---|---|

Check for pH 7.4.

1.6. Equipment and Materials

Human urotensin II (Bachem H-4768)
Fluo-4AM (Molecular Probes (F14202 5×1 mg)
Probenecid (Sigma P8761 100 g)
Pluronic acid (Molecular Probes P6867)
HBSS 10× (Gibco 14185-045)
HEPES (acid) (Sigma H3375)
Sodium carbonate (Sigma S7795) $Na_2CO_3$
Magnesium sulphate (Sigma M7774) $MgSO_4$
Calcium chloride (Sigma C5080) $CaCl_2$
Black tips (Molecular Devices 9000-0549)
Black plates, 96-well (Beckton Dickinson 356640)
DMSO (Sigma D 5879)

1.7. Results

The compounds tested have an IC50 in the FlipR test below 10000 nM. Some of these compounds have an IC50 in the FlipR test below 100 nM. For example, compounds No. 18, 34, 37, 58, 61, 65, 66, 67, 70, 71, 75, 79, 120, 123, 129 in the table have IC50 of 19, 25, 72, 28, 9, 32, 4.2, 13, 32, 24, 21, 31, 16, 4.2 and 15 nM, respectively.

2. Contraction of Rat Aorta 2.1. Protocol

Male Sprague-Dawley rats (400-500 g; C. River, France) are anaesthetized with 6% sodium pentobarbital (Ceva Santé Animate) by intraperitoneal injection (0.4-0.5 ml), and then euthanized by exsanguination. The aortas are removed, washed and, after removing the endothelium, are cut into 4 rings of about 0.2-0.3 cm. Each fragment is placed in a container for isolated organs, containing 20 mL of Krebs solution with the following composition (mM): NaCl 118; KCl 4.7; $MgCl_2$ 1.2; $CaCl_2$ 2.6; $NaHCO_3$ 25; glucose 11.1; (pH=7.4).

The tissue, maintained at 37° and aerated with a stream of carbogen (95% $O_2$-5% $CO_2$), is connected to a Grass FT03 isometric sensor under a basic strain of 2 g, and to a Gould series 6600 amplifier for recording the variations in strain. Data acquisition is effected automatically on an HP Compaq PC using IOX software (version 2.2) from the company Emka.

After stabilization for 60 min, the viability of the preparation is tested by prestimulation with 60 mM of KCl. This contraction is repeated a second time and the strain that developed will serve as reference (100%) for standardizing the response to urotensin II.

The curve of concentration v. contractile response to urotensin II is then constructed cumulatively until a maximum response is obtained.

A single concentration-response curve is recorded owing to the desensitization effects induced by urotensin II.

The antagonists or the vehicle (DMSO 0.15% maximum) are added to the container 30 min before the agonist.

2.2. Compound

Human urotensin II is obtained from Bachem Ltd (UK) and is dissolved in 0.1% of BSA.

2.3. Data Analysis

The responses are expressed as percentage of the maximum contraction observed with KCl. The results represent the mean±sem of the individual responses. N corresponds to the number of animals per batch.

Analysis of the sigmoid curves using the Everstat software (De Lean A, Munson P J, Rodbard D., Am J Physiol 1978; 235(2): E97-102.) permitted the $EC_{50}$ (concentration producing 50% of the maximum response) and the $E_{max}$ (maximum effect) to be determined.

To evaluate the potency of the antagonists based on a single concentration, the pKb were calculated according to the equation: pKb=−log [antagonist]M+log(concentration-ratio−1) (Furchgott R F, Blaschko H, Muscholl E, editors. Handbook of Exp Pharmacol, Catecholamines, Springer, Berlin Heidelberg N.Y.; 1972; 33:283-335) where concentration-ratio is the $EC_{50}$ of the agonist in the presence of the antagonist divided by the $EC_{50}$ of the agonist in the absence of the antagonist.

If several concentrations of antagonist are tested, the $pA_2$ (±confidence limits) is calculated by the Schild plot method (Arunlakshana O and Schild H O, Br J Pharmacol, 1959; 14:48-58).

2.4. Results

The compounds tested have a pKb between 5.5 and 8.15. As examples, compounds No. 18, 34, 37, 58, 61, 65, 66, 67, 70, 71, 75, 79, 120, 123, 129 in the table have a pKb of 6.5; 7.1; 7.5; 6.6; 7.1; 6.5; 6.7; 6.7; 6.2; 6.3; 6.6; 6.8; 7.1; 6.5; 6.8 respectively.

The compounds according to the invention can therefore be used for the preparation of medicinal products, in particular of medicinal products that are inhibitors of the urotensin II receptors.

Thus, according to another of its aspects, the invention relates to medicinal products that comprise a compound of formula (I), or a salt of addition of the latter to a pharmaceutically acceptable acid of the compound of formula (I).

These medicinal products find application in therapeutics, notably in the treatment and/or prevention of congestive heart failure, ischaemic heart disease, myocardial infarction, cardiac hypertrophy and fibrosis, coronary diseases and atherosclerosis, systemic arterial hypertension, pulmonary hypertension, portal hypertension, post-angioplasty restenosis, renal failure and more particularly acute and chronic renal failure of diabetic and/or hypertensive origin, diabetes, inflammation in general, fibrosis in general and aneurysms.

These medicinal products also find application in therapeutics, in the treatment and/or prevention of disorders of the central nervous system, including notably neurodegenerative diseases, cerebrovascular accidents, stress, anxiety, aggressiveness, depression, schizophrenia, or sleep disorders.

Medicinal products comprising compounds that are antagonists of urotensin II such as the compounds according to the invention also find application in therapeutics, in the treatment and/or prevention of vomiting.

These medicinal products also find application in therapeutics in the treatment of some cancers.

These medicinal products also find application in therapeutics, in the treatment and/or prevention of asthma and respiratory diseases.

According to another of its aspects, the present invention relates to pharmaceutical compositions comprising, as active principle, a compound according to the invention.

These pharmaceutical compositions contain an effective dose of at least one compound according to the invention, or a pharmaceutically acceptable salt of said compound, as well as at least one pharmaceutically acceptable excipient.

Said excipients are selected according to the pharmaceutical form and the desired method of administration, from the usual excipients that are known by a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its salt, can be administered in unit dosage form, mixed with conventional pharmaceutical excipients, to animals and to humans for the prophylaxis or treatment of the aforementioned disorders or diseases.

The appropriate unit dosage forms comprise the forms for administration by the oral route, such as tablets, soft or hard capsules, powders, granules and oral solutions or suspensions, forms for sublingual, buccal, intratracheal, intraocular, intranasal administration, administration by inhalation, forms for topical, transdermal, subcutaneous, intramuscular or intravenous administration, forms for rectal administration, and implants. For topical application, compounds according to the invention can be used in creams, gels, ointments or lotions.

As an example, a unit dosage form of a compound according to the invention in the form of a tablet can comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropyl methylcellulose | 2.25 mg |
| Magnesium stearate | 3.0 mg |

According to another of its aspects, the present invention also relates to a method of treatment of the above-mentioned pathologies that comprises the administration, to a patient, of an effective dose of a compound according to the invention, or one of its pharmaceutically acceptable salts.

As used herein, the following definitions apply:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

The invention claimed is:

1. A compound according to formula (I):

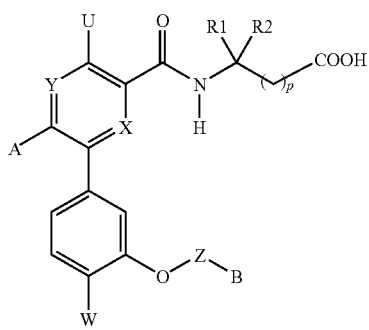

in which:
X and Y represent, independently of one another, a nitrogen atom or a —CR3-group, where R3 represents a hydrogen or halogen atom or an alkyl or alkoxy group;
U represents a hydrogen atom or a group NHR7, where R7 is a hydrogen atom or an alkyl group;
A represents an aryl, heteroaryl or heterocycloalkyl group optionally substituted;
W represents a halogen atom, an alkyl group or a haloalkyl group;
Z represents a bond, a cycloalkylene group or an alkylene group optionally substituted with one or more groups selected from a halogen atom and the alkyl, hydroxy and alkoxy groups;
B represents:
either a group —NR4R5, where R4 and R5 represent, independently of one another, an alkyl, cycloalkyl, hydroxyalkyl or fluoroalkyl group, or alternatively R4 and R5 form, with the nitrogen atom to which they are attached, a 5- or 6-membered ring, such as a pyrrolidinyl or piperidinyl ring, optionally substituted with an alkyl group,
or a heterocycle of the following formula:

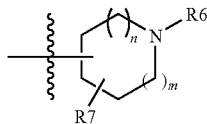

where m and n represent, independently of one another, 0, 1 or 2, and where R6 and R7 represent, independently of one another, a hydrogen atom or an alkyl or cycloalkyl group;
R1 and R2 represent:
either, independently of one another, a hydrogen atom or an alkyl, cycloalkyl, phenyl, benzyl or —CH2-indolyl group, these groups being optionally substituted with one or more groups selected from halogen atoms and the alkyl, fluoroalkyl, alkoxy, hydroxy and —O—CO-alkyl groups, at least one of R1 or R2 being different from a hydrogen atom,
or R1 and R2 together form, with the carbon atom to which they are attached, a mono- or polycyclic system selected from: cycloalkyl, indanyl, tetrahydropyranyl, piperidine, tetrahydronaphthyl, bicyclo[2.2.1]heptyl, bicyclo[3.3.1]nonyl and adamantyl, said mono- or polycyclic system being optionally substituted, in any position (including on a nitrogen atom, if applicable) with one or more groups selected from a halogen atom and the alkyl, fluoroalkyl, hydroxy, alkoxy, —O—CO-alkyl and acyl groups;
p represents an integer equal to 0 or 1;
or an enantiomer, diastereomer, racemate, or pharmaceutically acceptable salt thereof.

2. The compound of claim 1, in which X and Y represent, independently of one another, a nitrogen atom or a —CR3-group, where R3 represents a hydrogen or halogen atom or an alkyl or alkoxy group;
or an enantiomer, diastereomer, racemate, or pharmaceutically acceptable salt thereof.

3. The compound of claim 1, in which U represents a hydrogen atom or a group NHR7, where R7 is a hydrogen atom or an alkyl group;
or an enantiomer, diastereomer, racemate, or pharmaceutically acceptable salt thereof.

4. The compound of claim 1, in which A represents an aryl, heteroaryl or heterocycloalkyl group selected from the phenyl, benzodioxolyl, thienyl, thiazolyl, pyridinyl, pyrimidinyl, pyridazinyl, pyrazinyl, pyrazolyl and pyrrolidinone groups, said aryl, heteroaryl or heterocycloalkyl group being optionally substituted in any positions with one or more groups selected from a halogen atom and the cyano, alkyl, haloalkyl, hydroxy, alkoxy, —O—(CH2)$_p$—O-alkyl, haloalkoxy, —NRR', —NR—CO-alkyl, —SO— and —SO2-alkyl groups, where R and R' represent, independently of one another, a hydrogen atom or an alkyl group and p is an integer between 1 and 5;
or an enantiomer, diastereomer, racemate, or pharmaceutically acceptable salt thereof.

5. The compound of claim 1, in which W represents a halogen atom, an alkyl group or a haloalkyl group;
or an enantiomer, diastereomer, racemate, or pharmaceutically acceptable salt thereof.

6. The compound of claim 1, in which Z represents a bond, a cycloalkylene group or an alkylene group optionally substituted with one or more groups selected from a halogen atom and the alkyl, hydroxy and alkoxy groups;
or an enantiomer, diastereomer, racemate, or pharmaceutically acceptable salt thereof.

7. The compound of claim 1, in which B represents a group —NR4R5, where R4 and R5 represent, independently of one another, an alkyl, cycloalkyl, hydroxyalkyl or fluoroalkyl group, or alternatively R4 and R5 form, with the nitrogen atom to which they are attached, a 5- or 6-membered ring, such as a pyrrolidinyl or piperidinyl ring, optionally substituted with an alkyl group,
or an enantiomer, diastereomer, racemate, or pharmaceutically acceptable salt thereof.

8. The compound of claim 1, in which B represents a heterocycle of the following formula:

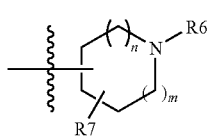

where m and n represent, independently of one another, 0, 1 or 2, and where R6 and R7 represent, independently of one another, a hydrogen atom or an alkyl or cycloalkyl group;
or an enantiomer, diastereomer, racemate, or pharmaceutically acceptable salt thereof.

9. The compound of claim 1, in which R1 and R2 represent, independently of one another, a hydrogen atom or an alkyl, cycloalkyl, phenyl, benzyl or —CH₂— indolyl group, these groups being optionally substituted with one or more groups selected from halogen atoms and the alkyl, fluoroalkyl, alkoxy, hydroxy and —O—CO-alkyl groups, at least one of R1 or R2 being different from a hydrogen atom,
or an enantiomer, diastereomer, racemate, or pharmaceutically acceptable salt thereof.

10. The compound of claim 1, in which R1 and R2 together form, with the carbon atom to which they are attached, a mono- or polycyclic system selected from: cycloalkyl, indanyl, tetrahydropyranyl, piperidine, tetrahydronaphthyl, bicyclo[2.2.1]heptyl, bicyclo[3.3.1]nonyl and adamantyl, said mono- or polycyclic system being optionally substituted, in any position (including on a nitrogen atom, if applicable) with one or more groups selected from a halogen atom and the alkyl, fluoroalkyl, hydroxy, alkoxy, —O—CO-alkyl and acyl groups;
or an enantiomer, diastereomer, racemate, or pharmaceutically acceptable salt thereof.

11. The compound of claim 1, in which:
X and Y represent, independently of one another, a nitrogen atom or a —CR3-group, where R3 represents a hydrogen atom or an alkoxy group;
U represents a hydrogen atom or a group NHR7, where R7 is a hydrogen atom or an alkyl group;
A represents an aryl, heteroaryl or heterocycloalkyl group selected from the phenyl, benzodioxolyl, thienyl, thiazolyl, pyridinyl, pyrazolyl and pyrrolidinone groups, said aryl or heteroaryl group being optionally substituted in any positions with one or more groups selected from a halogen atom and the cyano, alkyl, haloalkyl, hydroxy, alkoxy, —O—(CH₂)ₚ—O-alkyl, haloalkoxy, —NRR', —NR—CO-alkyl and —SO₂-alkyl groups, where R and R' represent, independently of one another, a hydrogen atom or an alkyl group and p is an integer between 1 and 5;
W represents a halogen atom, an alkyl group or a haloalkyl group;
Z represents a bond or an alkylene group optionally substituted with at least one group selected from a halogen atom and the alkyl and hydroxy groups;
B represents:
either a group —NR4R5, where R4 and R5 represent, independently of one another, an alkyl, hydroxyalkyl group, or alternatively R4 and R5 form, with the nitrogen atom to which they are attached, a 5- or 6-membered ring, such as a pyrrolidinyl or piperidinyl ring,
or a heterocycle of the following formula:

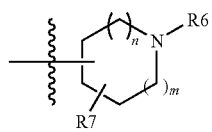

where m and n represent, independently of one another, 0, 1 or 2, and where R6 and R7 represent, independently of one another, a hydrogen atom or an alkyl or cycloalkyl group;
R1 and R2 represent:
either, independently of one another, a hydrogen atom or an alkyl, cycloalkyl, phenyl, benzyl or —CH₂-indolyl group, these groups being optionally substituted with one or more hydroxy groups, at least one of R1 or R2 being different from a hydrogen atom,
or R1 and R2 together form, with the carbon atom to which they are attached, a mono- or polycyclic system selected from: cycloalkyl, indanyl, tetrahydropyranyl, piperidine, bicyclo[2.2.1]heptyl, bicyclo[3.3.1]nonyl and adamantyl, said mono- or polycyclic system being optionally substituted, in any position (including on a nitrogen atom, if applicable) with one or more groups selected from the alkyl, hydroxy and alkoxy groups;
p represents an integer equal to 0 or 1;
or an enantiomer, diastereomer, racemate, or pharmaceutically acceptable salt thereof.

12. The compound of claim 1, in which:
X and Y represent, independently of one another, a nitrogen atom or a CH group;
A represents a phenyl, pyridinyl, or pyrrolidinone group, substituted in any positions with 1 to 2 groups selected from a halogen atom, and the alkyl, trifluoromethyl, methoxy and N,N-dimethylamine groups;
U represents a hydrogen atom or a group NHR7, where R7 is a hydrogen atom;
W represents a chlorine atom or a trifluoromethyl group;
Z represents a bond or an alkylene group optionally substituted with a methyl group;
B represents:
either a group —NR4R5, where R4 and R5 represent, independently of one another, an alkyl group or alternatively R4 and R5 form, with the nitrogen atom to which they are attached, a 5- or 6-membered ring,
or heterocycles of the following formula:

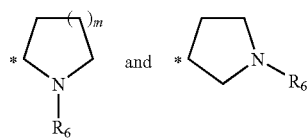

where m=1 or 2 and R6 represents an ethyl or methyl group;
R1 and R2 represent:
either, independently of one another, a hydrogen atom or an isopropyl, tertbutyl group,
or R1 and R2 together form, with the carbon atom to which they are attached, a mono- or polycyclic system selected from: cycloalkyl, tetrahydropyranyl, bicyclo[2.2.1]heptyl, bicyclo[3.3.1]nonyl and adamantyl, said cycloalkyl group being optionally substituted in positions 3 and 4 with a methyl, hydroxy or methoxy group or one or two halogen atoms, p represents 0 or 1;

or an enantiomer, diastereomer, racemate, or pharmaceutically acceptable salt thereof.

13. The compound of claim 1, in which:
X represents a nitrogen atom and Y represents a CH group;
A represents a phenyl or pyridinyl group, substituted in positions 2, 4, 5 and 6 by one or two groups selected from a halogen atom, such as chlorine or fluorine, and the alkyl groups, such as methyl, ethyl or isopropyl, trifluoromethyl, methoxy and N,N-dimethylamine;
U represents a hydrogen atom or a group NHR7, where R7 is a hydrogen atom;
W represents a chlorine atom or a trifluoromethyl group;
Z represents a bond or an ethylene, propylene or methylpropylene group;
B represents:
either a group —NR4R5, where R4 and R5 represent, independently of one another, a methyl, ethyl or propyl group or form together with the nitrogen atom to which they are attached a 5- or 6-membered ring,
or a heterocycle of the following formula:

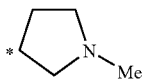

R1 and R2 represent:
either R1 is a hydrogen atom and R2 an isopropyl, tertbutyl group, the carbon atom bearing groups R1 and R2 adopting the absolute configuration S,
or R1 and R2 together form, with the carbon atom to which they are attached, a cycloalkyl, and adamantyl group, said cycloalkyl group being optionally substituted in positions 3 and 4 with a methyl, hydroxy or methoxy group;

p represents 0 or 1;
or an enantiomer, diastereomer, racemate, or pharmaceutically acceptable salt thereof.

14. The compound of claim 1 which is:
2-({[6-{4-chloro-3-[3-(dimethylamino)propoxy]phenyl}-5-(2,6-dimethoxyphenyl)pyridin-2-yl]carbonyl}amino)adamantane-2-carboxylic acid hydrochloride;
1-({[6-{4-chloro-3-[3-(dimethylamino)propoxy]phenyl}-4-methoxy-5-(2-methylphenyl)pyridin-2-yl]carbonyl}amino)cyclohexanecarboxylic acid hydrochloride;
(3S)-3-({[6-{4-chloro-3-[3-(dimethylamino)propoxy]phenyl}-5-(2,4-dimethylphenyl)pyridin-2-yl]carbonyl}amino)-4,4-dimethylpentanoic acid hydrochloride;
1-({[6-{4-chloro-3-[3-(dimethylamino)propoxy]phenyl}-5-(2,6-difluorophenyl)pyridin-2-yl]carbonyl}amino)cyclohexanecarboxylic acid hydrochloride;
1-({[6-{4-chloro-3-[3-(dimethylamino)propoxy]phenyl}-5-(5-ethoxy-2-methylphenyl)pyridin-2-yl]carbonyl}amino)cyclohexanecarboxylic acid hydrochloride;
1-({[6-{4-chloro-3-(dimethylamino)propoxy]phenyl}-5-(2,6-dichlorophenyl)pyridin-2-yl]carbonyl}amino)cyclohexanecarboxylic acid hydrochloride;
1-({[6-{4-chloro-3-[3-(dimethylamino)propoxy]phenyl}-5-(2-fluoro-6-methylphenyl)pyridin-2-yl]carbonyl}amino)cyclohexanecarboxylic acid hydrochloride;
1-[(6-{4-chloro-3-[3-(dimethylamino)propoxy]phenyl}-5-[2-methyl-5-(1-methylethyl)phenyl]pyridin-2-yl)carbonyl]amino}cyclohexanecarboxylic acid hydrochloride;
1-[(6-{4-chloro-3-[3-(dimethylamino)propoxy]phenyl}-5-[2-chloro-5-(2-methoxyethoxy)phenyl]pyridin-2-yl)carbonyl]amino}cyclohexanecarboxylic acid hydrochloride;
1-({[6-{4-chloro-3-(dimethylamino)propoxy]phenyl}-5-(2,4-dimethylphenyl)pyrazin-2-yl]carbonyl}amino)cyclohexanecarboxylic acid hydrochloride;
(3S)-3-({[6-{4-chloro-3-[3-(dimethylamino)propoxy]phenyl}-5-(2-chloro-5-ethoxyphenyl)pyrazin-2-yl]carbonyl}amino)-4,4-dimethylpentanoic acid hydrochloride;
1-[(6-{4-chloro-3-[3-(dimethylamino)propoxy]phenyl}-5-[2-(methoxymethyl)phenyl]pyridin-2-yl)carbonyl]amino}cyclohexanecarboxylic acid hydrochloride;
1-[(6-{4-chloro-3-[3-(dimethylamino)propoxy]phenyl}-5-[2-chloro-5-(1-methylethoxy)phenyl]pyridin-2-yl)carbonyl]amino cyclohexanecarboxylic acid hydrochloride;
1-({[6-{4-chloro-3-[3-(dimethylamino)propoxy]phenyl}-5-(2-chloro-5-ethoxyphenyl)pyrazin-2-yl]carbonyl}amino)cyclohexanecarboxylic acid hydrochloride;
1-{[(5-[2-chloro-5-(dimethylamino)phenyl]-6-{4-chloro-3-[3-(dimethylamino)propoxy]phenyl}pyridin-2-yl)carbonyl]amino}cyclohexanecarboxylic acid hydrochloride;
1-({[6-{4-chloro-3-[3-(dimethylamino)propoxy]phenyl}-5-(2-ethyl-6-fluorophenyl)pyridin-2-yl]carbonyl}amino)cyclohexanecarboxylic acid hydrochloride;
1-({[6-{4-chloro-3-[3-(dimethylamino)propoxy]phenyl}-5-(2-methyl-5-propylphenyl)pyridin-2-yl]carbonyl}amino)cyclohexanecarboxylic acid hydrochloride;
1-{[(6-{4-chloro-3-[3-(dimethylamino)propoxy]phenyl}-5-[2-(difluoromethyl)-4-methylphenyl]pyridin-2-yl)carbonyl]amino}cyclohexanecarboxylic acid hydrochloride;
1-{[(3-chloro-2'-{4-chloro-3-[3-(dimethylamino)propoxy]phenyl}-6-ethoxy-2,3'-bipyridin-6'-yl)carbonyl]amino}cyclohexanecarboxylic acid hydrochloride;
1-({[3-amino-6-{4-chloro-3-[3-(dimethylamino)propoxy]phenyl}-5-(2-chloro-5-ethoxyphenyl)pyrazin-2-yl]carbonyl}amino)cyclohexanecarboxylic acid hydrochloride;
1-({[6-{4-chloro-3-[3-(dimethylamino)-2-fluoropropoxy]phenyl}-5-(2-methylphenyl)pyridin-2-yl]carbonyl}amino)cyclohexanecarboxylic acid hydrochloride;
2-({[6-{4-chloro-3-[3-(dimethylamino)propoxy]phenyl}-5-(2-chlorophenyl)pyridin-2-yl]carbonyl}amino)adamantane-2-carboxylic acid hydrochloride;
1-{[(6-{4-chloro-3-[3-(dimethylamino)propoxy]phenyl}-5-[2-(difluoromethyl)-5-methylphenyl]pyridin-2-yl)carbonyl]amino}cyclohexanecarboxylic acid hydrochloride;

1-[(6-{4-chloro-3-{[3-(dimethylamino)propoxy]phenyl}-5-[5-(2-methoxyethoxy)-2-methylphenyl]pyridin-2-yl)carbonyl]amino}cyclohexanecarboxylic acid hydrochloride;

1-[(6-{4-chloro-3-[3-(dimethylamino)propoxy]phenyl}-5-[5-(methoxymethyl)-2-methylphenyl]pyridin-2-yl)carbonyl]amino}cyclohexanecarboxylic acid hydrochloride;

1-[(6-{4-chloro-3-[3-(dimethylamino)propoxy]phenyl}-5-[2-methyl-5-(1-methylethoxy)phenyl]pyridin-2-yl)carbonyl]amino}cyclohexanecarboxylic acid hydrochloride;

1-[(6-{4-chloro-3-[3-(dimethylamino)propoxy]phenyl}-5-[2-methyl-5-(2-methylpropoxy)phenyl]pyridin-2-yl)carbonyl]amino}cyclohexanecarboxylic acid hydrochloride;

1-[(6-{4-chloro-3-[3-(dimethylamino)propoxy]phenyl}-5-[5-(cyclopropylmethoxy)-2-methylphenyl]pyridin-2-yl)carbonyl]amino cyclohexanecarboxylic acid hydrochloride;

1-({[6-{4-chloro-3-[3-(dimethylamino)propoxy]phenyl}-5-(2-methyl-5-propoxyphenyl)pyridin-2-yl]carbonyl}amino)cyclohexanecarboxylic acid hydrochloride;

2-({[6-{4-chloro-3-[3-(dimethylamino)propoxy]phenyl}-5-(2,6-dimethoxyphenyl)pyridin-2-yl]carbonyl}amino)-2,3-dihydro-1H-indene-2-carboxylic acid;

1-({[6-{4-chloro-3-[3-(dimethylamino)propoxy]phenyl}-5-(2,6-dimethoxyphenyl)pyridin-2-yl]carbonyl}amino)cyclopentanecarboxylic acid;

2-({[6-{4-chloro-3-[3-(dimethylamino)propoxy]phenyl}-5-(2,6-dimethoxyphenyl)pyridin-2-yl]carbonyl}amino)bicyclo[2.2.1]heptane-2-carboxylic acid hydrochloride;

N-{[6-{4-chloro-3-[3-(dimethylamino)propoxy]phenyl}-5-(2,6-dimethoxyphenyl)pyridin-2-yl]carbonyl}phenylalanine;

1-({[6-{4-chloro-3-[3-(dimethylamino)propoxy]phenyl}-5-(2-methylphenyl)pyridin-2-yl]carbonyl}amino)cyclohexanecarboxylic acid hydrochloride;

3-({[6-{4-chloro-3-[3-(dimethylamino)propoxy]phenyl}-5-(2,6-dimethoxyphenyl)pyridin-2-yl]carbonyl}amino)-4-methylpentanoic acid;

3-({[6-{4-chloro-3-[3-(dimethylamino)propoxy]phenyl}-5-(2,6-dimethoxyphenyl)pyridin-2-yl]carbonyl}amino)-4-phenylbutanoic acid;

3-({[6-{4-chloro-3-[3-(dimethylamino)propoxy]phenyl}-5-(2,6-dimethoxyphenyl)pyridin-2-yl]carbonyl}amino)-4-(1H-indol-3-yl)butanoic acid;

({[6-{4-chloro-3-[3-(dimethylamino)propoxy]phenyl}-5-(2,6-dimethoxyphenyl)pyridin-2-yl]carbonyl}amino)(phenyl)acetic acid;

3-({[6-{4-chloro-3-(dimethylamino)propoxy]phenyl}-5-(2,6-dimethoxyphenyl)pyridin-2-yl]carbonyl}amino)-3-cyclohexylpropanoic acid;

1-({[6-{4-chloro-3-[3-(dimethylamino)propoxy]phenyl}-5-(2,6-dimethoxyphenyl)pyridin-2-yl]carbonyl}amino)cyclohexanecarboxylic acid;

N-{[6-{4-chloro-3-[3-(dimethylamino)propoxy]phenyl}-5-(2,6-dimethoxyphenyl)pyridin-2-yl]carbonyl}-alpha-methylphenylalanine;

N-{[6-{4-chloro-3-[3-(dimethylamino)propoxy]phenyl}-5-(2,6-dimethoxyphenyl)pyridin-2-yl]carbonyl}-3-methylisovaline;

2-({[6-{4-chloro-3-[(1-methylpyrrolidin-3-yl)oxy]phenyl}-5-(2,6-dimethoxyphenyl)pyridin-2-yl]carbonyl}amino)adamantane-2-carboxylic acid hydrochloride;

2-({[6-{4-chloro-3-[(1-methylpiperidin-4-yl)oxy]phenyl}-5-(2,6-dimethoxyphenyl)pyridin-2-yl]carbonyl}amino)adamantane-2-carboxylic acid hydrochloride;

2-({[6-{4-chloro-3-(dimethylamino)propoxy]phenyl}-5-(2-methoxyphenyl)pyridin-2-yl]carbonyl}amino)adamantane-2-carboxylic acid hydrochloride;

2-({[6-{4-chloro-3-[3-(dimethylamino)propoxy]phenyl}-5-(2-methylphenyl)pyridin-2-yl]carbonyl}amino)adamantane-2-carboxylic acid hydrochloride;

2-({[6-{4-chloro-3-[2-(dimethylamino)ethoxy]phenyl}-5-(2,6-dimethoxyphenyl)pyridin-2-yl]carbonyl}amino)adamantane-2-carboxylic acid hydrochloride;

2-({[6-{4-chloro-3-[(1-ethylpyrrolidin-3-yl)oxy]phenyl}-5-(2,6-dimethoxyphenyepyridin-2-yl]carbonyl}amino)adamantane-2-carboxylic acid hydrochloride;

2-{([6-{4-chloro-3-[3-(dimethylamino)propoxy]phenyl}-5-phenylpyridin-2-yl)carbonyl]amino}adamantane-2-carboxylic acid hydrochloride;

2-({[6-{4-chloro-3-[3-(dimethylamino)propoxy]phenyl}-5-(2-oxopyrrolidin-1-yl)pyridin-2-yl]carbonyl}amino)adamantane-2-carboxylic acid hydrochloride;

9-({[6-{4-chloro-3-[3-(dimethylamino)propoxy]phenyl}-5-(2,6-dimethoxyphenyl)pyridin-2-yl]carbonyl}amino)bicyclo[3.3.1]nonane-9-carboxylic acid hydrochloride;

2-({[6-{4-chloro-3-[3-(diethylamino)propoxy]phenyl}-5-(2,6-dimethoxyphenyl)pyridin-2-yl]carbonyl}amino)adamantane-2-carboxylic acid hydrochloride;

2-{[(2-{4-chloro-3-[3-(dimethylamino)propoxy]phenyl}-3,4'-bipyridin-6-yl)carbonyl]amino}adamantane-2-carboxylic acid hydrochloride;

2-{[(2'-{4-chloro-3-[3-(dimethylamino)propoxy]phenyl}-2,3'-bipyridin-6'-yl)carbonyl]amino}adamantane-2-carboxylic acid hydrochloride;

3-[({4''-chloro-3''-[3-(dimethylamino)propoxy]-2,6-dimethoxy-1,1':2',1''-terphenyl-4'-yl}carbonyl)amino]-4-methylpentanoic acid;

3-({[5-{4-chloro-3-[3-(dimethylamino)propoxy]phenyl}-6-(2-methylphenyl)pyridin-3-yl]carbonyl}amino)-4-methylpentanoic acid hydrochloride;

N-{[6-{4-chloro-3-[3-(dimethylamino)propoxy]phenyl}-5-(2-methylphenyl)pyridin-2-yl]carbonyl}-3-hydroxyphenylalanine hydrochloride;

2-({[6-{4-chloro-3-[2-(1-methylpyrrolidin-2-yl)ethoxy]phenyl}-5-(2-methylphenyl)pyridin-2-yl]carbonyl}amino)adamantane-2-carboxylic acid hydrochloride;

2-({[6-{4-chloro-3-[2-(1-methylpiperidin-2-yl)ethoxy]phenyl}-5-(2-methylphenyl)pyridin-2-yl]carbonyl}amino)adamantane-2-carboxylic acid hydrochloride;

2-({[6-{3-[3-(dimethylamino)propoxy]-4-(trifluoromethyl)phenyl}-5-(2-methylphenyl)pyridin-2-yl]carbonyl}amino)adamantane-2-carboxylic acid hydrochloride;

2-({[6-{4-chloro-3-[3-(dimethylamino)propoxy]phenyl}-5-(2-ethylphenyl)pyridin-2-yl]carbonyl}amino)adamantane-2-carboxylic acid hydrochloride;

2-{[(6-{4-chloro-3-[3-(dimethylamino)propoxy]phenyl}-5-[2-(trifluoromethyl)phenyl]pyridin-2-yl)carbonyl]amino}adamantane-2-carboxylic acid hydrochloride;

2-({[6-(4-chloro-3-{3-[cyclopropyl(methyl)amino]propoxy}phenyl)-5-(2-methylphenyl)pyridin-2-yl]carbonyl}amino)adamantane-2-carboxylic acid hydrochloride;

2-{[(6-{4-chloro-3-[3-(dimethylamino)propoxy]phenyl}-5-[2-(dimethylamino)phenyl]pyridin-2-yl)carbonyl]amino}adamantane-2-carboxylic acid hydrochloride;

1-{[(3,5-dichloro-2'-{4-chloro-3-[3-(dimethylamino)propoxy]phenyl}-2,3'-bipyridin-6'-yl)carbonyl]amino}cyclohexanecarboxylic acid hydrochloride;

1-({[6-{4-chloro-3-[3-(dimethylamino)propoxy]phenyl}-5-(2,4-dimethylphenyl)pyridin-2-yl]carbonyl}amino)cyclohexanecarboxylic acid hydrochloride;

4-({[6-{4-chloro-3-[3-(dimethylamino)propoxy]phenyl}-5-(2-methylphenyl)pyridin-2-yl]carbonyl}amino)tetrahydro-2H-1-pyran-4-carboxylic acid hydrochloride;

(3R)-3-({[6-{4-chloro-3-[3-(dimethylamino)propoxy]phenyl}-5-(2-methylphenyl)pyridin-2-yl]carbonyl}amino)-4-methylpentanoic acid hydrochloride 2-[({6-[4-chloro-3-(3-piperidin-1-ylpropoxy)phenyl]-5-(2-methylphenyl)pyridin-2-yl}carbonyl)amino]adamantane-2-carboxylic acid hydrochloride;

2-({[6-{4-chloro-3-[3-(dimethylamino)butoxy]phenyl}-5-(2-methylphenyl)pyridin-2-yl]carbonyl}amino)adamantane-2-carboxylic acid hydrochloride;

2-{([6-[4-chloro-3-(2-piperidin-1-ylethoxy)phenyl]-5-(2-methylphenyl)pyridin-2-yl}carbonyl)amino]adamantane-2-carboxylic acid hydrochloride;

(3S)-3-({[6-4-chloro-3-[3-(dimethylamino)propoxy]phenyl}-5-(2-methylphenyl)pyridin-2-yl]carbonyl}amino)-4-methylpentanoic acid hydrochloride;

2-({6-[4-chloro-3-(2-pyrrolidin-1-ylethoxy)phenyl]-5-(2-methylphenyl)pyridin-2-yl}carbonyl)amino]adamantane-2-carboxylic acid hydrochloride;

2-[({6-[4-chloro-3-(3-pyrrolidin-1-ylpropoxy)phenyl]-5-(2-methylphenyl)pyridin-2-yl}carbonyl)amino]adamantane-2-carboxylic acid hydrochloride;

2-[(2'-{4-chloro-3-[3-(dimethylamino)propoxy]phenyl}-3-methyl-2,3'-bipyridin-6'-yl)carbonyl]amino}adamantane-2-carboxylic acid hydrochloride;

1-({[6-{4-chloro-3-[3-(dimethylamino)propoxy]phenyl}-5-(2-methylphenyl)pyridin-2-yl]carbonyl}amino)-4-methylcyclohexanecarboxylic acid hydrochloride;

2-({[6-{4-chloro-3-[3-(dimethylamino)-1-methylpropoxy]phenyl}-5-(2-methylphenyl)pyridin-2-yl]carbonyl}amino)adamantane-2-carboxylic acid hydrochloride;

1-({[6-{4-chloro-3-[3-(dimethylamino)propoxy]phenyl}-5-(2-chloro-4-fluorophenyl)pyridin-2-yl]carbonyl}amino)cyclohexanecarboxylic acid hydrochloride;

1-({[6-{4-chloro-3-[3-(dimethylamino)propoxy]phenyl}-5-(2-chloro-4-methoxyphenyl)pyridin-2-yl]carbonyl}amino)cyclohexanecarboxylic acid hydrochloride;

(3S)-3-({[6-{4-chloro-3-[3-(dimethylamino)propoxy]phenyl}-5-(2-chlorophenyl)pyridin-2-yl]carbonyl}amino)-4-methylpentanoic acid hydrochloride;

1-({[6-{4-chloro-3-[3-(dimethylamino)propoxy]phenyl}-5-(2-methylphenyl)pyridin-2-yl]carbonyl}amino)-4-hydroxycyclohexanecarboxylic acid hydrochloride;

1-({[6-{4-chloro-3-(dimethylamino)propoxy]phenyl}-5-(2-chlorophenyl)pyridin-2-yl]carbonyl}amino)cyclohexanecarboxylic acid hydrochloride;

2-({[6-(4-chloro-3-{[(2R)-3-(dimethylamino)-2-hydroxypropyl]oxy}phenyl)-5-(2-methylphenyl)pyridin-2-yl]carbonyl}amino)adamantane-2-carboxylic acid hydrochloride;

2-({[6-(4-chloro-3-{[(2S)-3-(dimethylamino)-2-hydroxypropyl]oxy}phenyl)-5-(2-methylphenyl)pyridin-2-yl]carbonyl}amino)adamantane-2-carboxylic acid hydrochloride;

acetyl-4-({[6-{4-chloro-3-[3-(dimethylamino)propoxy]phenyl}-5-(2-methylphenyl)pyridin-2-yl]carbonyl}amino)piperidine-4-carboxylic acid hydrochloride;

2-({[6-{4-chloro-3-[2-(diethylamino)ethoxy]phenyl}-5-(2-methylphenyl)pyridin-2-yl]carbonyl}amino)adamantane-2-carboxylic acid hydrochloride;

1-{[(6-{4-chloro-3-(dimethylamino)propoxy]phenyl}-5-[2-(difluoromethyl)phenyl]pyridin-2-yl)carbonyl]amino}cyclohexanecarboxylic acid hydrochloride;

[1-({[6-{4-chloro-3-[3-(dimethylamino)propoxy]phenyl}-5-(2-methylphenyl)pyridin-2-yl]carbonyl}amino)cyclohexyl]acetic acid hydrochloride;

1-({[6-{4-chloro-3-[3-(dimethylamino)propoxy]phenyl}-5-(2-chlorophenyl)pyridin-2-yl]carbonyl}amino)-4-hydroxycyclohexanecarboxylic acid hydrochloride;

1-{[(3-chloro-2'-{4-chloro-3-[3-(dimethylamino)propoxy]phenyl}-2,3'-bipyridin-6'-yl)carbonyl]amino}cyclohexanecarboxylic acid hydrochloride;

1-{[(3-amino-2'-{4-chloro-3-[3-(dimethylamino)propoxy]phenyl}-2,3'-bipyridin-6'-yl)carbonyl]amino}cyclohexanecarboxylic acid hydrochloride;

1-({[6-{4-chloro-3-[3-(dimethylamino)propoxy]phenyl}-5-(2-methylphenyl)pyridin-2-yl]carbonyl}amino)-3-hydroxycyclohexanecarboxylic acid hydrochloride;

1-({[6-{4-chloro-3-[3-(dimethylamino)propoxy]phenyl}-5-(2-methylphenyl)pyridin-2-yl]carbonyl}amino)-3-hydroxycyclohexanecarboxylic acid hydrochloride;

cis-1-({[6-{4-chloro-3-[3-(dimethylamino)propoxy]phenyl}-5-(2-chlorophenyl)pyridin-2-yl]carbonyl}amino)-4-methoxycyclohexanecarboxylic acid hydrochloride;

trans-1-({[6-{4-chloro-3-[3-(dimethylamino)propoxy]phenyl}-5-(2-chlorophenyl)pyridin-2-yl]carbonyl}amino)-4-methoxycyclohexanecarboxylic acid hydrochloride trans-1-({[6-{4-chloro-3-[3-(dimethylamino)propoxy]phenyl}-5-(2-methylphenyl)pyridin-2-yl]carbonyl}amino)-4-hydroxycyclohexanecarboxylic acid hydrochloride;

1-{[(6-{4-chloro-3-[3-(dimethylamino)propoxy]phenyl}-5-[2-(methylsulphonyl)phenyl]pyridin-2-yl)carbonyl]amino}cyclohexanecarboxylic acid hydrochloride;

1-{[(6-{4-chloro-3-[3-(dimethylamino)propoxy]phenyl}-5-[2-(methylsulphonyl)phenyl]pyridin-2-yl)carbonyl]amino}cyclohexanecarboxylic acid hydrochloride;

1-{[(2'-{4-chloro-3-[3-(dimethylamino)propoxy]phenyl}-3-methyl-2,3'-bipyridin-6'-yl)carbonyl]amino}cyclohexanecarboxylic acid hydrochloride;

1-{[(5-(2-(acetylamino)phenyl]-6-{4-chloro-3-[3-(dimethylamino)propoxy]phenyl}pyridin-2-yl)carbonyl]amino}cyclohexanecarboxylic acid hydrochloride;

N-{[6-{4-chloro-3-[3-(dimethylamino)propoxy]phenyl}-5-(2-chlorophenyl)pyridin-2-yl]carbonyl}-D-valine hydrochloride;

1-{[(2-{4-chloro-3-[3-(dimethylamino)propoxy]phenyl}-2'-methyl-3,3'-bipyridin-6-yl)carbonyl]amino}cyclohexanecarboxylic acid hydrochloride;

1-{[(2-{4-chloro-3-[3-(dimethylamino)propoxy]phenyl}-4'-methyl-3,3'-bipyridin-6-yl)carbonyl]amino}cyclohexanecarboxylic acid hydrochloride;

1-[({6-[4-chloro-3-(2-pyrrolidin-1-ylethoxy)phenyl]-5-(2-methylphenyl)pyridin-2-yl]carbonyl)amino]-4-hydroxycyclohexanecarboxylic acid hydrochloride;

1-({[6-(4-chloro-3-{3-[ethyl(methyl)amino]propoxy}phenyl)-5-(2-methylphenyl)pyridin-2-yl]carbonyl}amino)-4-hydroxycyclohexanecarboxylic acid hydrochloride;

1-({[6-{4-chloro-3-[3-(diethylamino)propoxy]phenyl}-5-(2-methylphenyl)pyridin-2-yl]carbonyl}amino)-4-hydroxycyclohexanecarboxylic acid hydrochloride;

1-({[6-{4-chloro-3-[4-(dimethylamino)butoxy]phenyl}-5-(2-methylphenyl)pyridin-2-yl]carbonyl}amino)-4-hydroxycyclohexanecarboxylic acid hydrochloride;

1-{[(6-{4-chloro-3-[3-(dimethylamino)propoxy]phenyl}-5-[2-(1-methylethyl)phenyl]pyridin-2-yl)carbonyl]amino}-4-hydroxycyclohexanecarboxylic acid hydrochloride;

1-({[6-{4-chloro-3-[3-(dimethylamino)propoxy]phenyl}-5-(2-ethylphenyl)pyridin-2-yl]carbonyl}amino)-4-hydroxycyclohexanecarboxylic acid hydrochloride;

1-({[6-{4-chloro-3-(dimethylamino)propoxy]phenyl}-5-(5-chloro-2-methylphenyl)pyridin-2-yl]carbonyl}amino)-4-hydroxycyclohexanecarboxylic acid hydrochloride;

1-({[6-{4-chloro-3-[3-(dimethylamino)propoxy]phenyl}-5-(2,4-dimethylphenyl)pyridin-2-yl]carbonyl}amino)-4-hydroxycyclohexanecarboxylic acid hydrochloride;

1-({[6-{4-chloro-3-[3-(dimethylamino)propoxy]phenyl}-5-(2,5-dimethylphenyl)pyridin-2-yl]carbonyl}amino)-4-hydroxycyclohexanecarboxylic acid hydrochloride;

1-({[6-(4-chloro-3-{3-[ethyl(methyl)amino]propoxy}phenyl)-5-(2,4-dimethylphenyl)pyridin-2-yl]carbonyl}amino)-4-hydroxycyclohexanecarboxylic acid hydrochloride;

1-({[6-{4-chloro-3-[3-(dimethylamino)propoxy]phenyl}-5-(4-fluoro-2-methylphenyl)pyridin-2-yl]carbonyl}amino)-4-hydroxycyclohexanecarboxylic acid hydrochloride;

1-({[6-(4-chloro-3-{3-[methyl(propyl)amino]propoxy}phenyl)-5-(2-ethylphenyl)pyridin-2-yl]carbonyl}amino)-4-hydroxycyclohexanecarboxylic acid hydrochloride;

1-({[6-{4-chloro-3-(diethylamino)propoxy]phenyl}-5-(2,4-dimethylphenyl)pyridin-2-yl]carbonyl}amino)-4-hydroxycyclohexanecarboxylic acid hydrochloride;

1-({[6-(4-chloro-3-{3-[ethyl(methyl)amino]propoxyl}phenyl)-5-(2-ethylphenyl)pyridin-2-yl]carbonyl}amino)-4-hydroxycyclohexanecarboxylic acid hydrochloride;

1-({[6-{4-chloro-3-[3-(dimethylamino)propoxy]phenyl}-5-(2-ethylphenyl)pyridin-2-yl]carbonyl}amino)cyclohexanecarboxylic acid hydrochloride;

1-({[6-{4-chloro-3-[3-(dimethylamino)-2-methylpropoxy]phenyl}-5-(2-ethylphenyl)pyridin-2-yl]carbonyl}amino)-3-hydroxycyclohexanecarboxylic acid hydrochloride;

1-({[6-{4-chloro-3-[3-(dimethylamino)propoxy]phenyl}-5-(2-propylphenyl)pyridin-2-yl]carbonyl}amino)-4-hydroxycyclohexanecarboxylic acid hydrochloride;

1-{[(3-chloro-2'-{4-chloro-3-[3-(dimethylamino)propoxy]phenyl}-5-fluoro-2,3'-bipyridin-6'-yl)carbonyl]amino}cyclohexanecarboxylic acid hydrochloride;

1-({[6-{4-chloro-3-[3-(dimethylamino)propoxy]phenyl}-5-(2-chloro-5-methylphenyl)pyridin-2-yl]carbonyl}amino)-4-hydroxycyclohexanecarboxylic acid hydrochloride;

1-({[3-chloro-2'-(4-chloro-3-{3-[ethyl(methyl)amino]propoxy}phenyl)-2,3'-bipyridin-6'-yl]carbonyl}amino)cyclohexanecarboxylic acid hydrochloride;

1-({[6-{4-chloro-3-(dimethylamino)propoxy]phenyl}-5-(2,5-dimethylphenyl)pyridin-2-yl]carbonyl}amino)cyclohexanecarboxylic acid hydrochloride;

1-({[6-{4-chloro-3-[3-(dimethylamino)propoxy]phenyl}-5-(2-methylphenyl)pyridin-2-yl]carbonyl}amino)cycloheptanecarboxylic acid hydrochloride;

(3S)-3-({[6-{4-chloro-3-[3-(dimethylamino)propoxy]phenyl}-5-(2-chloro-5-methylphenyl)pyridin-2-yl]carbonyl}amino)-4-methylpentanoic acid hydrochloride;

1-({[6-{4-chloro-3-[3-(dimethylamino)propoxy]phenyl}-5-(2-chloro-5-fluorophenyl)pyridin-2-yl]carbonyl}amino)cyclohexanecarboxylic acid hydrochloride;

1-({[6-{4-chloro-3-[3-(dimethylamino)propoxy]phenyl}-5-(3,5-dimethyl-1H-pyrazol-1-yl)pyridin-2-yl]carbonyl}amino)cyclohexanecarboxylic acid hydrochloride;

1-({[6-{4-chloro-3-[3-(dimethylamino)propoxy]phenyl}-5-(2-chloro-5-methoxyphenyl)pyridin-2-yl]carbonyl}amino)cyclohexanecarboxylic acid hydrochloride;

1-({[6-{3-[3-(dimethylamino)propoxy]-4-ethylphenyl}-5-(2-methylphenyl)pyridin-2-yl]carbonyl}amino)cyclohexanecarboxylic acid hydrochloride;

3-({[6-{4-chloro-3-[3-(dimethylamino)propoxy]phenyl}-5-(2-chloro-5-methylphenyl)pyridin-2-yl]carbonyl}amino)-3-cyclobutylpropanoic acid hydrochloride;

1-({[6-{4-chloro-3-[3-(dimethylamino)propoxy]phenyl}-5-(2-methylthiophen-3-yl)pyridin-2-yl]carbonyl}amino)cyclohexanecarboxylic acid hydrochloride;

3-({[6-{4-chloro-3-[3-(dimethylamino)propoxy]phenyl}-5-(2-chloro-5-methylphenyl)pyridin-2-yl]carbonyl}amino)-3-cyclopropylpropanoic acid hydrochloride;

1-({[6-{4-chloro-3-[3-(dimethylamino)propoxy]phenyl}-5-(2-methylphenyl)pyrazin-2-yl]carbonyl}amino)cyclohexanecarboxylic acid hydrochloride;

1-({[6-{4-chloro-3-[3-(dimethylamino)propoxy]phenyl}-5-(2-chloro-4-hydroxyphenyl)pyridin-2-yl]carbonyl}amino)cyclohexanecarboxylic acid hydrochloride;

1-({[6-{4-chloro-3-[3-(dimethylamino)propoxy]phenyl}-5-(2-chloro-4,5-dimethylphenyl)pyridin-2-yl]carbonyl}amino)cyclohexanecarboxylic acid hydrochloride;

1-({[6-{4-chloro-3-[3-(dimethylamino)propoxy]phenyl}-5-(5-methyl-1,3-thiazol-4-yl)pyridin-2-yl]carbonyl}amino)cyclohexanecarboxylic acid hydrochloride;

4-({[6-{4-chloro-3-[3-(dimethylamino)propoxy]phenyl}-5-(2-methylphenyl)pyridin-2-yl]carbonyl}amino)oxepane-4-carboxylic acid hydrochloride;

3-({[6-{4-chloro-3-[3-(dimethylamino)propoxy]phenyl}-5-(2-chlorophenyl)pyridin-2-yl]carbonyl}amino)-4,4-dimethylpentanoic acid hydrochloride;

1-({[6-{4-chloro-3-[3-(dimethylamino)propoxy]phenyl}-5-(2-cyanophenyl)pyridin-2-yl]carbonyl}amino)cyclohexanecarboxylic acid hydrochloride;

1-({[6-{4-chloro-3-[3-(dimethylamino)propoxy]phenyl}-5-(4-hydroxy-2-methylphenyl)pyridin-2-yl]carbonyl}amino)cyclohexanecarboxylic acid hydrochloride;

1-({[6-{4-chloro-3-[3-(dimethylamino)propoxy]phenyl}-5-(3-fluoro-2-methylphenyl)pyridin-2-yl]carbonyl}amino)cyclohexanecarboxylic acid hydrochloride;

1-({[6-{4-chloro-3-[3-(dimethylamino)propoxy]phenyl}-5-(5-hydroxy-2-methylphenyl)pyridin-2-yl]carbonyl}amino)cyclohexanecarboxylic acid hydrochloride;

1-({[6-{4-chloro-3-[3-(dimethylamino)propoxy]phenyl}-5-(2-chloro-6-fluorophenyl)pyridin-2-yl]carbonyl}amino)cyclohexanecarboxylic acid hydrochloride;

1-({[6-(4-chloro-3-{3-[(2-hydroxyethyl)(methyl)amino]propoxy}phenyl)-5-(2,4-dimethylphenyl)pyridin-2-yl]carbonyl}amino)cyclohexanecarboxylic acid hydrochloride;

1-({[6-{4-chloro-3-[3-(dimethylamino)propoxy]phenyl}-5-(3-hydroxy-2-methylphenyl)pyridin-2-yl]carbonyl}amino)cyclohexanecarboxylic acid hydrochloride;

1-({[6-{4-chloro-3-[3-(dimethylamino)propoxy]phenyl}-5-(4,5-difluoro-2-methylphenyl)pyridin-2-yl]carbonyl}amino)cyclohexanecarboxylic acid hydrochloride;

1-({[6-{4-chloro-3-[3-(dimethylamino)propoxy]phenyl}-5-(6-methyl-1,3-benzodioxol-5-yl)pyridin-2-yl]carbonyl}amino)cyclohexanecarboxylic acid hydrochloride;

1-({[6-{4-chloro-3-[3-(dimethylamino)propoxy]phenyl}-5-(3,5-diethyl-1H-pyrazol-1-yl)pyridin-2-yl]carbonyl}amino)cyclohexanecarboxylic acid hydrochloride;

1-({[6-{4-chloro-3-[3-(dimethylamino)propoxy]phenyl}-5-(2-chloro-5-ethoxyphenyl)pyridin-2-yl]carbonyl}amino)cyclohexanecarboxylic acid hydrochloride;

1-({[5-chloro-2'-{4-chloro-3-[3-(dimethylamino)propoxy]phenyl}-3-(difluoromethyl)-2,3'-bipyridin-6'-yl]carbonyl}amino)cyclohexanecarboxylic acid hydrochloride;

1-{[(6-{4-chloro-3-[3-(dimethylamino)propoxy]phenyl}-5-[2-methylphenyl]pyridin-2-yl)carbonyl]amino}cyclohexanecarboxylic acid hydrochloride;

1-{[(6-{4-chloro-3-[3-(dimethylamino)propoxy]phenyl}-5-[2-methylphenyl]-3-[methylamino]pyridin-2-yl)carbonyl]amino}cyclohexanecarboxylic acid hydrochloride;

1-({[6-{4-chloro-3-[3-(dimethylamino)propoxy]phenyl}-5-(5-ethyl-3-methyl-1H-pyrazol-1-yl)pyridin-2-yl]carbonyl}amino)cyclohexanecarboxylic acid hydrochloride;

1-{[(5-[2-chloro-4-(dimethylamino)phenyl]-6-{4-chloro-3-[3-(dimethylamino)propoxy]phenyl}pyridin-2-yl)carbonyl]amino}cyclohexanecarboxylic acid hydrochloride;

(3S)-3-({[6-{4-chloro-3-[3-(dimethylamino)propoxy]phenyl}-5-(2-chlorophenyl)pyridin-2-yl]carbonyl}amino)-4,4-dimethylpentanoic acid hydrochloride;

1-{[(6-{4-chloro-3-[3-(dimethylamino)propoxy]phenyl}-5-[2-chloro-5-(trifluoromethoxy)phenyl]pyridin-2-yl)carbonyl]amino}cyclohexanecarboxylic acid hydrochloride;

1-({[3-amino-6-{4-chloro-3-[3-(dimethylamino)propoxy]phenyl}-5-(2-methylphenyl)pyrazin-2-yl]carbonyl}amino)cyclohexanecarboxylic acid hydrochloride;

1-({[6-{4-chloro-3-[3-(dimethylamino)propoxy]phenyl}-5-(2,4-dichlorophenyl)pyridin-2-yl]carbonyl}amino)cyclohexanecarboxylic acid hydrochloride;

1-({[6-{4-chloro-3-[3-(dimethylamino)propoxy]phenyl}-5-(2-methylphenyl)pyridin-2-yl]carbonyl}amino)-4,4-difluorocyclohexanecarboxylic acid hydrochloride;

1-({[6-{4-chloro-3-[3-(dimethylamino)propoxy]phenyl}-3-(methylamino)-5-(2-methylphenyl)pyridin-2-yl]carbonyl}amino)cyclohexanecarboxylic acid hydrochloride;

1-({[6-{4-chloro-[3-(dimethylamino)propoxy]phenyl}-5-(2-chloro-4-fluorophenyl)pyridin-2-yl]carbonyl}amino)cyclohexanecarboxylic acid hydrochloride;

1-({[6-{4-chloro-[3-(dimethylamino)propoxy]phenyl}-5-(2-chloro-4-methoxyphenyl)pyridin-2-yl]carbonyl}amino)cyclohexanecarboxylic acid hydrochloride; or 1-{[(6-{4-chloro-3-[3-(dimethylamino)propoxy]phenyl}-5-[2-(difluoromethyl)phenyl]pyridin-2-yl)carbonyl]amino}cyclohexanecarboxylic acid hydrochloride.

15. A compound of formula (III):

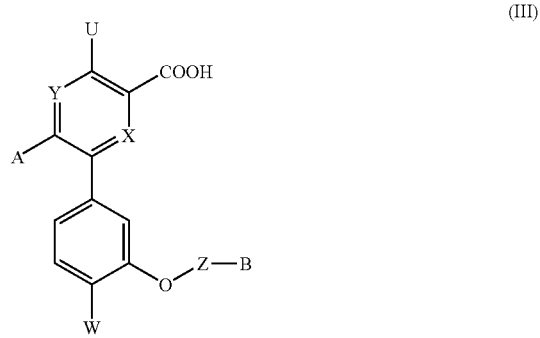

(III)

in which U, X, Y, Z, W, A and B are as defined in formula (I) of claim 1.

16. A method of preparing a compound of formula (I) of claim 1 comprising the step of reacting a compound of formula (III)

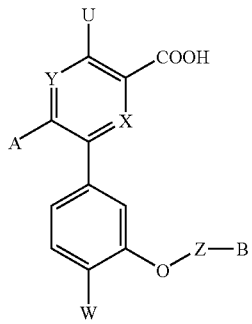

(III)

in which U, X, Y, Z, W, A and B are as defined in formula I of claim 1, with a compound of formula (II)

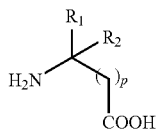

(II)

in which p, R1 and R2 are as defined in formula I of claim 1, in the presence of a coupling agent, a weak organic base and a polar aprotic solvent at room temperature.

17. A method of preparing a compound of formula (I) of claim 1, comprising the steps of:

a) reacting a compound of formula (V)

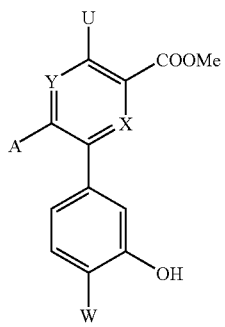

(V)

in which U, X, Y, W and A are as defined in formula I of claim 1, with a chlorine derivative Cl—Z—B, wherein Z and B are as defined for claim 1, in the presence of a weak inorganic base in a polar aprotic solvent at a temperature between 80° C. and 100° C., or with an alcohol of formula HO—Z—B, wherein Z and B are as defined for claim 1, in the presence of triphenylphosphine, diisopropyl azodicarboxylate (DIAD), and a catalytic amount of a weak organic base at 0° C. in an aprotic solvent, to obtain a compound of formula (IV)

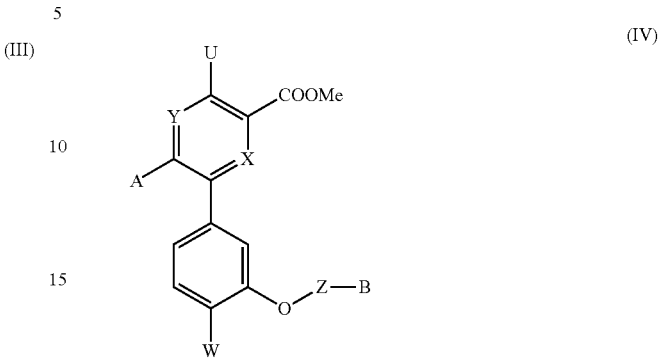

(IV)

in which U, X, Y, W, A, Z and B are as defined in formula I of claim 1, b) saponifying said compound of formula (IV) by means of a strong inorganic base in a water/methanol mixture maintained at room temperature or heated under reflux, then acidifying, in order to obtain a compound of formula (III)

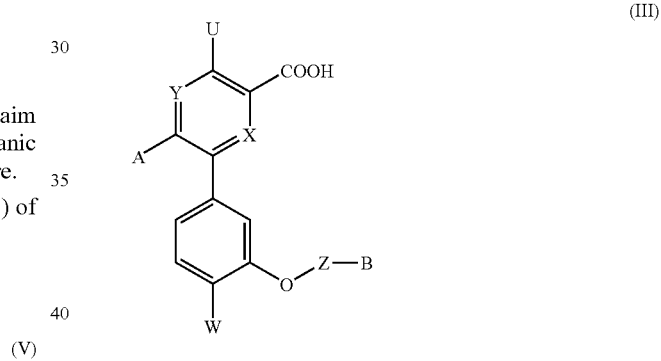

(III)

in which U, X, Y, W, A, Z and B are as defined in formula I of claim 1; and c) reacting said compound of formula (III) with a compound of formula (II)

(II)

in which p, R1 and R2 are as defined in formula I of claim 1.

18. A pharmaceutical composition comprising a compound of formula (I) of claim 1, or an enantiomer, diastereomer, racemate, or pharmaceutically acceptable salt thereof, and a pharmaceutically acceptable carrier.

19. A method of treating vomiting comprising administering to a patient in need thereof a therapeutically effective amount of a compound of formula (I) of claim 1 or an enantiomer, diastereomer, racemate, or pharmaceutically acceptable salt thereof.

* * * * *